US010961503B2

(12) United States Patent
Egli et al.

(10) Patent No.: US 10,961,503 B2
(45) Date of Patent: Mar. 30, 2021

(54) HAPLOID HUMAN EMBRYONIC STEM CELL LINES AND SOMATIC CELL LINES AND METHODS OF MAKING THE SAME

(71) Applicants: New York Stem Cell Foundation, Inc., New York, NY (US); Yissum Research Development Company of the Hebrew University of Jerusalem Ltd., Jerusalem (IL)

(72) Inventors: Dietrich M. Egli, New York, NY (US); Nissim Benvenisty, Jerusalem (IL); Ido Sagi, Jerusalem (IL)

(73) Assignees: New York Stem Cell Foundation, Inc., New York, NY (US); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 18 days.

(21) Appl. No.: 15/747,103

(22) PCT Filed: Jul. 28, 2016

(86) PCT No.: PCT/US2016/044561
§ 371 (c)(1),
(2) Date: Jan. 23, 2018

(87) PCT Pub. No.: WO2017/019902
PCT Pub. Date: Feb. 2, 2017

(65) Prior Publication Data
US 2018/0208890 A1 Jul. 26, 2018

Related U.S. Application Data

(60) Provisional application No. 62/292,755, filed on Feb. 8, 2016, provisional application No. 62/279,490, filed on Jan. 15, 2016, provisional application No. 62/198,614, filed on Jul. 29, 2015.

(51) Int. Cl.
*C12N 5/0735* (2010.01)
*C12N 5/075* (2010.01)
*C12N 5/071* (2010.01)

(52) U.S. Cl.
CPC ......... *C12N 5/0606* (2013.01); *C12N 5/0609* (2013.01); *C12N 5/0612* (2013.01); *C12N 2501/115* (2013.01); *C12N 2501/727* (2013.01); *C12N 2501/999* (2013.01); *C12N 2506/04* (2013.01); *C12N 2517/04* (2013.01); *C12N 2517/10* (2013.01)

(58) Field of Classification Search
CPC .................................................. C12N 5/0606
See application file for complete search history.

(56) References Cited

U.S. PATENT DOCUMENTS

| | | | |
|---|---|---|---|
| 8,420,393 B2 | 4/2013 | Revazova et al. | |
| 9,957,479 B2 * | 5/2018 | Wutz | C12N 5/0606 |
| 2014/0057801 A1 * | 2/2014 | Wutz | C12N 5/0606 506/9 |
| 2014/0342369 A1 | 11/2014 | Elling et al. | |

FOREIGN PATENT DOCUMENTS

| | | | |
|---|---|---|---|
| EP | 2 599 859 A1 | 6/2013 | |
| JP | 2009512450 | 3/2009 | |
| JP | 2015500637 | 1/2015 | |
| WO | WO 2001/30978 A1 | 5/2001 | |
| WO | WO 2007/047979 A2 | 4/2007 | |
| WO | WO 2008/033469 A1 | 3/2008 | |
| WO | WO-2013079670 A1 * | 6/2013 | ........... C12N 5/0606 |
| WO | 2015152146 | 10/2015 | |

OTHER PUBLICATIONS

Carrette et al. (Year: 2009).*
Bai, M. et al.: "*Generation and application of mammalian haploid embryonic stem cells*"; Journal of Internal Medicine, vol. 280, No. 3, May 3, 2016, pp. 236-245, XP055305141.
Carette, Jan E. et al.: "*Haploid Genetic Screens in Human Cells Identify Host Factors Used by Pathogens*"; Science, American Association for the Advancement of Science, US, vol. 326, No. 5957, Nov. 27, 2009, pp. 1231-1235, XP008150319. (Abstract).
International Search Report dated Oct. 4, 2016, regarding PCT/US2016/044561.
Leeb, Martin et al.: "*Derivation of haploid embryonic stem cells from mouse embryos*"; Nature, vol. 479, No. 7371, Sep. 7, 2011, pp. 131-134, XP055029866.
Sagi, Ido et al.: "*Derivation and differentiation of haploid human embryonic stem cells*"; Nature, vol. 532, No. 7597, Apr. 7, 2016, pp. 107-111, XP055305069. (Abstract).
Wutz, A.: "*Haploid animal cells*"; Development, vol. 141, No. 7, Mar. 18, 2014, pp. 1423-1426, XP055304942.
Yang, Hui et al.: "*Generation of haploid embryonic stem cells from Macaca fascicularis monkey parthenotes*"; Cell Research—Xibao Yanjiu, vol. 23, No. 10, Jul. 16, 2013, pp. 1187-1200, XP055305022.
Zhong, Cuiqing et al.: "*Generation of human haploid embryonic stem cells from parthenogenetic embryos obtained by microsurgical removal of male pronucleus*"; Cell Research—Xibao Yanjiu, vol. 26, No. 6, May 17, 2016, pp. 743-746, XP055305073.
Kotecki, et al., "Isolation and Characterization of a Near-Haploid Human Cell Line", Experimental Cell Research, vol. 252 (1999), pp. 273-280.
Wan, et al., "Parthenogenetic haploid embryonic stem cells produce fertile mice", Cell Research, vol. 23, 1330-1333 (2013).

(Continued)

*Primary Examiner* — Thaian N. Ton
*Assistant Examiner* — David A. Montanari
(74) *Attorney, Agent, or Firm* — The Roy Gross Law Firm, LLC; Roy Gross

(57) ABSTRACT

Haploid human embryonic stem cells and cell lines, haploid multipotent human cells, and haploid differentiated human cells are provided. In addition, methods of making and using the haploid human cells are provided.

9 Claims, 43 Drawing Sheets

Figure 1A:
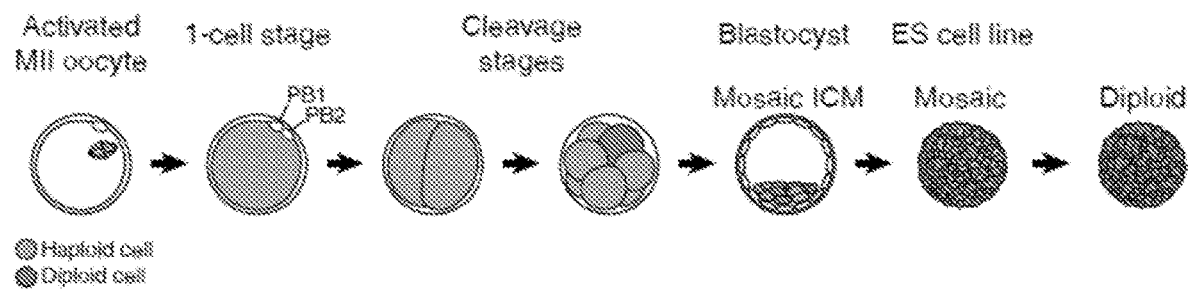

Specification includes a Sequence Listing.

(56) References Cited

OTHER PUBLICATIONS

Elling, et al., "Forward and Reverse Genetics through Derivation of Haploid Mouse Embryonic Stem Cells", Cell Stem Cell, vol. 9 (2011), pp. 563-574.
Carette, et al., "Ebola virus entry requires the cholesterol transporter Niemann-Pick C1", Nature. Aug. 24, 2011;477 (7364):340-3.
Schimenti, J., "Haploid Embryonic Stem Cells and the Dominance of Recessive Traits", Cell Stem Cell, vol. 9, Issue 6, Dec. 2, 2011, pp. 488-489.
Li, et al., "Androgenetic haploid embryonic stem cells produce live transgenic mice", Nature 490, 407-411 (2012).
Leeb, et al., "Germline potential of parthenogenetic haploid mouse embryonic stem cells", Development and Stem Cells, vol. 139 No. 18, 3301-3305, 2012.
Yang, et al., "Generation of Genetically Modified Mice by Oocyte Injection of Androgenetic Haploid Embryonic Stem Cells", Cell, vol. 149, Issue 3, Apr. 27, 2012, pp. 605-617.
Shi, et al., "Haploid embryonic stem cells: an ideal tool for mammalian genetic analyses", Protein & Cell vol. 3, 806-810 (2012).
Leeb, et al., "Haploid genomes illustrate epigenetic constraints and gene dosage effects in mammals", Epigenetics & Chromatin, vol. 6, 41 (2013).
Leeb, et al., "Genetic Exploration of the Exit from Self-Renewal Using Haploid Embryonic Stem Cells", Cell Stem Cell, vol. 14, Issue 3, Mar. 6, 2014, pp. 385-393.
Pettitt, et al., "A Genetic Screen Using the PiggyBac Transposon in Haploid Cells Identifies Parp1 as a Mediator of Olaparib Toxicity", PLoS ONE vol. 8(4): e61520, 2013.
Essletzbichler, et al., "Megabase-scale deletion using CRISPR/Cas9 to generate a fully haploid human cell line", Genome Research, Dec. 2014;24(12):2059-65.
Takahashi, et al., "Induction of the G2/M transition stabilizes haploid embryonic stem cells", Development 2014 141:3842-3847.
Li, et al., "Genetic Modification and Screening in Rat Using Haploid Embryonic Stem Cells, Cell Stem Cell", vol. 14, Issue 3, Mar. 6, 2014, pp. 404-414.
Wutz, et al., "Haploid Mouse Embryonic Stem Cells: Rapid Genetic Screening and Germline Transmission", Annual Review of Cell and Developmental Biology, vol. 30:705-722, 2014.
Dixon, et al., "Human Haploid Cell Genetics Reveals Roles for Lipid Metabolism Genes in Nonapoptotic Cell Death", ACS Chemical Biology, 2015, 10, 7, 1604-1609, Publication Date:May 12, 2015.
Blomen, et al., "Gene essentiality and synthetic lethality in haploid human cells", Science Nov. 27, 2015: vol. 350, Issue 6264, pp. 1092-1096.
Monfort, et al., "Identification of Spen as a Crucial Factor for Xist Function through Forward Genetic Screening in Haploid Embryonic Stem Cells", Cell Reports, vol. 12, Issue 4, Jul. 28, 2015, pp. 554-561.
Kimura, et al., "CRISPR/Cas9-mediated reporter knock-in in mouse haploid embryonic stem cells", Scientific Reports vol. 5, 10710 (2015).
Zhong, et al., "CRISPR-Cas9-Mediated Genetic Screening in Mice with Haploid Embryonic Stem Cells Carrying a Guide RNA Library", Cell Stem Cell, vol. 17, Issue 2, Aug. 6, 2015, pp. 221-232.
Horii, et al., "Genome Editing Using Mammalian Haploid Cells", International Journal of Molecular Sciences 2015, vol. 16, 23604-23614.

\* cited by examiner

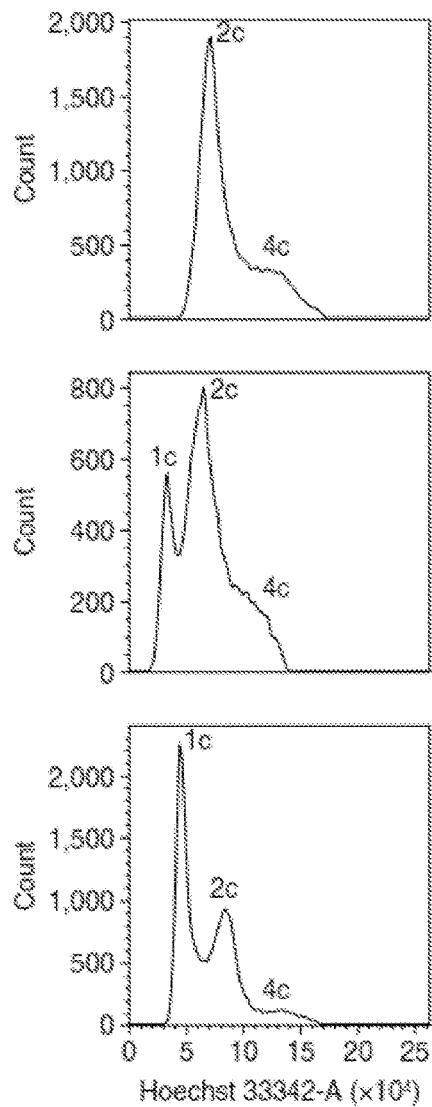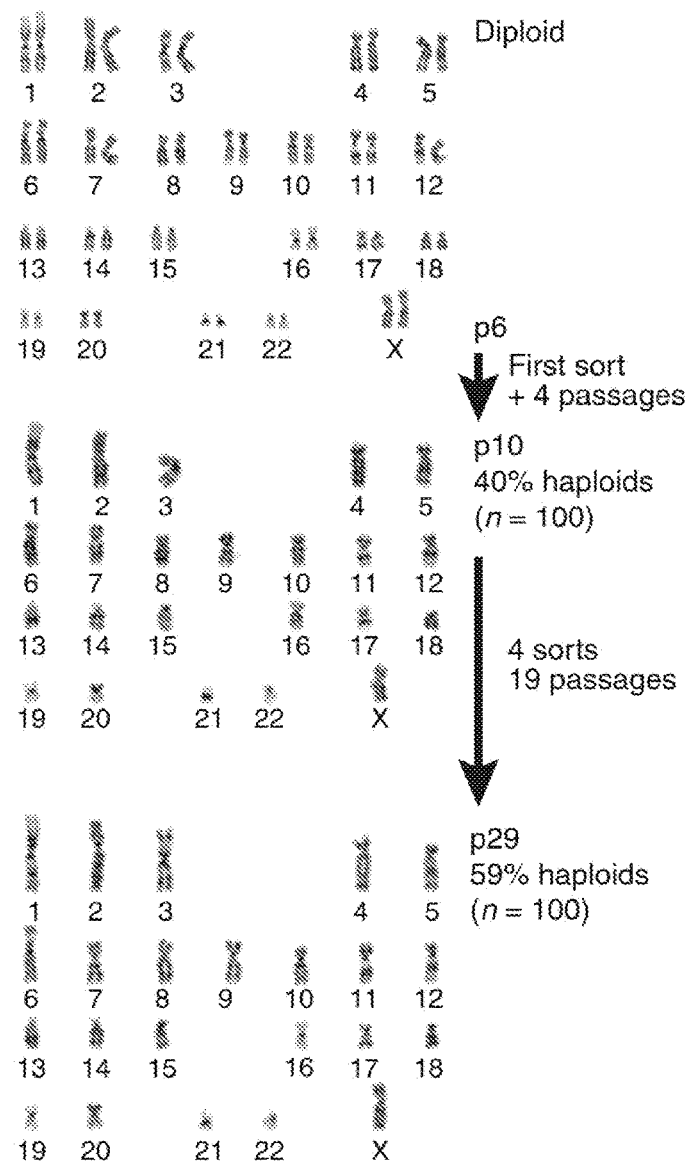
Figure 5A
Figure 5B

HAPLOID HUMAN EMBRYONIC STEM CELL LINES AND SOMATIC CELL LINES AND METHODS OF MAKING THE SAME

CROSS-REFERENCE TO RELATED APPLICATIONS

This application is a 35 USC § 371 National Stage application of International Application No. PCT/US2016/044561 filed Jul. 28, 2016, now pending; which claims the benefit under 35 USC § 119(e) to U.S. Application Ser. No. 62/292,755 filed Feb. 8, 2016, U.S. Application Ser. No. 62/279,490 filed Jan. 15, 2016 and U.S. Application Ser. No. 62/198,614 filed Jul. 29, 2015. The disclosure of each of the prior applications is considered part of and is incorporated by reference in the disclosure of this application.

INCORPORATION OF SEQUENCE LISTING

The material in the accompanying sequence listing is hereby incorporated by reference into this application. The accompanying sequence listing text file, named NYSC1270-3_ST25.txt, was created on Jan. 19, 2018 and is 2 KB. The file can be accessed using Microsoft Word on a computer that used Windows OS.

BACKGROUND

Diploidy is a fundamental genetic feature in mammals, in which haploid cells normally arise only as post-meiotic germ cells that serve to insure a diploid genome upon fertilization. Gamete manipulation has yielded haploid embryonic stem (ES) cells from several mammalian species,[1-6] but prior to the present invention, not from humans.

Haploid genetics is a useful tool for delineating genome function, and haploid mammalian cells have proven invaluable through loss-of-function genetic screens, since single-allele mutations are sufficient to induce a phenotype.[7] The derivation of haploid human ES cell lines has likely been hindered by the limited availability of human oocytes.[10] Therefore, in humans, loss-of-function screens have thus far been facilitated through a near-haploid chronic myeloid leukemia cell line[30] and its derivative cells.[31] Although useful, these are chromosomally aberrant cancer cells representing a single cell type. In that sense, the benefit in utilizing haploid human ES cells for genetic screens relies on the premise of their genomic stability, their capacity to model human early development and their potential to give rise to virtually any cell type of interest.

Although the increasing efficiency of clustered regularly interspaced short palindromic repeats (CRISPR)/Cas9-mediated mutagenesis can facilitate loss-of-function screens in diploid cells, each allele may be affected differently, making functional gene disruption more efficient in a haploid genome.[32,33] Moreover, while the use of CRISPR/Cas9 requires predesigned single-guide RNAs (sgRNAs), less biased mutagenesis approaches, such as the gene trap method, can be readily applied to haploid but not diploid cells for loss-of-function screens.[7]

Throughout evolution, mammalian genomes have been solidified by diploidy-dependent adaptations such as parental imprinting, which restrict the development of haploid uniparental embryos. Nonetheless, haploid cells are capable of directing development in certain animal species.34 The surprising differentiation potential of haploid human genomes suggests that diploidy-dependent adaptations, rather than haploidy, may pose the predominant barriers for development in humans. Our discovery of haploid human ES cells thus provides novel means to delineate basic aspects of human genetics and development.

SUMMARY OF THE INVENTION

Artificial activation of unfertilized metaphase II (MII) human oocytes results in efficient development to the blastocyst stage and subsequent derivation of parthenogenetic ES (pES) cell lines.[13-15] Although second polar body extrusion at MII results in a haploid egg, these ES cells have been repeatedly reported as diploid. We generated and analyzed a collection of human parthenogenetic ES cell lines originating from haploid oocytes, leading to the successful isolation and maintenance of human ES cell lines with a normal haploid karyotype. Haploid human ES cells exhibited pluripotent stem cell characteristics, such as self-renewal capacity and a pluripotency-specific molecular signature. Moreover, we demonstrated the utility of these cells as a platform for loss-of-function genetic screening, using a library of gene-trapped haploid human ES cells.

However, haploid human ES cells also displayed distinct properties from their diploid counterparts, including differential regulation of X chromosome inactivation and genes involved in oxidative phosphorylation, alongside reduction in absolute gene expression levels and cell size. Surprisingly, we found that a haploid human genome is compatible not only with the undifferentiated pluripotent state, but also with differentiated somatic fates representing all three embryonic germ layers, both in vitro and in vivo, despite a persistent dosage imbalance between the autosomes and X chromosome. Haploid human ES cells provide novel means for studying human functional genomics and development.

In one embodiment, the invention provides an enriched population of haploid human ES cells in culture, and a composition comprising an enriched population of haploid human ES cells, preferably in a culture medium.

The invention also provides a method for producing an enriched population of haploid human ES cells, the method comprising identifying haploid metaphases in a sample from a population of ES cells, wherein the ES cells are derived from an artificially activated human oocyte; and sorting the population of ES cells based on cell ploidy to produce an enriched population of haploid human ES cells. In some embodiments, the method further comprises maintaining the enriched population of ES cells in culture for at least three passages. Preferably, the haploid cells in the sample are identified by metaphase spread analysis or sorting of cells with less than 2 chromosomal copies. In some embodiments, the sorting step based on cell ploidy comprises at least one cycle of flow cytometry, preferably, fluorescence-activated cell sorting (FACS). Haploid cells can also be identified by flow cytometry, centromere protein immunofluorescence staining, or DNA fluorescence in situ hybridization (FISH).

Preferably, the enriched population comprises at least 5% haploid human ES cells.

In another aspect, the invention provides a substantially pure population of haploid human ES cells in culture, and a composition comprising a substantially pure population of haploid human ES cells, preferably in a culture medium.

A further aspect of the invention provides a method for producing a substantially pure population of haploid human ES cells, the method comprising identifying haploid metaphases in a sample from a population of ES cells, wherein the ES cells are derived from an artificially activated human oocyte; and sorting the population of ES cells based on cell ploidy using 2-5 cycles of FACS; thereby producing a substantially pure population of haploid human ES cells. Preferably, the haploid cells in the sample are identified by metaphase spread analysis or sorting of cells with less than 2 chromosomal copies. Haploid cells can also be identified by flow cytometry, centromere protein immunofluorescence staining, or DNA FISH.

Preferably, the substantially pure population comprises at least 95% haploid human ES cells.

The invention additionally provides a method for producing a haploid human ES cell line, the method comprising producing an enriched population of haploid human ES cells by a method of the invention; maintaining the enriched population of haploid human ES cells in culture; and sorting the ES cells in culture every three to four passages, wherein the sorting is based on cell ploidy; thereby producing a haploid human ES cell line.

The invention provides haploid human ES cell lines produced by the methods of the invention.

Further embodiments of the invention include a population of haploid multipotent human cells in culture and a composition comprising a population of haploid multipotent human cells.

Another embodiment of the invention is a method for producing a population of haploid multipotent human cells, the method comprising culturing haploid human embryonic stem cells under conditions for directed differentiation, thereby producing a population of haploid multipotent human cells.

In another aspect, the invention provides a method for producing a population of haploid multipotent human cells, the method comprising culturing haploid human ES cells under conditions to induce embryoid body formation; and dissociating the embryoid body into cells; thereby producing a population of haploid multipotent human cells. In some embodiments, the method further comprises sorting the dissociated cells based on cell surface markers. In some embodiments, the sorting comprises FACS.

Preferably, the population of haploid multipotent human cells is a substantially pure population. In one embodiment, the population of haploid multipotent human cells comprises endodermal progenitor cells. In one embodiment, the population of haploid multipotent human cells comprises mesodermal progenitor cells. In one embodiment, the population of haploid multipotent human cells comprises ectodermal progenitor cells. In one embodiment, the population of haploid multipotent human cells comprises neural progenitor cells.

The invention provides a population of haploid differentiated human somatic cells in culture, and a composition comprising a population of haploid differentiated human somatic cells. The invention also provides a method for producing a population of haploid differentiated human somatic cells, the method comprising culturing haploid human ES cells under conditions for directed differentiation, thereby producing a population of haploid differentiated human somatic cells. The invention further provides a method for producing a population of haploid differentiated human somatic cells, the method comprising injecting haploid human ES cells into a non-human mammal under conditions to induce teratoma formation; and dissociating the teratoma into cells; thereby producing a population of haploid multipotent human cells.

Preferably, the haploid differentiated human somatic cells are selected from the group consisting of neurons, cardiomyocytes, pancreatic cells, skin cells, muscle cells, kidney cells, liver cells, lung cells, and intestinal cells.

A further aspect of the invention is a method of genetic screening, the method comprising exposing an enriched population of human haploid ES cells to a mutagen to induce at least one mutation in the cells; selecting human haploid ES cells in the enriched population that contain the mutation; and identifying a genotypic and/or phenotypic effect of the mutation in the human haploid ES cells. In one embodiment, the genetic screening is a forward genetic screen. In one embodiment, the mutagen is selected from the group consisting of a physical mutagen, a chemical mutagen, and a biological agent. Preferably, the mutagen is a biological agent, more preferably, a vector.

In a further aspect the present invention provides a population of genetically-modified human haploid ES cells. Similarly, in another aspect the present invention provides a population of genetically-modified human haploid multipotent cells. In yet another aspect the present invention provides a population of genetically-modified or human haploid differentiated somatic cells. In each of such embodiments the genetically-modified human haploid cells (i.e. ES cells, multipotent cells, or differentiated somatic cells) contain at least one artificially-introduced mutation. In another aspect the present invention provides a library of such genetically-modified human haploid cells (i.e. a library of genetically-modified ES cells, multipotent cells, or differentiated somatic cells), such as, for example, a gene trap library, wherein the library comprises multiple different artificially-introduced mutations. In each of the embodiments involving genetically-modified human haploid cells, the mutations may be introduced by treatment of human haploid cells with a mutagen selected from the group consisting of a physical mutagen, a chemical mutagen, and a biological agent. Similarly, in each of these embodiments, the genetically-modified haploid cells may optionally also comprise one or more marker or reporter genes, for example associated with the artificially-introduced mutation.

BRIEF DESCRIPTION OF THE DRAWINGS/FIGURES

This patent or application file contains at least one drawing executed in color. Copies of this patent or patent application publication with color drawing(s) will be provided by the Office upon request and payment of the necessary fee.

Figure 1B:
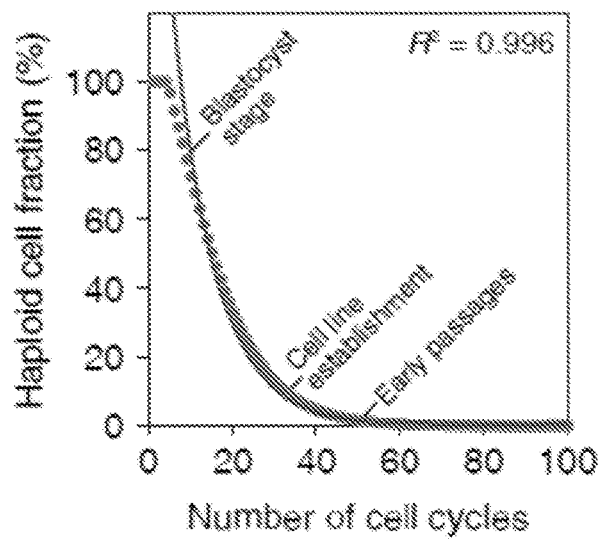
Figure 1C:
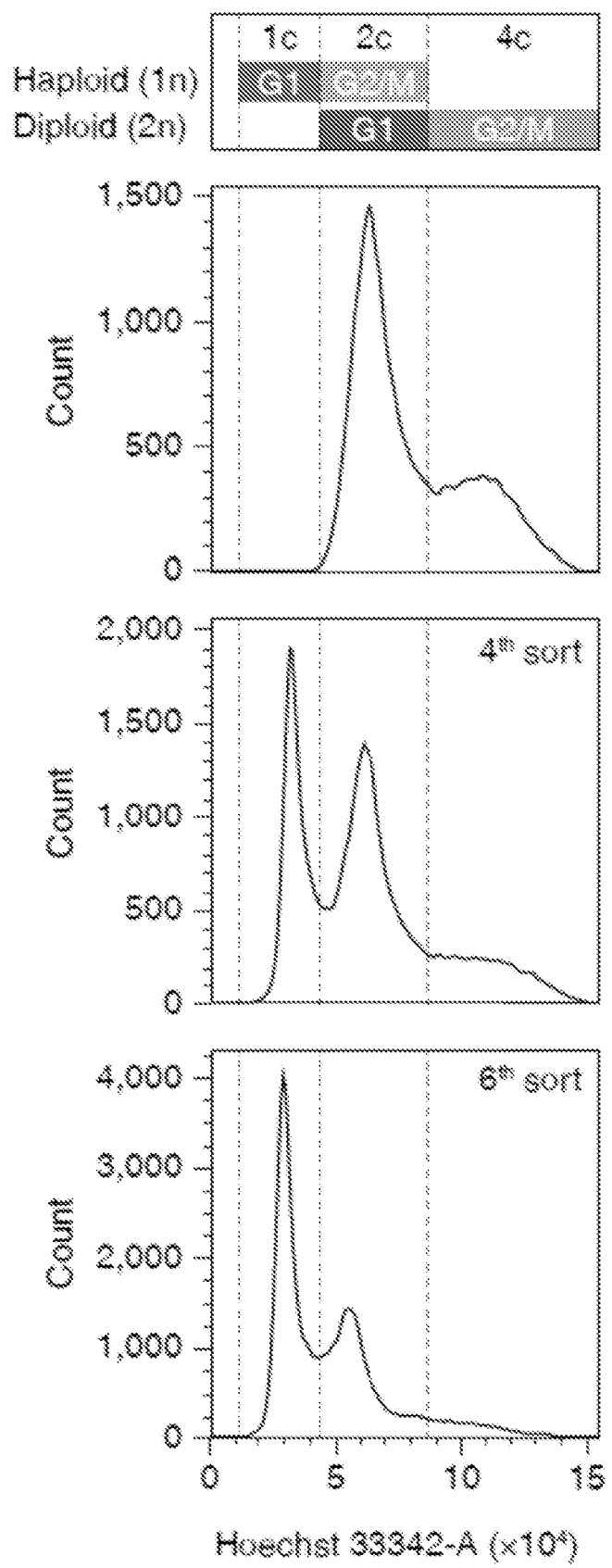
Figure 1D:
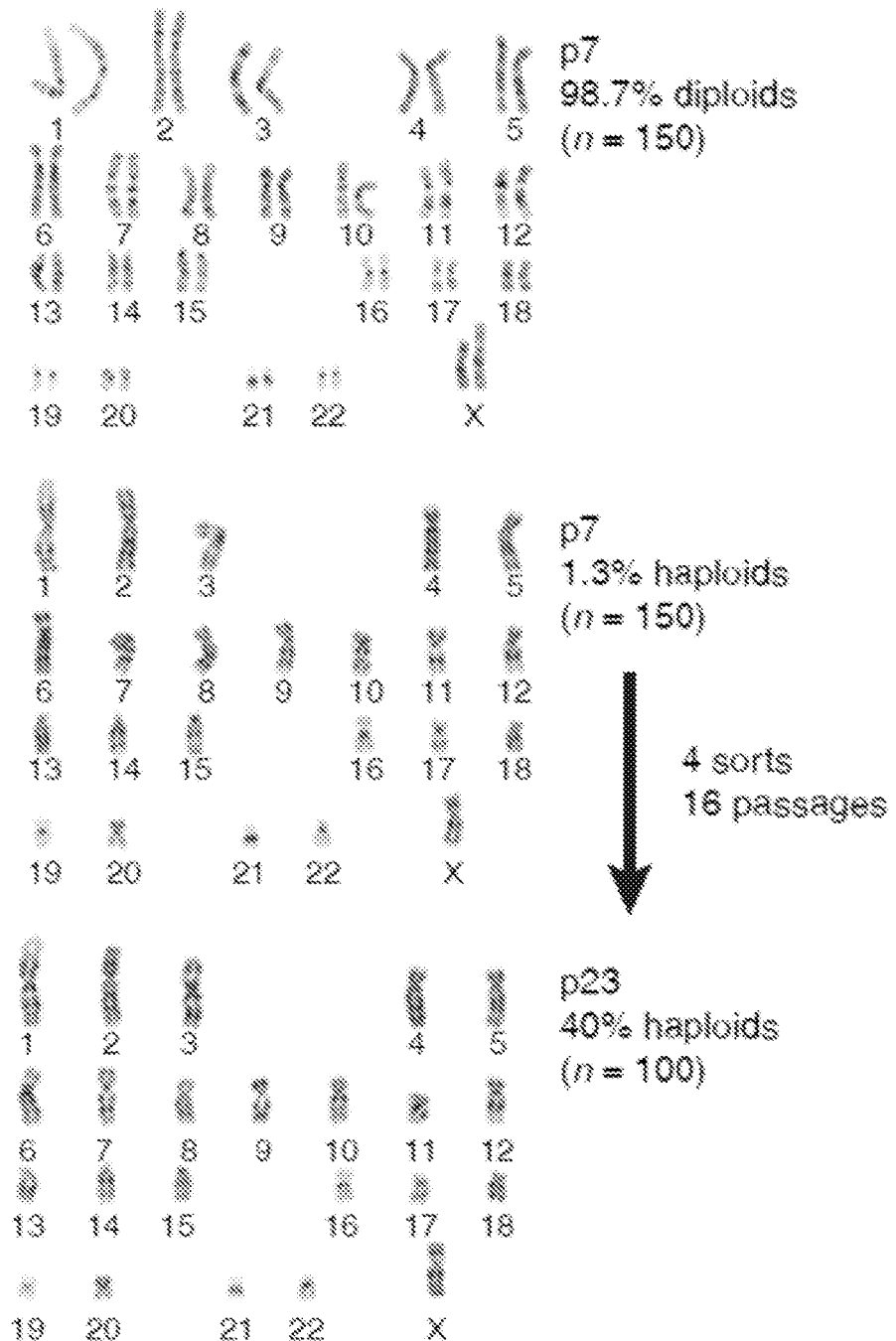
Figure 1E:
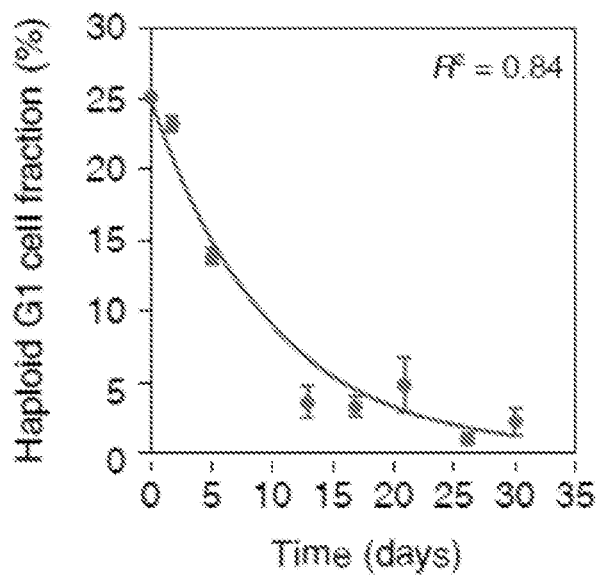
Figures 1F, 1G:
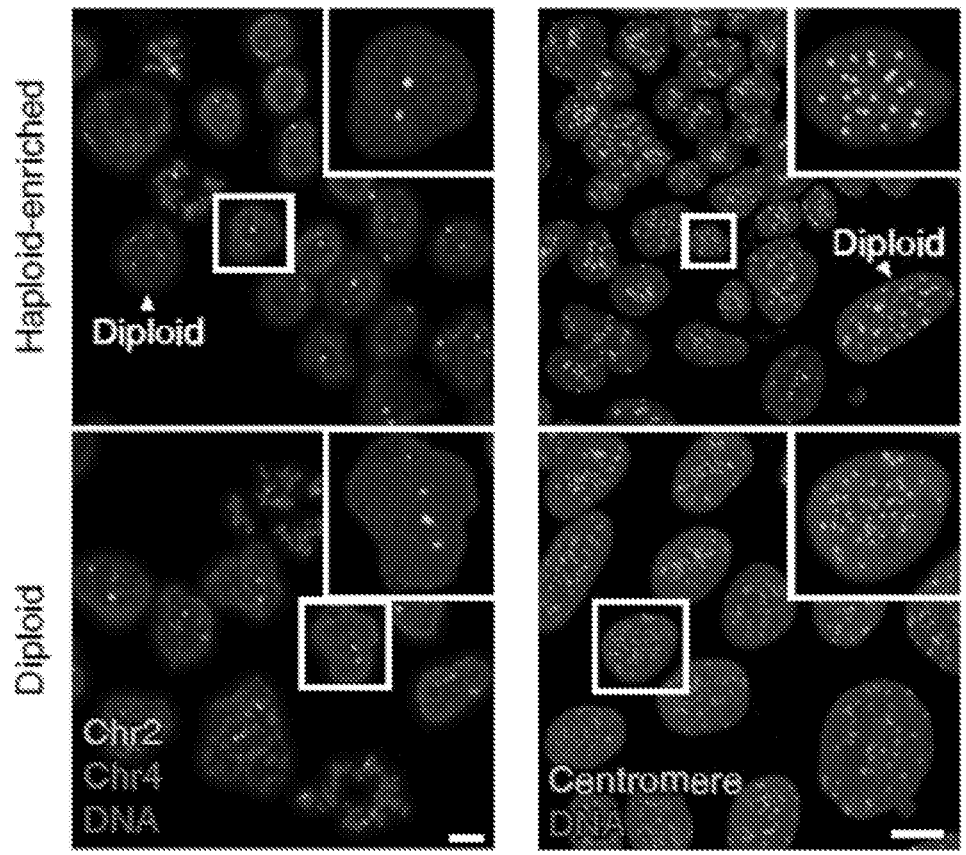

FIG. 1a-1g show derivation of haploid human ES cell lines. FIG. 1a shows a schematic outline of parthenogenetic oocyte activation and potential haploidy in resulting ES cell lines. Second polar body (PB) extrusion at MII without fertilization results in a haploid 1-cell stage embryo and haploid cells are gradually eliminated due to diploidization. FIG. 1b shows a diploidization rate model for a haploid egg with a theoretical diploidization probability of 10%, overlaid with an exponential decay fit (red curve). Approximated cell cycle numbers for different ES cell line derivation stages is indicated. FIG. 1c shows establishment of the haploid-enriched human ES cell line h-pES10 after repeated sorting and enrichment of 1c-cells. c: chromosomal copies. From top to bottom: DNA content profiles of unsorted diploid cells, partially purified haploid cells at the fourth sort, and mostly purified haploid cells at the sixth sort. FIG. 1d shows diploid and haploid karyotypes of pES10 before and after 4 rounds of haploid cell enrichment and expansion. FIG. 1e shows diploidization dynamics of h-pES10 over seven passages by flow cytometry, overlaid with an exponential fit to the data (red curve). Error bars show standard deviation (s.d.). FIG. 1f shows DNA FISH and FIG. 1g shows centromere staining in haploid-enriched and unsorted diploid pES10 cells. Magnified insets show representative haploid and diploid nuclei with either single or double hybridization signals (FIG. 1f) and 23 or 46 centromeres (FIG. 1g), respectively. White arrows point to diploid nuclei. Scale bars=10 µm.

Figure 2A:
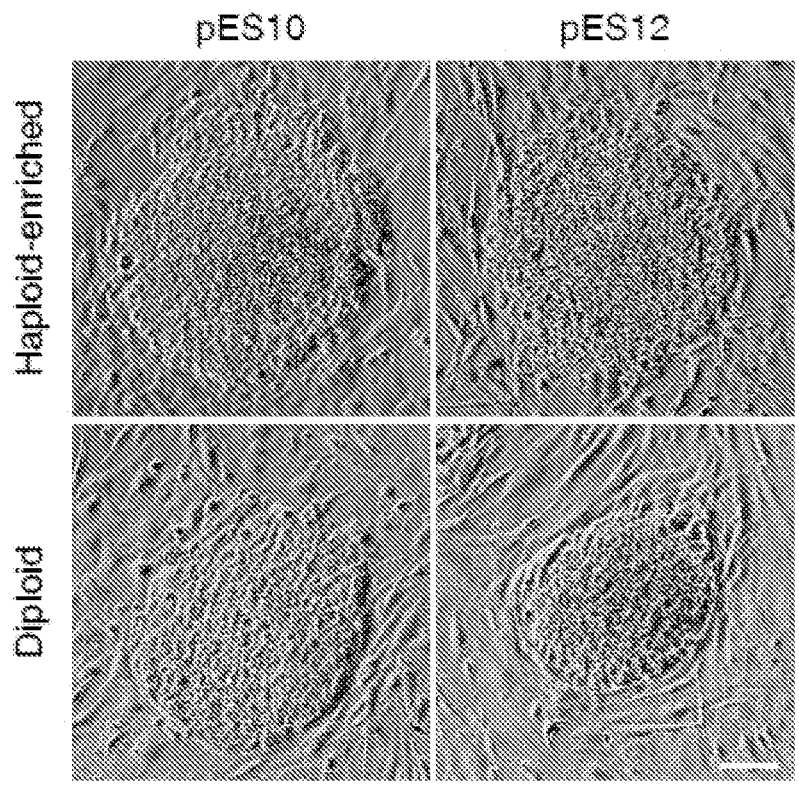
Figure 2B:
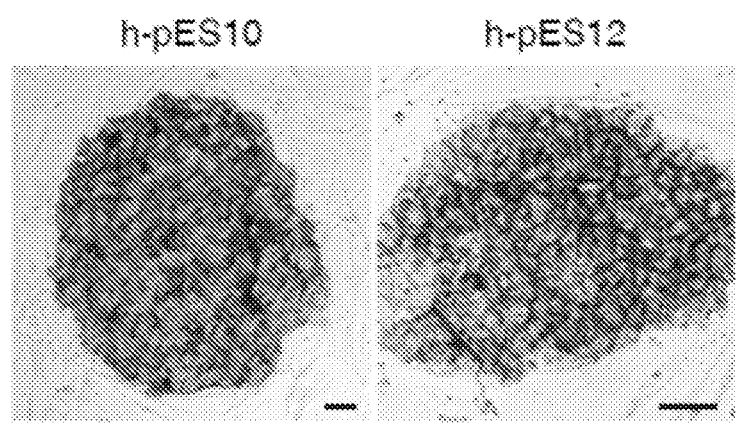
Figure 2C:
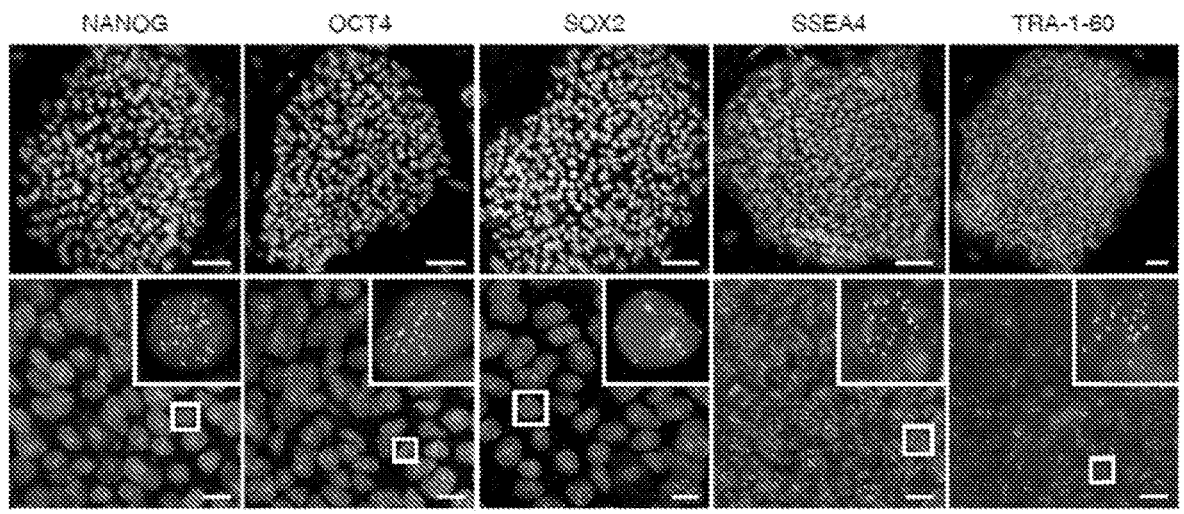
Figure 2D:
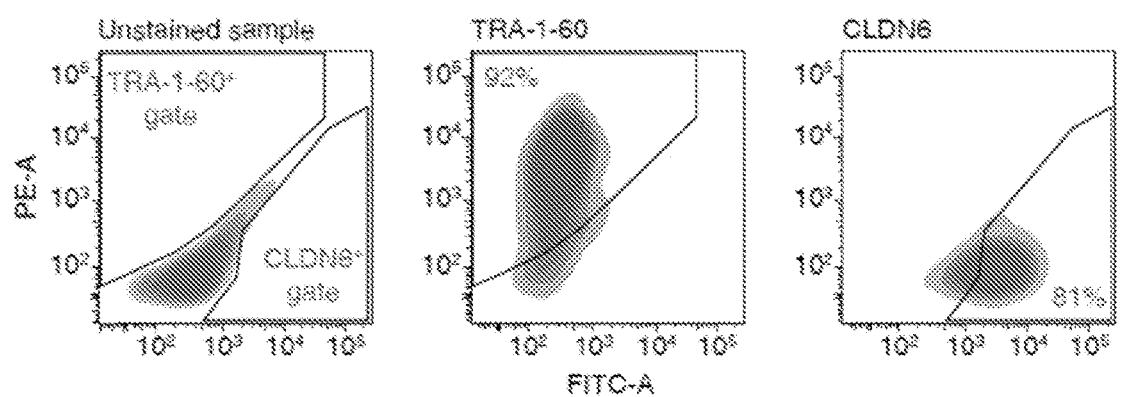
Figure 2E:
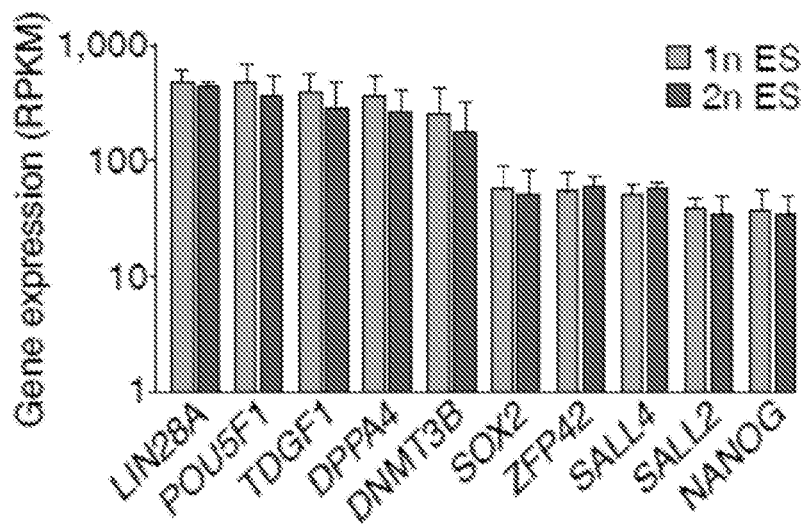
Figure 2F:
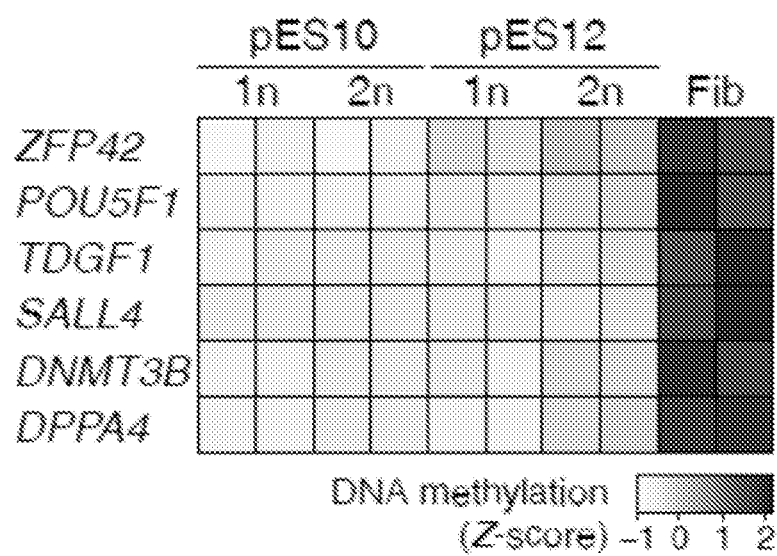
Figure 2G:
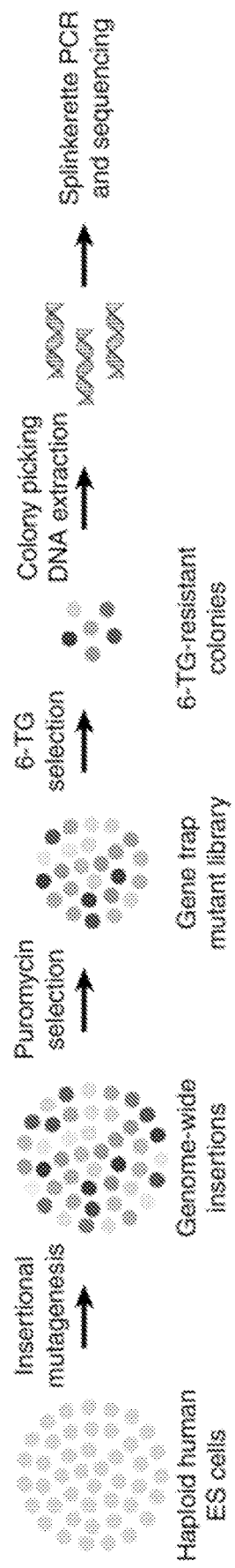
Figure 2H:
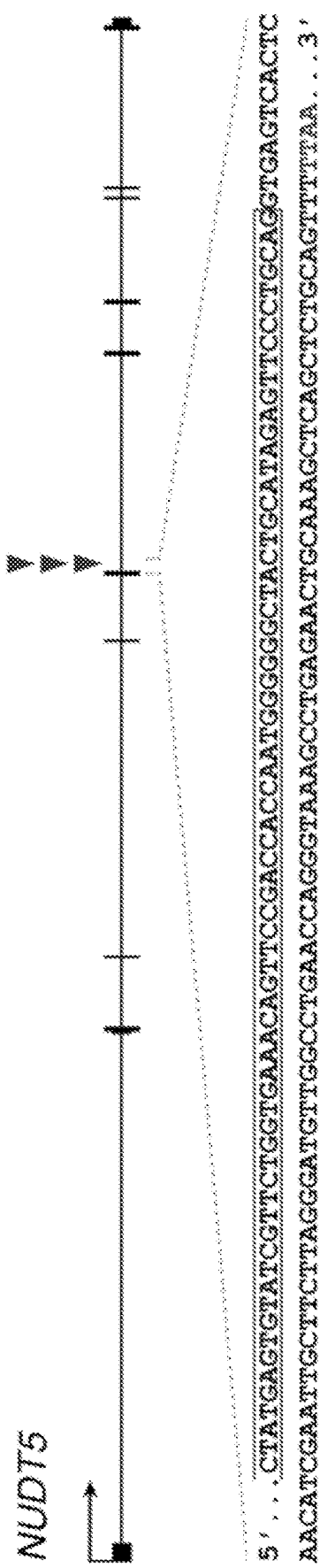
Figure 2I:
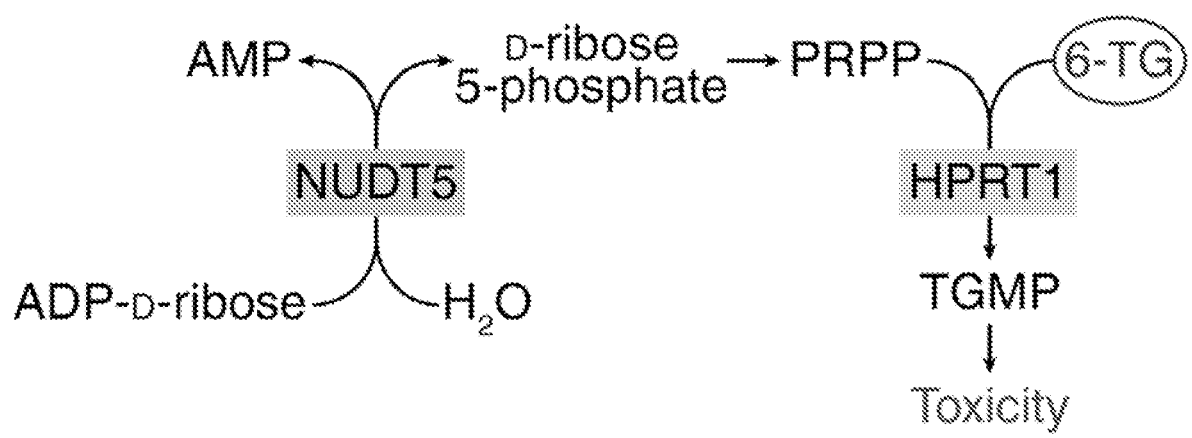

FIG. 2a-2i show that haploid human ES cells display classical characteristics of pluripotent stem cells and enable loss-of-function genetic screening. FIG. 2a shows colony morphology of haploid-enriched and matching diploid cell lines. Scale bar is 50 µm. FIG. 2b shows alkaline phosphatase staining of h-pES10 and h-pES12. Scale bars=50 µm. FIG. 2c shows co-staining of pluripotency markers (red), centromeres (green) and DNA (blue) in h-pES10 at colony resolution (upper panel; scale bars=50 µm) and single-cell resolution (lower panel; scale bars=10 µm). Magnified insets show representative haploid cells with 23 centromeres. FIG. 2d shows flow cytometry analysis of h-pES10 by co-staining DNA and cell surface markers TRA-1-60 and CLDN6, after gating for haploid cells in G1. FIG. 2e shows mean expression levels±s.d. of pluripotency genes in haploid (1n) and diploid (2n) pES10 and pES12 cells in G1 (n=4 for each group, with two biological replicates for each cell line, logarithmic scale). RPKM: reads per kilobase per million fragments mapped. FIG. 2f shows DNA methylation levels at pluripotency genes in duplicates of haploid (1n) and diploid (2n) pES10 and pES12 cells in G1, as well as control fibroblasts (Fib). FIG. 2g shows a schematic overview of genome-wide gene trapping in haploid human ES cells and screening for 6-TG-resistance genes. FIG. 2h shows NUDT5 insertions (red arrows) detected in 3 6-TG-resistant colonies. Upper panel shows gene structure. Lower panel shows genomic sequence of the intronic insertion site (indicated by TTAA) and upstream exonic sequence (in box). FIG. 2i shows a schematic of the metabolic pathway leading to 6-TG toxicity through NUDT5-mediated PRPP production. ADP: adenosine diphosphate; AMP: adenosine monophosphate.

Figure 3A:
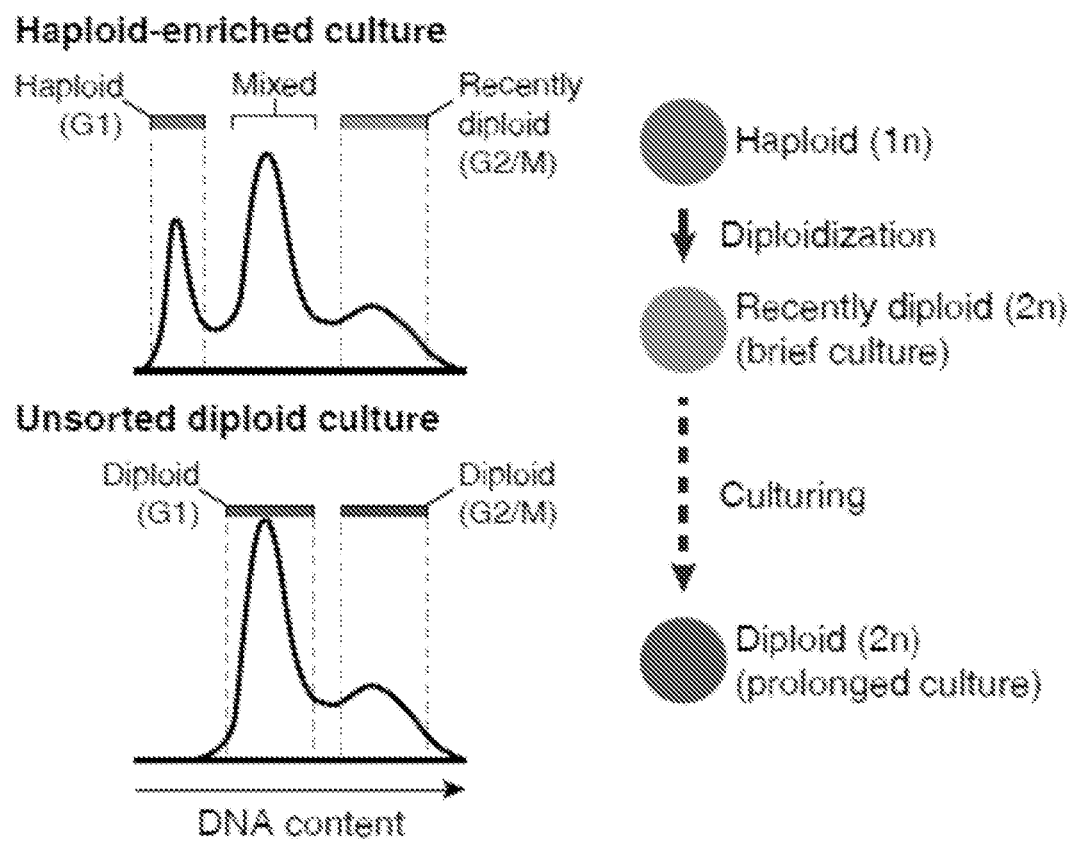
Figure 3B:
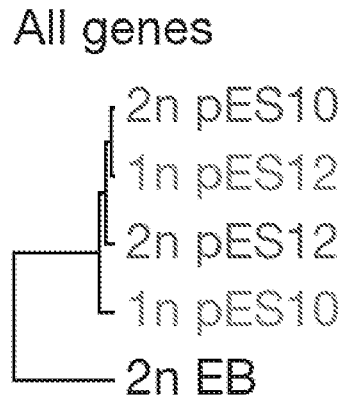
Figure 3C:
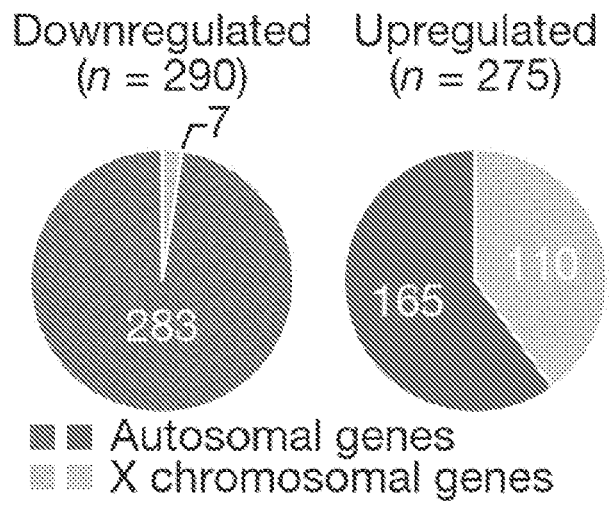
Figure 3D:
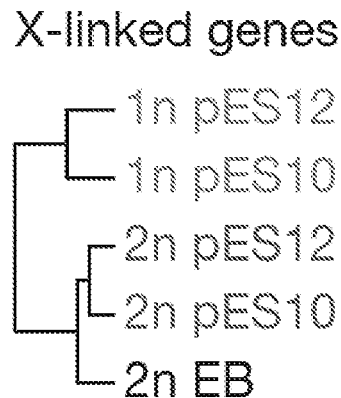
Figure 3E:
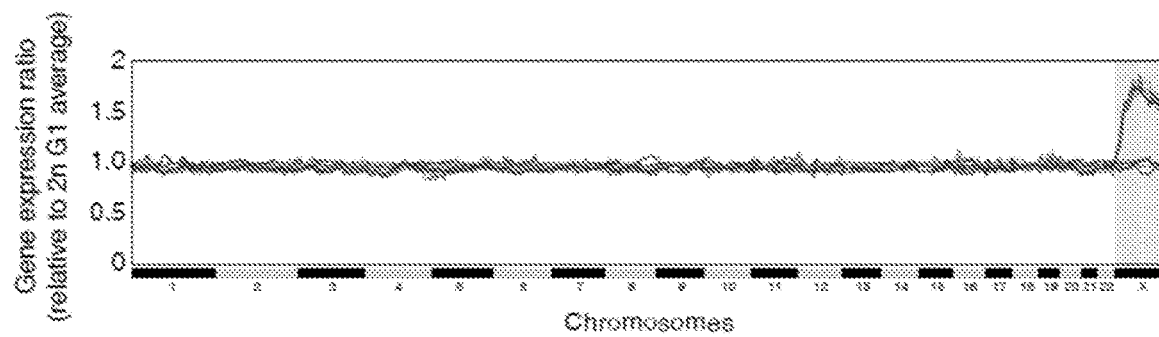
Figure 3F:
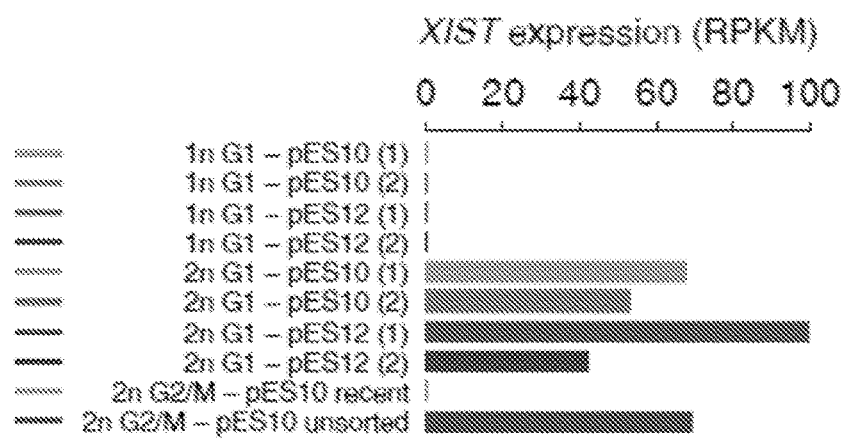
Figure 3G:
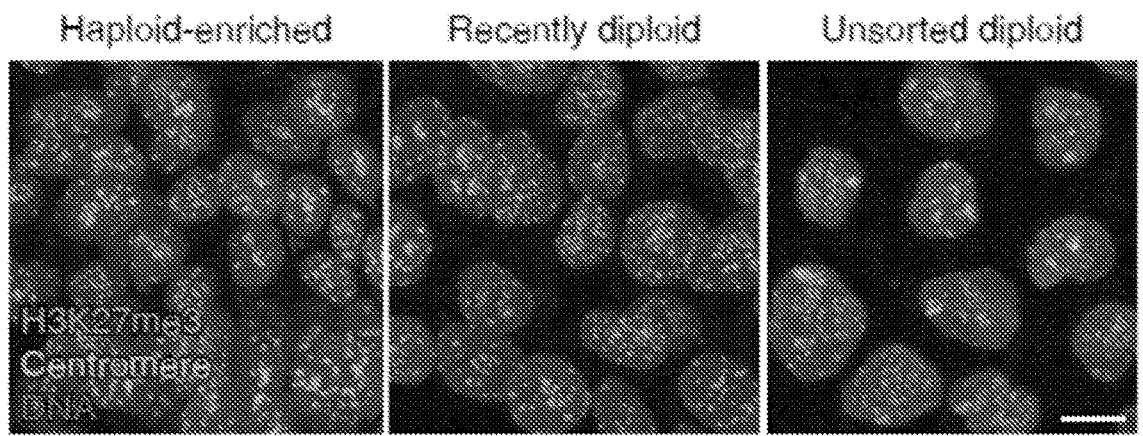
Figure 3H:
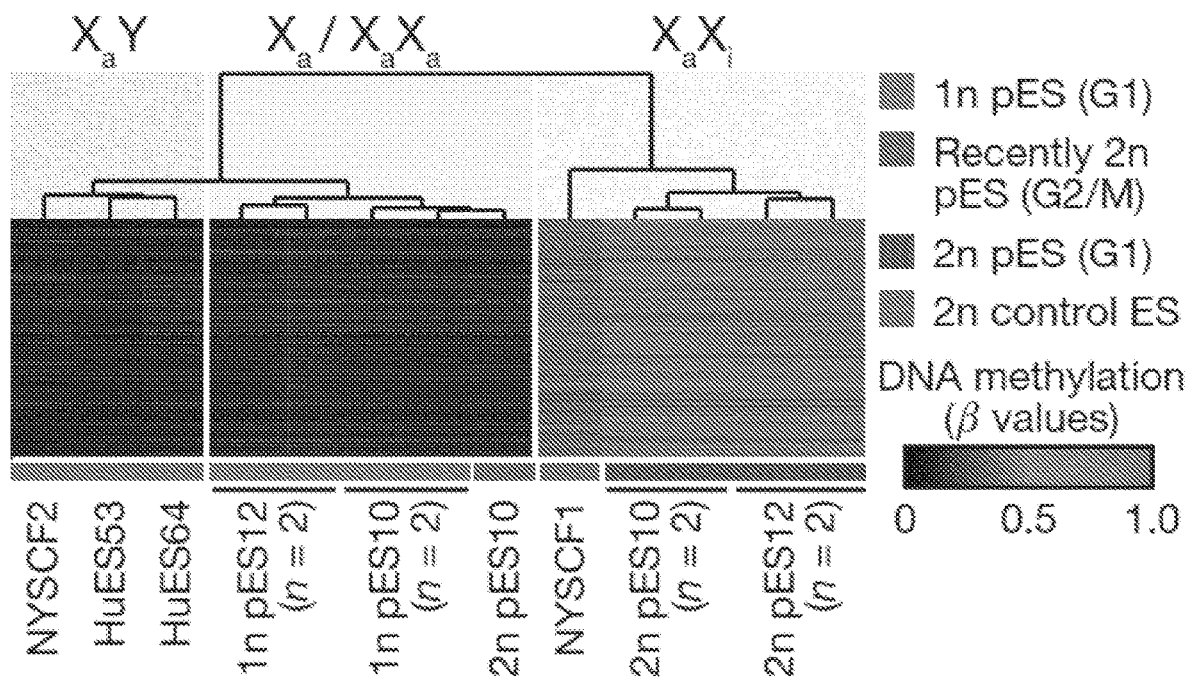
Figure 3I:
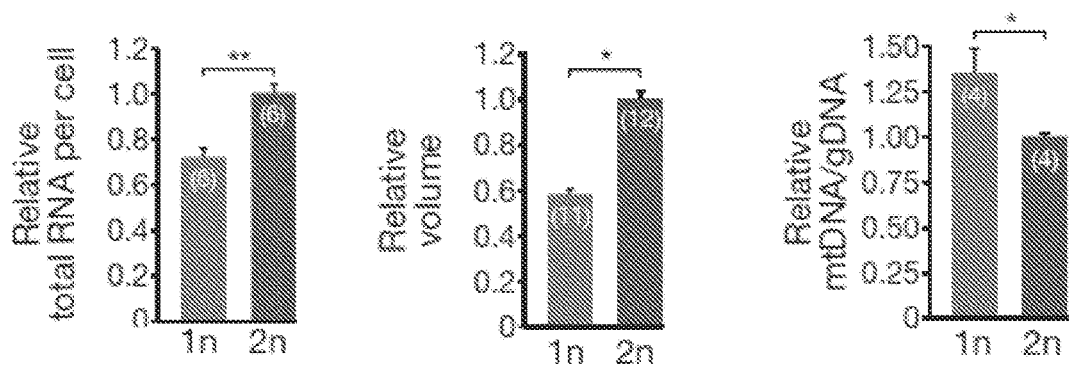
Figure 3J:
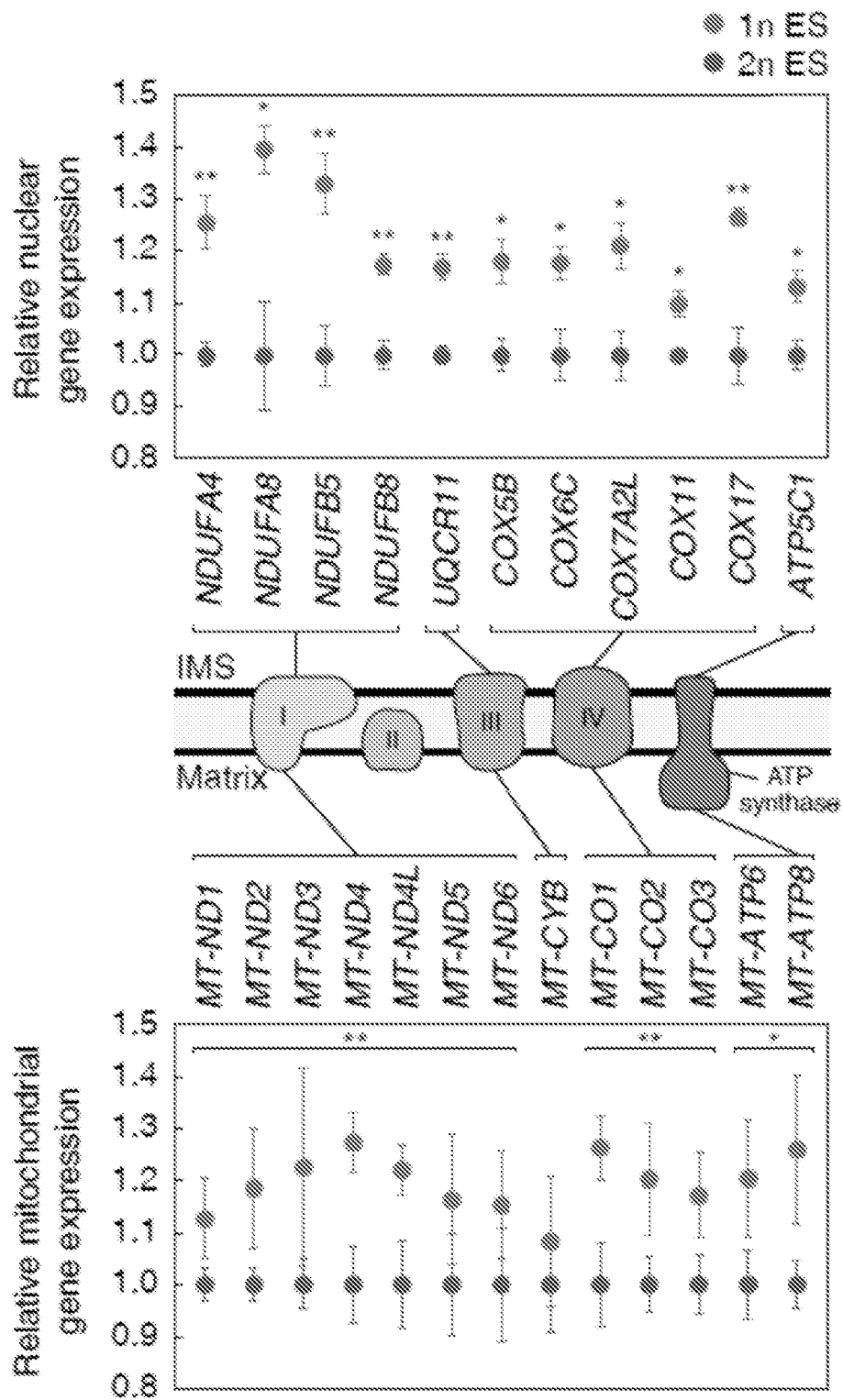

FIG. 3a-3j show molecular and cellular comparisons of haploid and diploid ES cells. FIG. 3a shows an experimental scheme of haploid and diploid ES cell isolation for comparative analyses. FIG. 3b shows RNA-Seq-based hierarchical clustering analysis of isogenic haploid (1n) and diploid (2n) cells in G1 (two biological replicates per cell line), compared with a 2n pES12-derived embryoid body (EB) sample. FIG. 3c shows a pie chart representation of relatively downregulated and upregulated genes in haploid vs. diploid ES cells on autosomes and X chromosome. FIG. 3d shows hierarchical clustering analysis by X chromosomal genes. FIG. 3e-3h show differential X chromosome inactivation (XCI) status in haploid and diploid ES cells. FIG. 3e shows genome-wide gene expression moving median plot (relative to the average of diploids in G1 by RNA-Seq, window size=100 genes). FIG. 3f shows XIST expression levels. (1) and (2) denote biological replicates. FIG. 3g shows H3K27me3 staining. Scale bar=10 µm. FIG. 3h shows DNA methylation levels on the X chromosome. FIG. 3i shows relative total RNA, cell volume and ratio of mitochondrial DNA (mtDNA) to genomic DNA (gDNA) between G1-sorted haploid and diploid ES cells. Numbers of replicates are indicated in parenthesis. Error bars represent s.d. FIG. 3j shows mean expression levels±standard error of the mean (s.e.m.) of nuclear (top panel) and mitochondrial oxidative phosphorylation genes (lower panel), upregulated in haploid ES cells relative to diploid ES cells (n=4 for each group, as in FIG. 2e), and schematic representation of their organization in this pathway. IMS: intermembrane space. *P<0.05; **P<0.01 (two-tailed unpaired Student's t test).

Figure 4A:
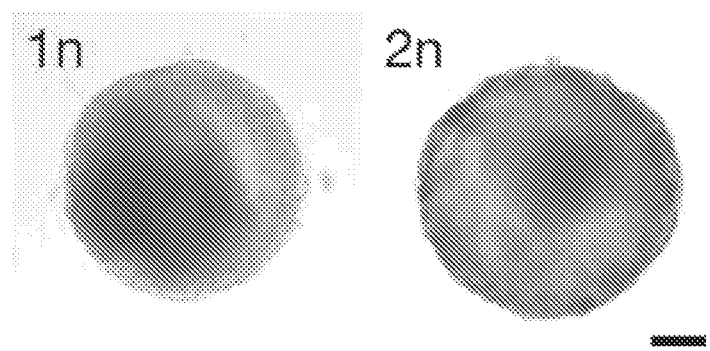
Figure 4B:
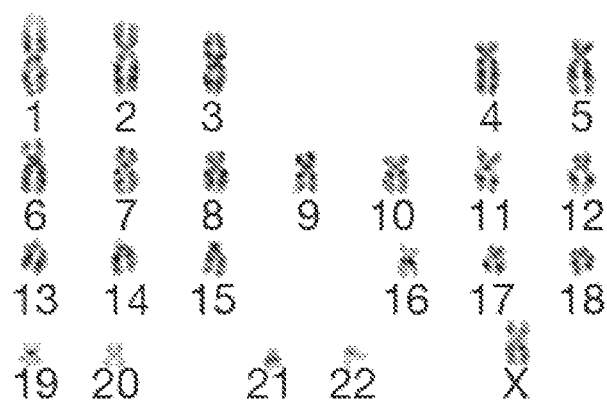
Figure 4C:
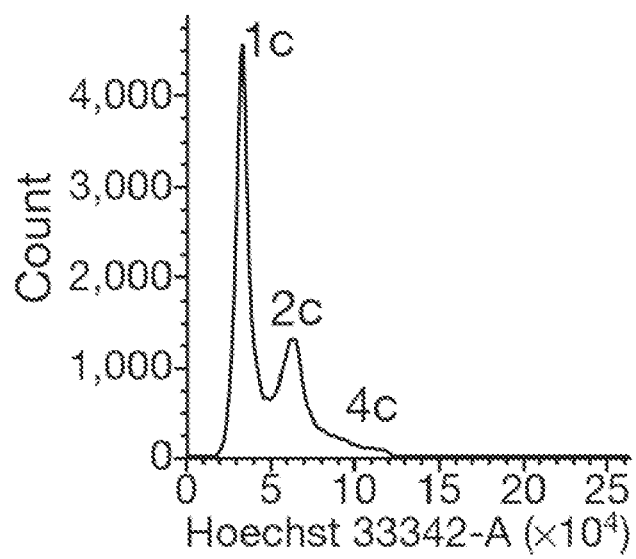
Figure 4D:
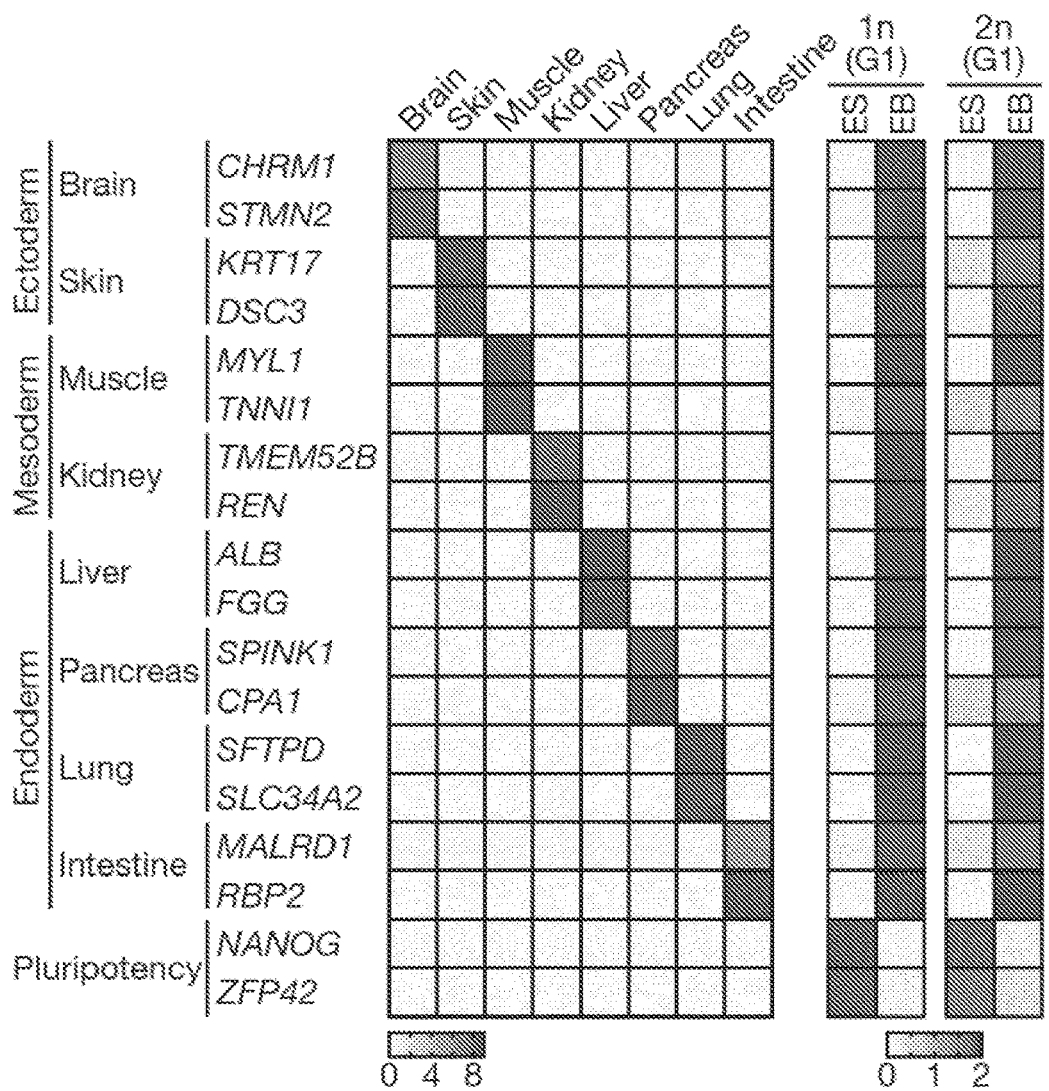
Figure 4E:
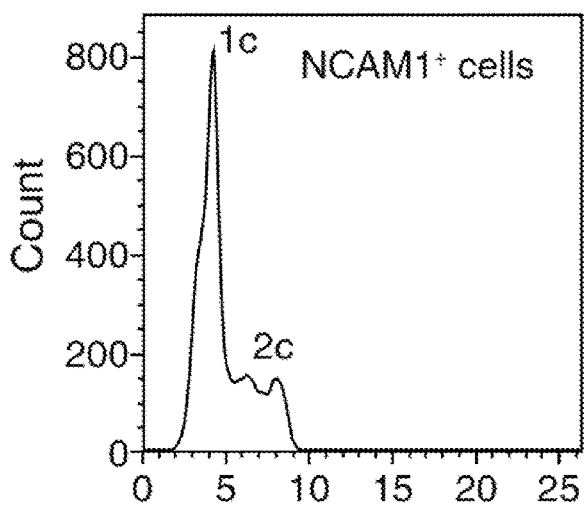
Figure 4F:
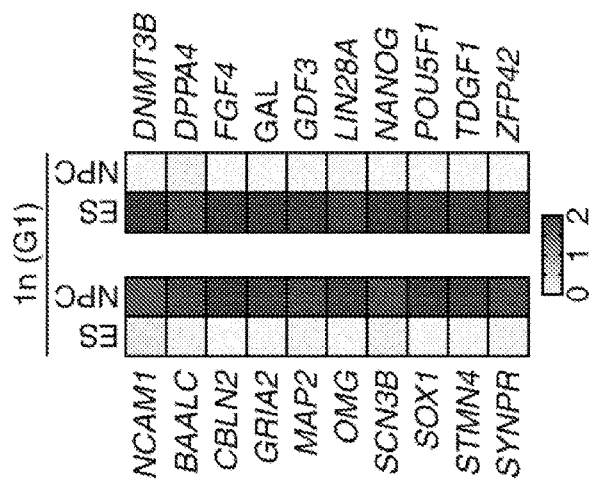
Figure 4G:
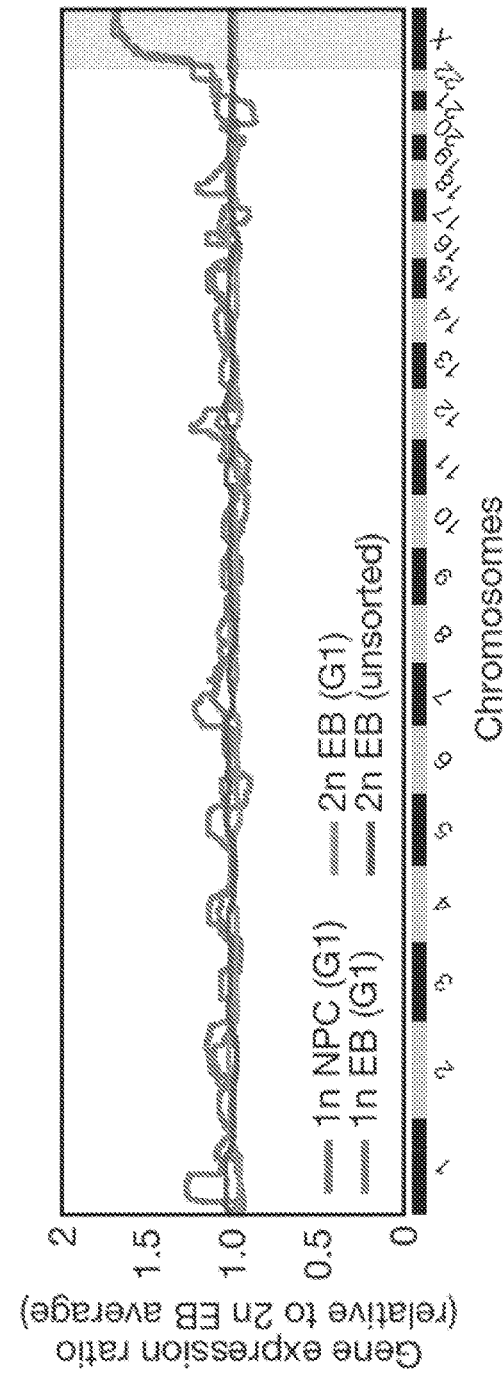
Figure 4H:
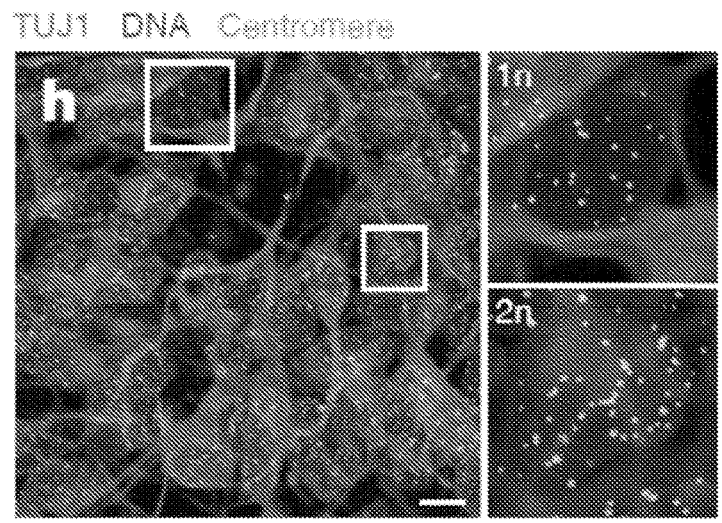
Figure 4I:
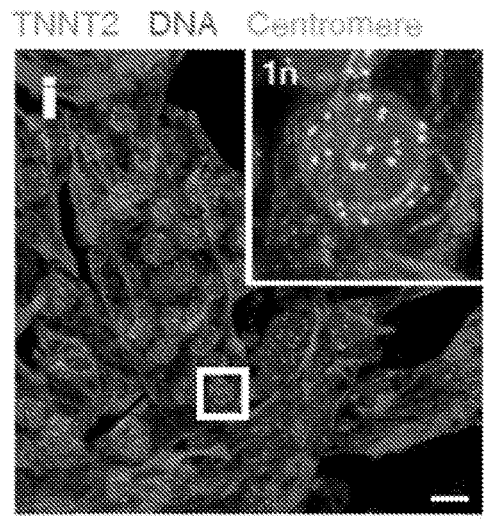
Figure 4J:
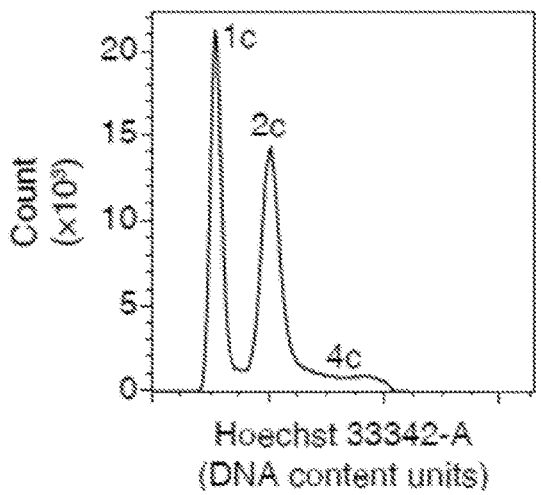
Figure 4K:
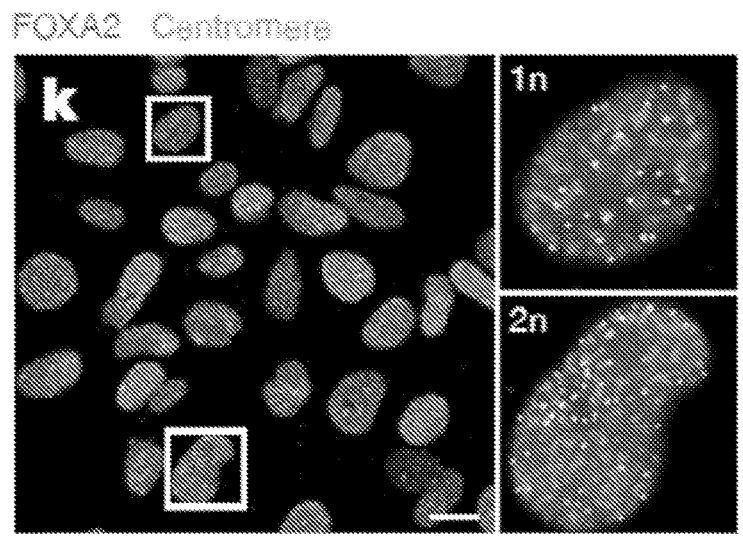
Figure 4L:
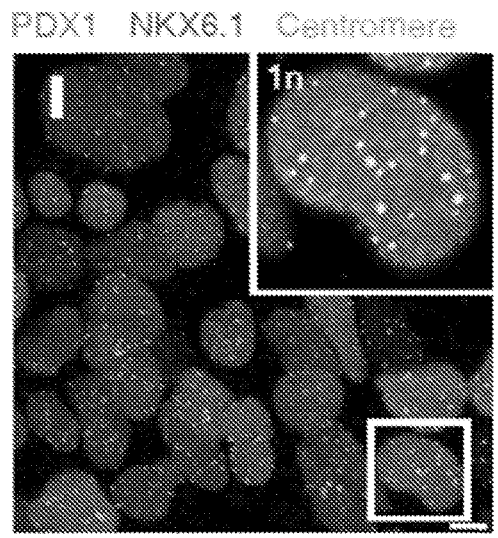
Figure 4M:
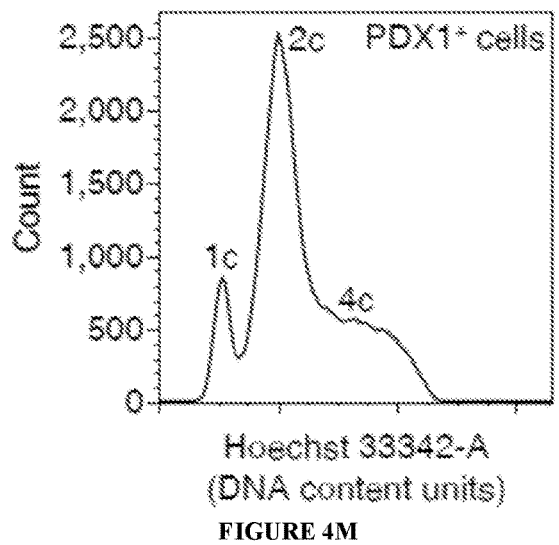
Figure 4N:
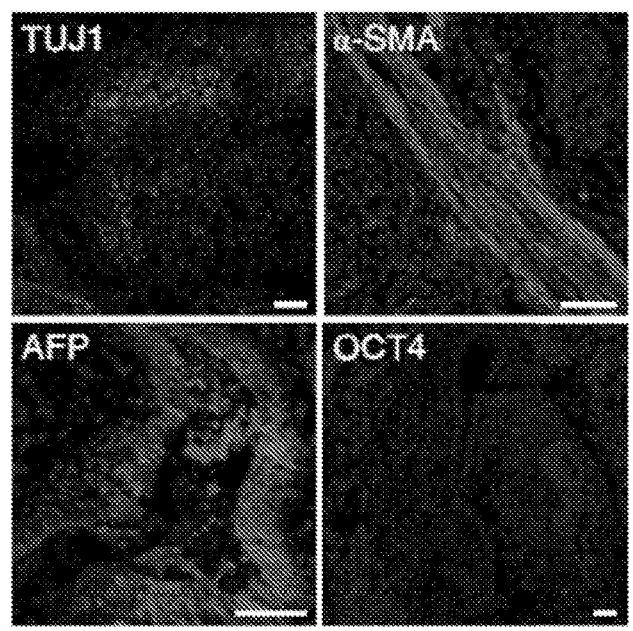
Figure 4O:
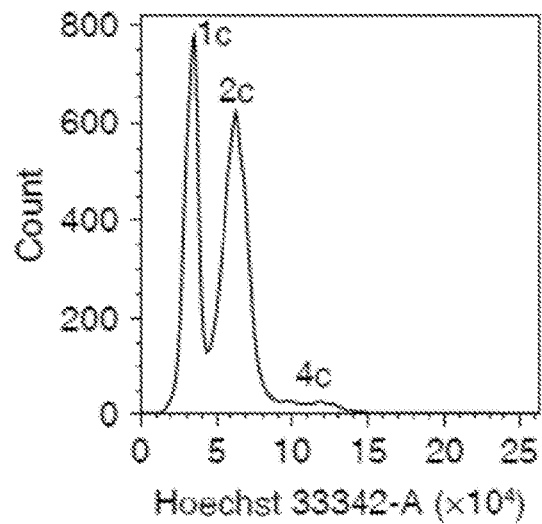
Figure 4P:
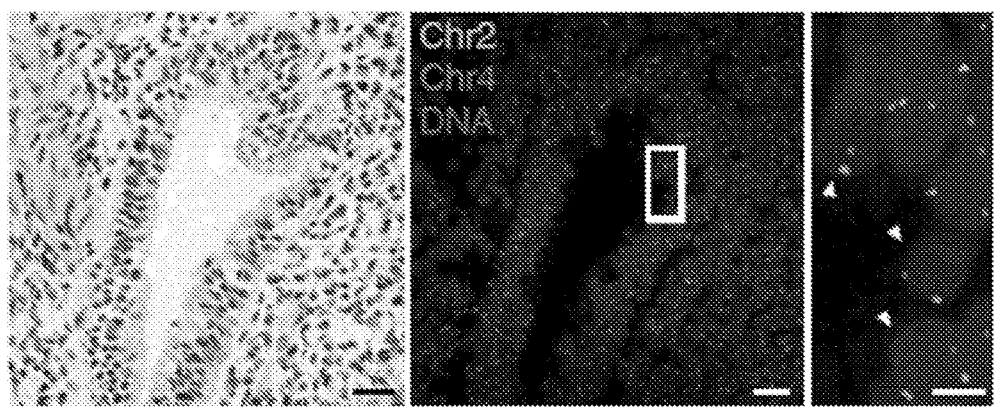

FIG. 4a-4p show the differentiation potential of haploid human cells. FIG. 4a shows representative images of 21-day EBs from haploid-enriched and diploid pES12 cells. Scale bar=100 µm. FIG. 4b shows haploid karyotype of cells dissociated from haploid-enriched EBs in FIG. 4a (plated cells shown in FIG. 10a). FIG. 4c shows the DNA content profile of h-pES10 EB cells. FIG. 4d shows expression of tissue- and pluripotency-specific genes in G1-sorted haploid (1n) and diploid (2n) ES and EB pES10 cells). FIG. 4e shows the DNA content profile of NCAM1-positive h-pES10-derived neural progenitor cells (NPCs). FIG. 4f shows expression of neural- and pluripotency-specific genes (right and left panels, respectively) in G1-sorted haploid pES10 ES cells and NPCs. Color-coded scale shows expression relative to the mean across the NPC sample and an ES cell duplicate. FIG. 4g shows differential XCI status in haploid and diploid pES10-derived EBs and NPCs, as shown by genome-wide gene expression moving median plot (window size=200 genes). Centromere and differentiation marker co-staining is shown in h-pES12-derived TUJ1-positive neurons (FIG. 4h), TNNT2-positive cardiomyocytes (FIG. 4i), FOXA2-positive definitive endoderm cells (FIG. 4k) and PDX1-positive and NKX6.1-positive PPCs (FIG. 4l). Magnified insets show representative haploid and diploid nuclei. Scale bars=10 µm. DNA content profiles are shown for h-pES12 cells differentiated into cardiomyocytes (FIG. 4j) and PDX1-positive PPCs (FIG. 4m). FIG. 4n shows TUJ1 (ectoderm), α-SMA (mesoderm), AFP (endoderm) and OCT4 (pluripotency) staining in an h-pES12-derived teratoma. Scale bars=50 µm. FIG. 4o shows DNA content profile of an h-pES10-derived teratoma. FIG. 4p shows serial h-pES12-derived teratoma sections analyzed by histology with hematoxylin and eosin staining (left panel; scale bar=20 µm) and DNA FISH (right panel; scale bar=20 µm). Magnified inset shows representative haploid nuclei (scale bar=5 µm).

Figure 5C:
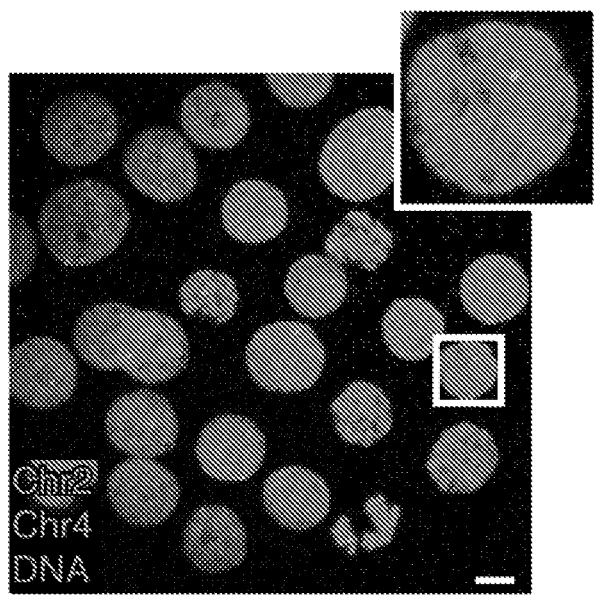
Figure 5D:
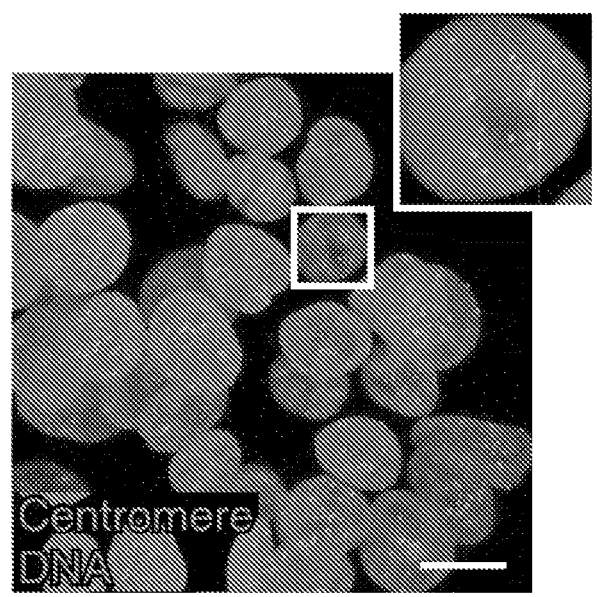
Figure 5E:
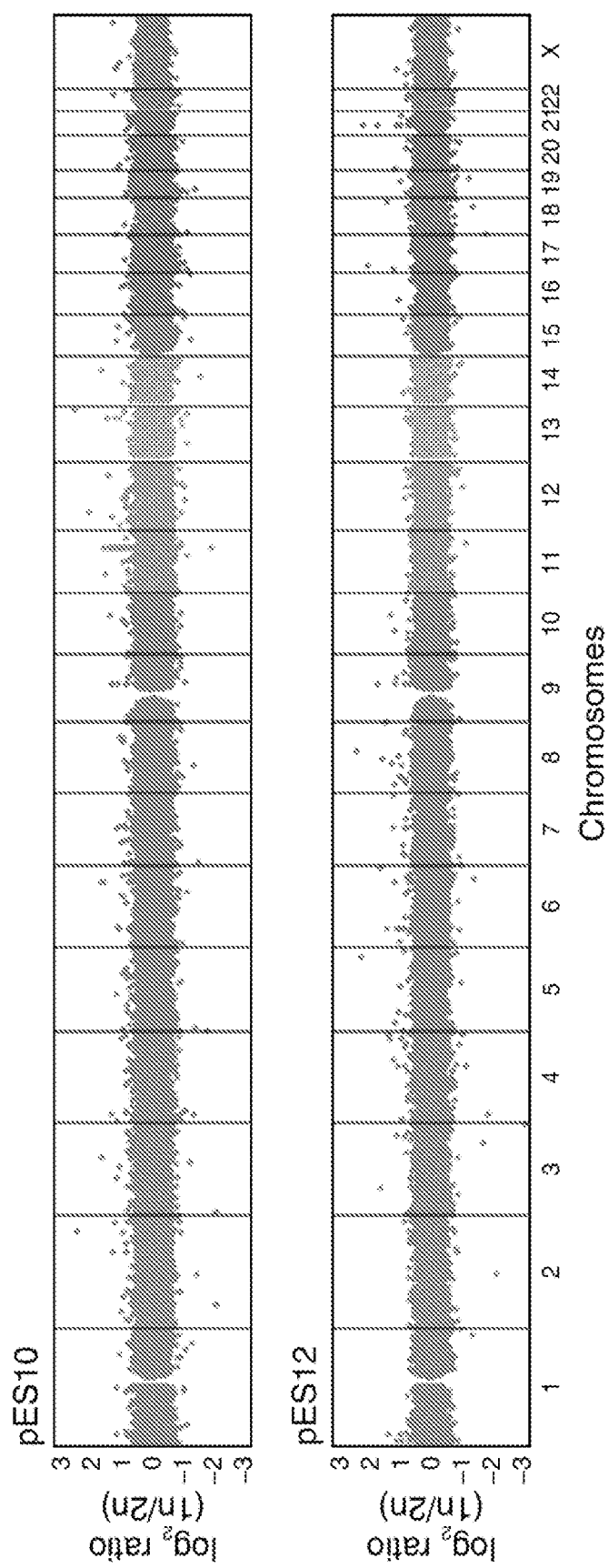

FIG. 5a-5e show derivation of haploid human ES cell line h-pES12. FIG. 5a shows establishment of a haploid-enriched human ES cell line from pES12 cells after repeated sorting and enrichment of 1c-cells using Hoechst 33342 staining. Shown from top to bottom are the DNA content profiles of unsorted diploid cells, partially purified haploid cells at the third sort, and mostly purified haploid cells at the fifth sort. c: chromosomal copies. FIG. 5b shows karyotypes and haploid metaphase percentage over the course of enrichment and passaging. FIG. 5c shows DNA FISH and FIG. 5d shows centromere protein immunofluorescence staining in h-pES12. Magnified insets show representative haploid nuclei with single hybridization signals (FIG. 5c) and 23 centromeres (FIG. 5d), respectively. Scale bars=10 µm. FIG. 5e shows single nucleotide polymorphism (SNP) array-based copy number variation (CNV) analysis comparing haploid (1n) pES10 and pES12 cells to their unsorted diploid (2n) counterparts (logarithmic scale).

Figure 6A:
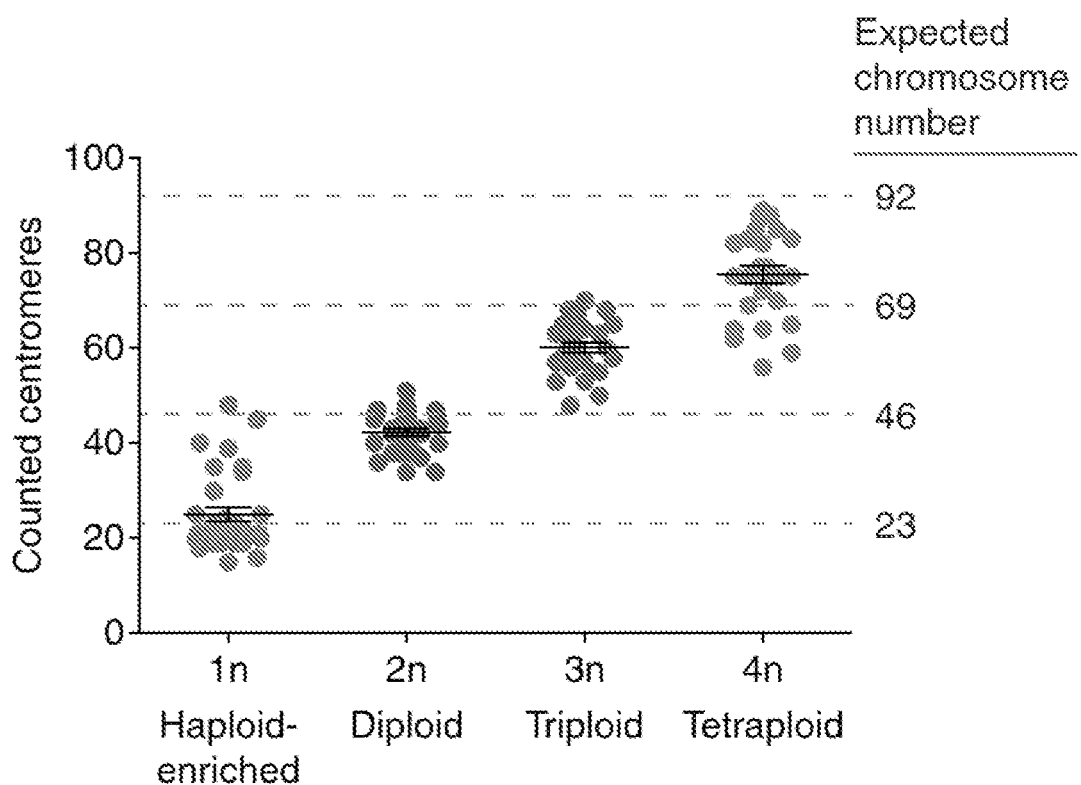
Figure 6B:
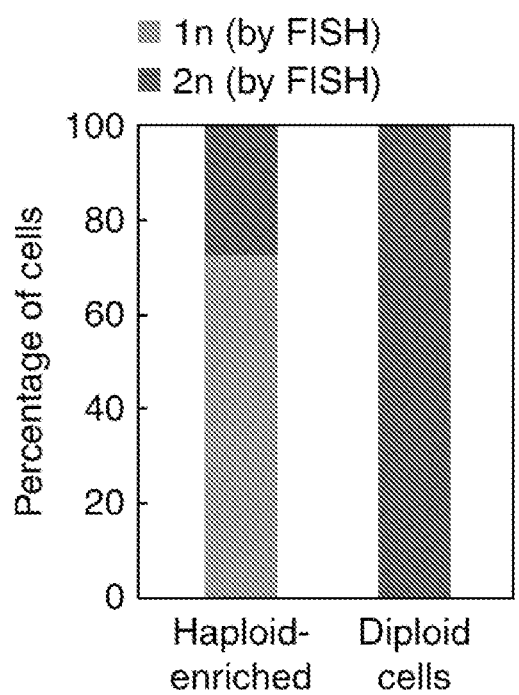
Figure 6C:
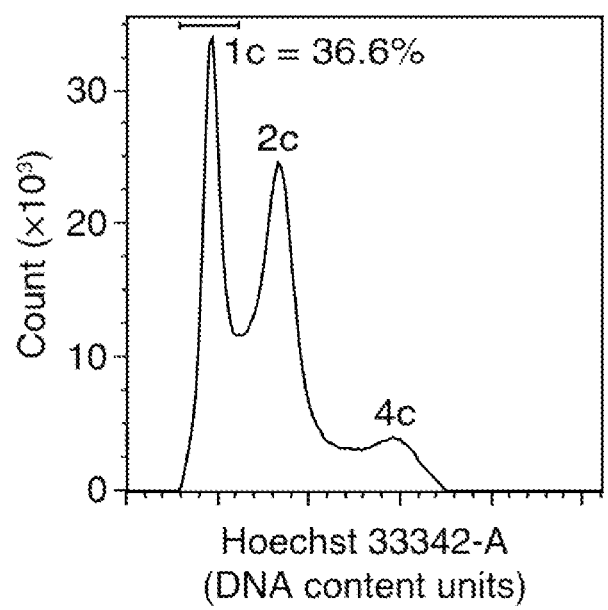
Figure 6D:
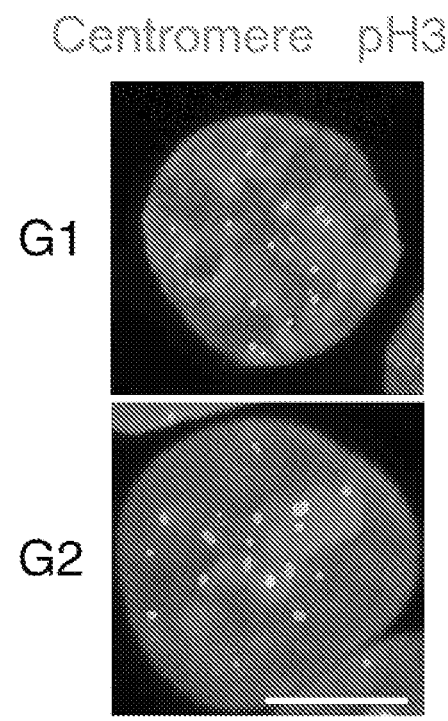
Figure 6E:
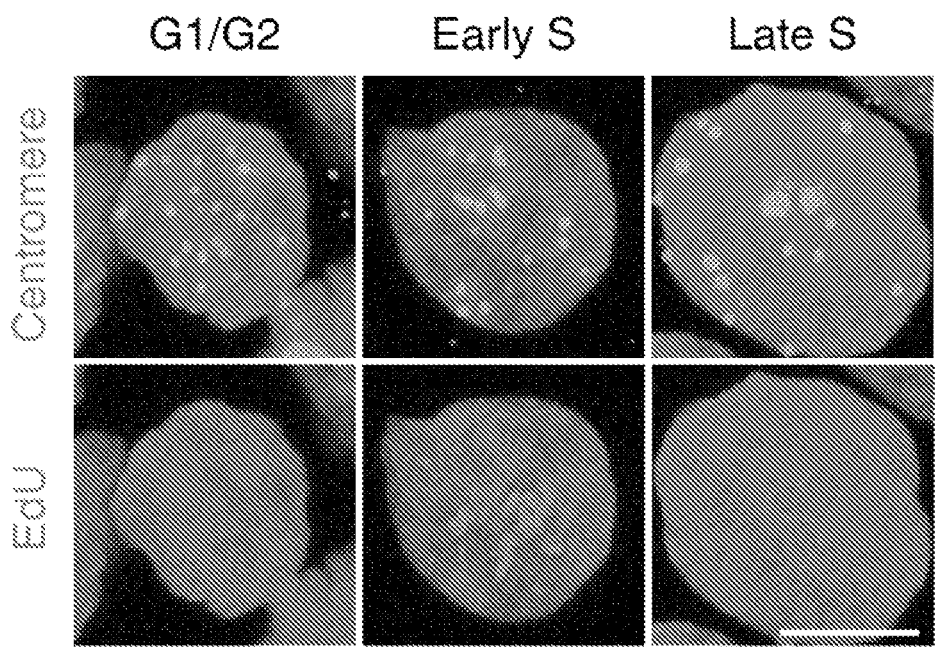
Figure 6F:
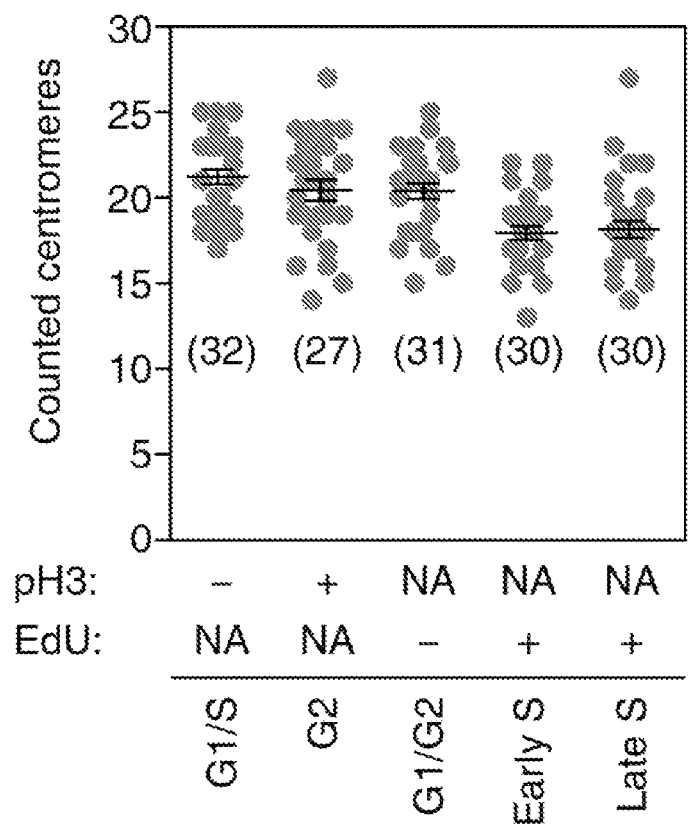

FIG. 6a-6f show determination of ploidy at single-cell level by quantification of centromere foci. FIG. 6a shows that the counted number of centromeres correlates with ploidy. 1n: haploid-enriched pES10 cells grown for 4 passages after the forth sort (n=33; 76% haploids by this assay); 2n: unsorted diploid pES10 cells (n=34); 3n: soPS2 cells35 (n=27); 4n: Hybrid1 cells36 (n=27). Black horizontal lines indicate mean±s.e.m. and dashed lines mark expected chromosome numbers. FIG. 6b shows quantification of haploid (1n) and diploid (2n) cells by DNA FISH in the haploid-enriched (n=152; 73% haploids by this assay) and diploid (n=135) cells in FIG. 6a. FIG. 6c shows the DNA content profile of the haploid-enriched cells in FIG. 6a (73% haploids by this assay). c: chromosomal copies. Co-staining of centromeres and either phospho-histone 3 (pH3, Ser10) (FIG. 6d) or 5-ethynyl-2'-deoxyuridine (EdU) (FIG. 6e) distinguishes between different stages of interphase in haploid pES12 cells. DNA staining is shown in blue. Scale bar=5 µm. FIG. 6f shows quantification of centromere counts in the different cell cycle stages shown in FIG. 6d and FIG. 6e. indicated in parenthesis. Black horizontal lines indicate mean±s.e.m.

Figure 7:
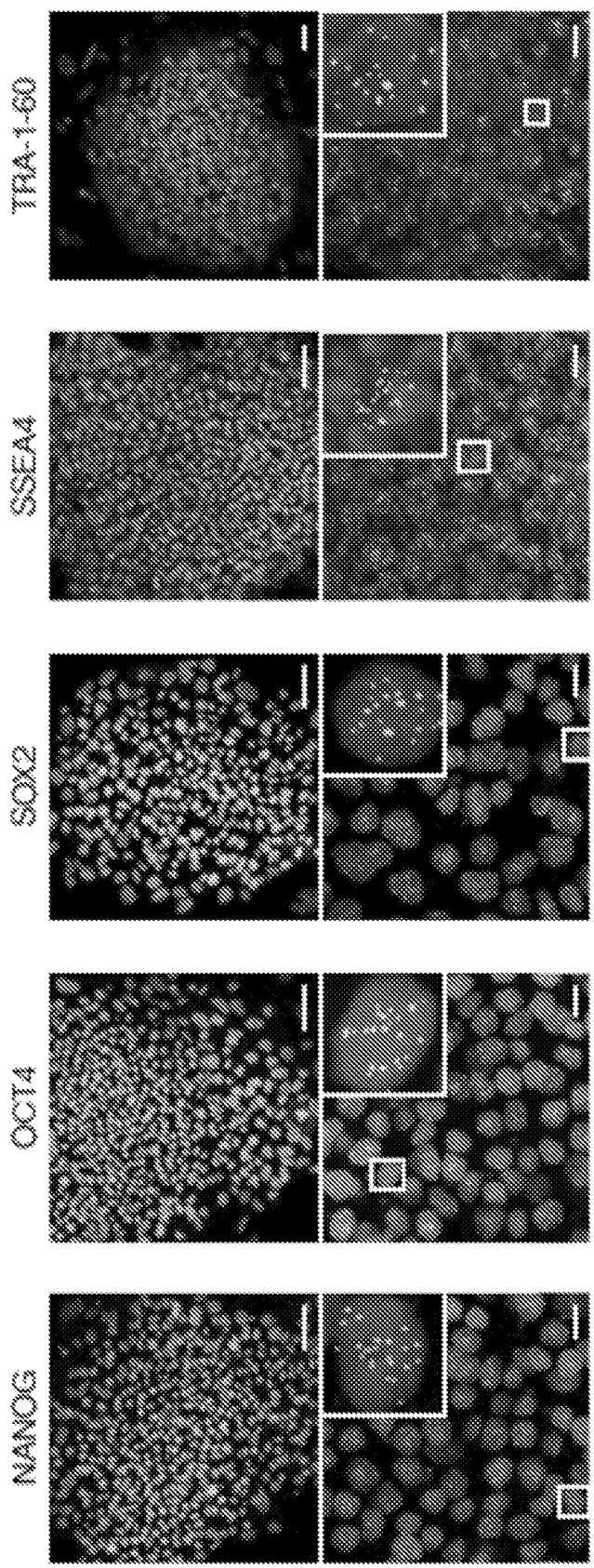

FIG. 7 shows pluripotent stem cell markers in haploid pES12 cells. Co-staining of pluripotency markers NANOG, OCT4, SOX2, SSEA4 and TRA-1-6 (red), centromeres (green) and DNA (blue) in h-pES12 at colony resolution (upper panel; scale bars=50 µm) and single-cell resolution (lower panel; scale bars=10 µm) is shown. Magnified insets show representative haploid cells with 23 centromeres.

Figure 8A:
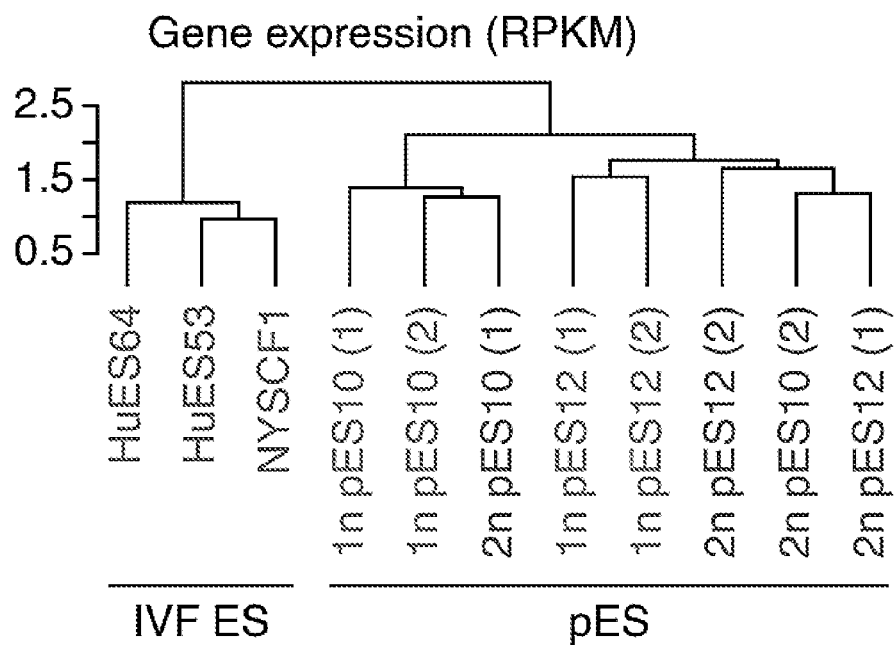
Figure 8B:
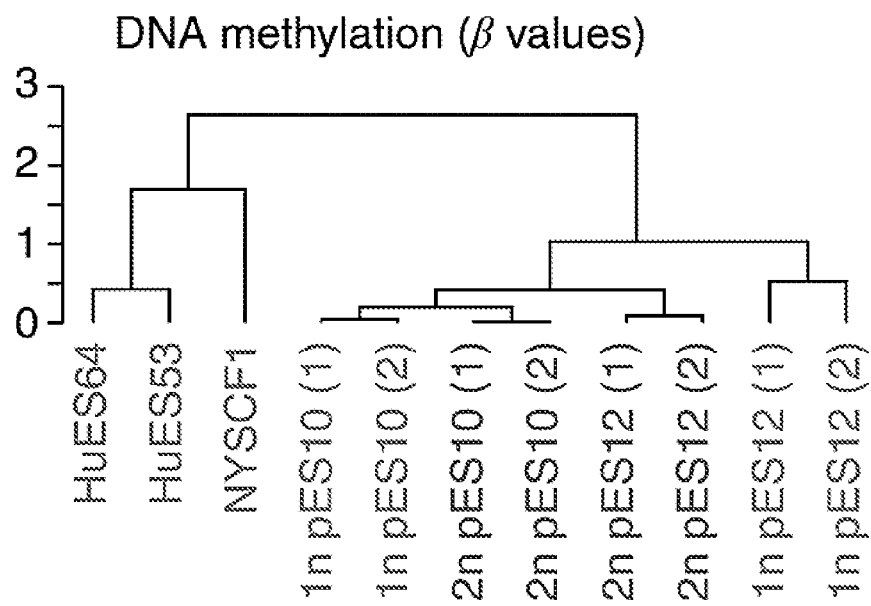
Figure 8C:
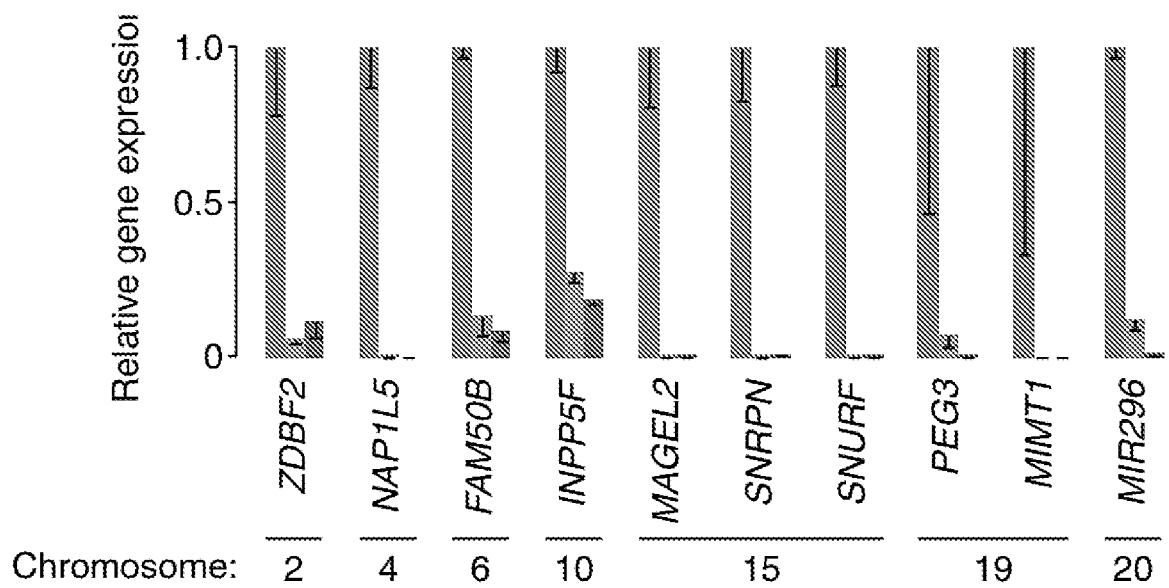
Figure 8D:
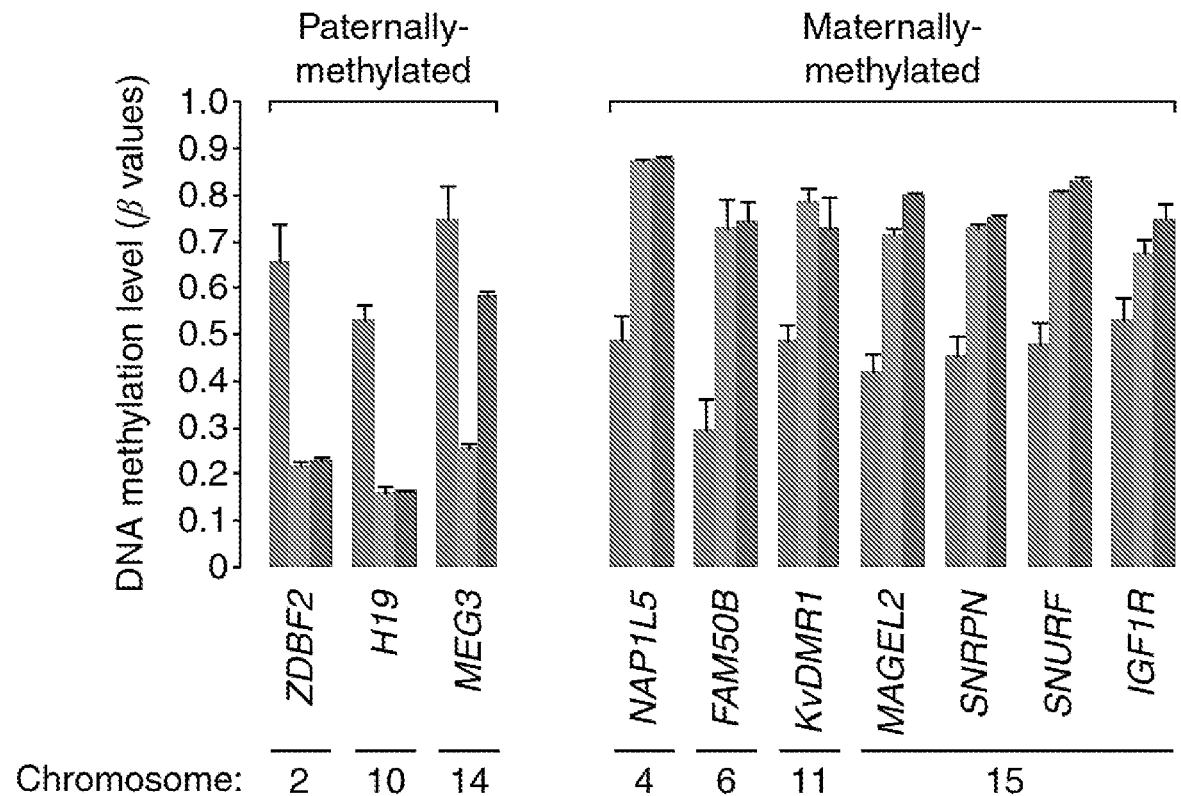
Figure 8E:
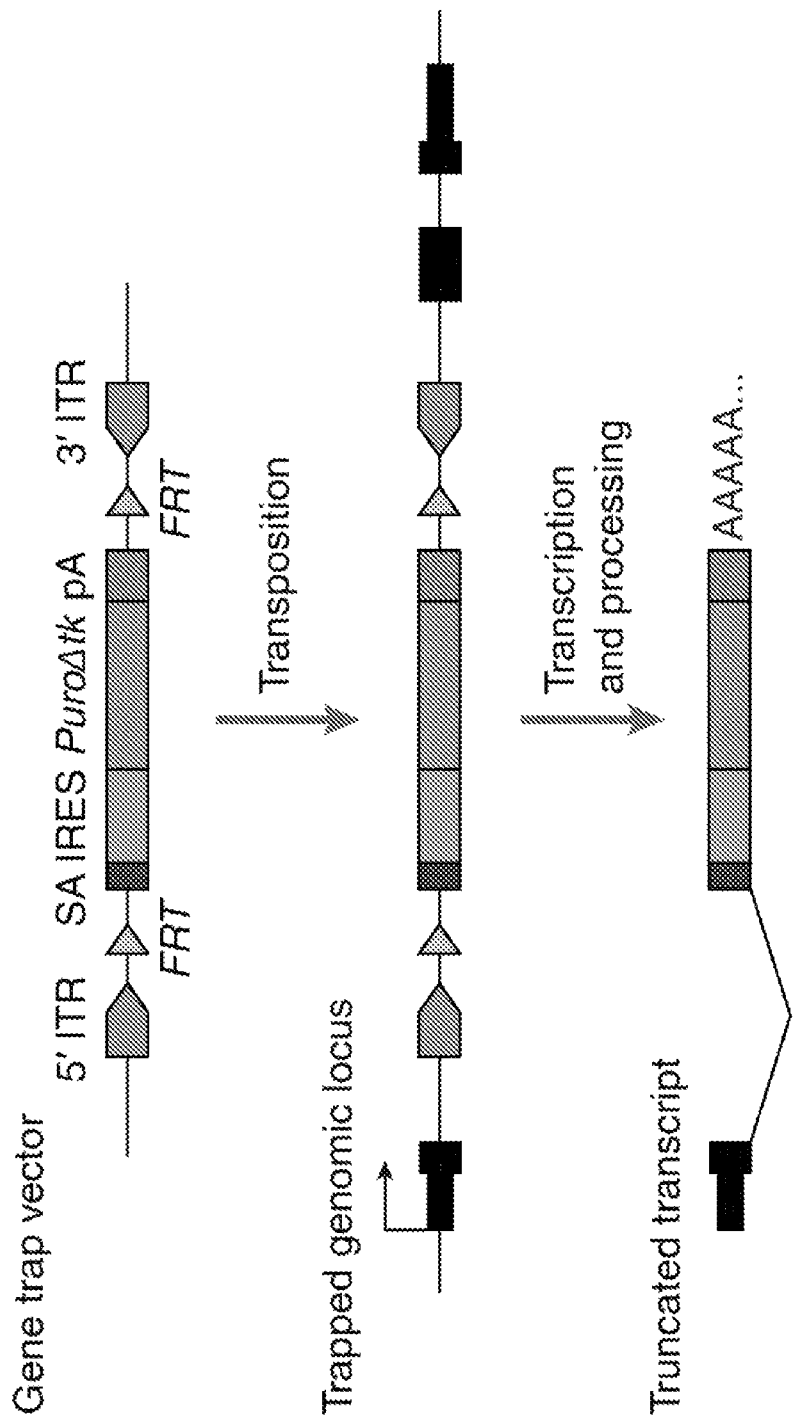

FIG. 8a-8e show analysis of parental imprinting and gene trap mutagenesis in haploid human parthenogenetic ES cells. FIG. 8a and FIG. 8b show hierarchical clustering analysis of diploid (2n) in vitro fertilization (IVF) ES cells and G1-sorted haploid (1n) and diploid parthenogenetic ES (pES) cells by expression levels of imprinted genes (n=75, see Table 6) (FIG. 8a) and DNA methylation levels at imprinted differentially methylated regions (iDMRs, n=35) 37 (FIG. 8b). (1) and (2) denote biological replicates. FIG. 8c shows relative mean expression levels±s.e.m. of representative paternally-expressed imprinted genes across seven chromosomes in the samples shown in FIG. 8a (RPKM ratios). FIG. 8d shows mean DNA methylation levels±s.e.m. at representative paternally-methylated and maternally-methylated iDMRs (typically intermediately methylated in bi-parental control cells, and respectively hypomethylated and hypermethylated in parthenogenetic cells) in the samples shown in FIG. 8b. β values range from complete hypomethylation (0) to complete hypermethylation (1). FIG. 8e shows a schematic outline of the piggyBac gene trap system. The gene trap vector52 is flanked by piggyBac inverted terminal repeats (ITRs) and FRT sites, and carries a 5' splice acceptor (SA), an internal ribosome entry site (IRES) element followed by a promoterless puromycin resistance gene (PuroΔtk) and a 3' poly(A) signal (pA). In the presence of the PiggyBac transposase (encoded on a separate plasmid53), the gene trap vector undergoes random transposition into the genome. Insertion into a transcriptionally active gene results in truncation of the endogenous transcript and introduction of resistance to puromycin. ITR: inverted terminal repeat; FRT: flox sites.

Figures 9A, 9B:
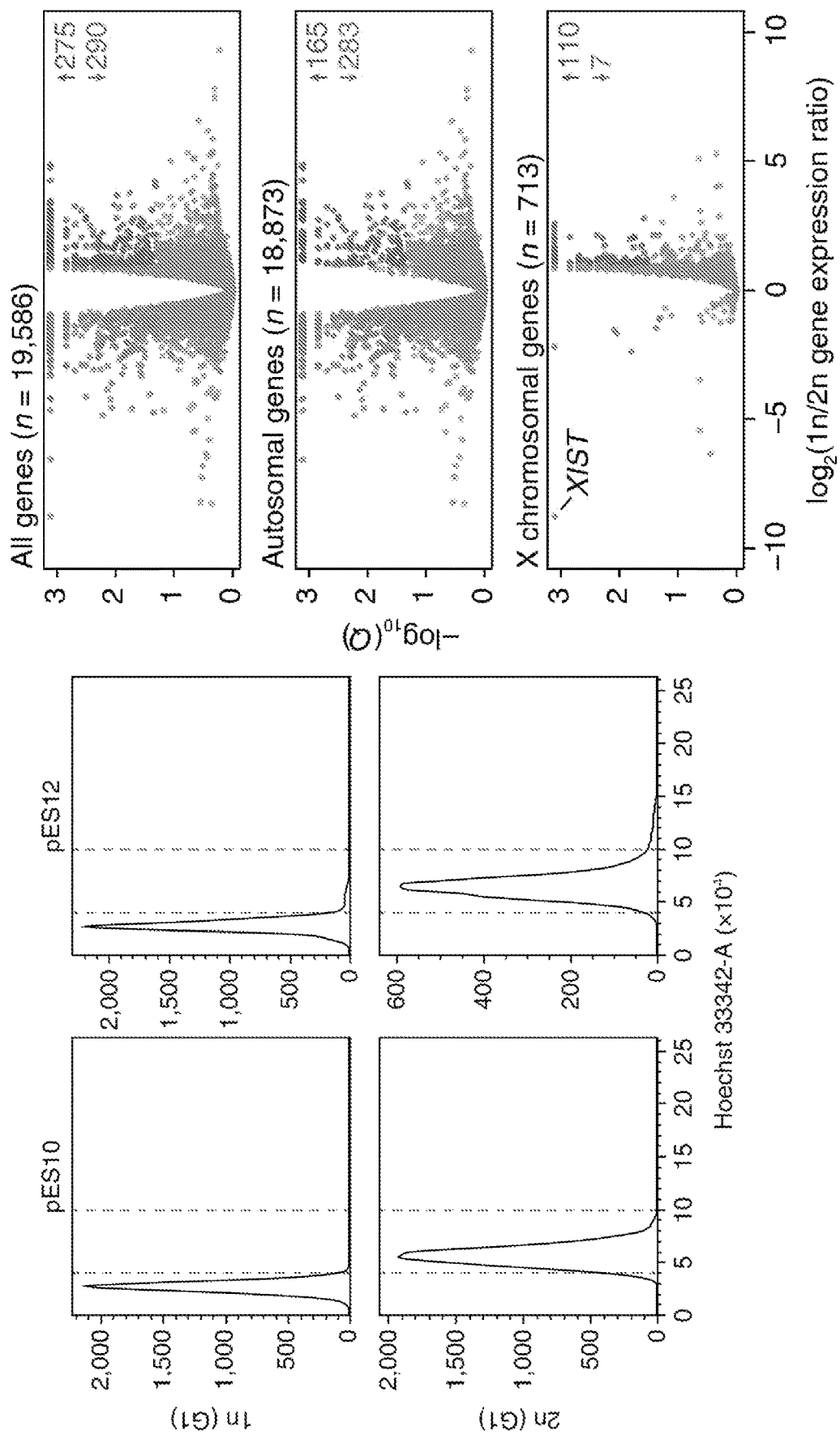
Figure 9C:
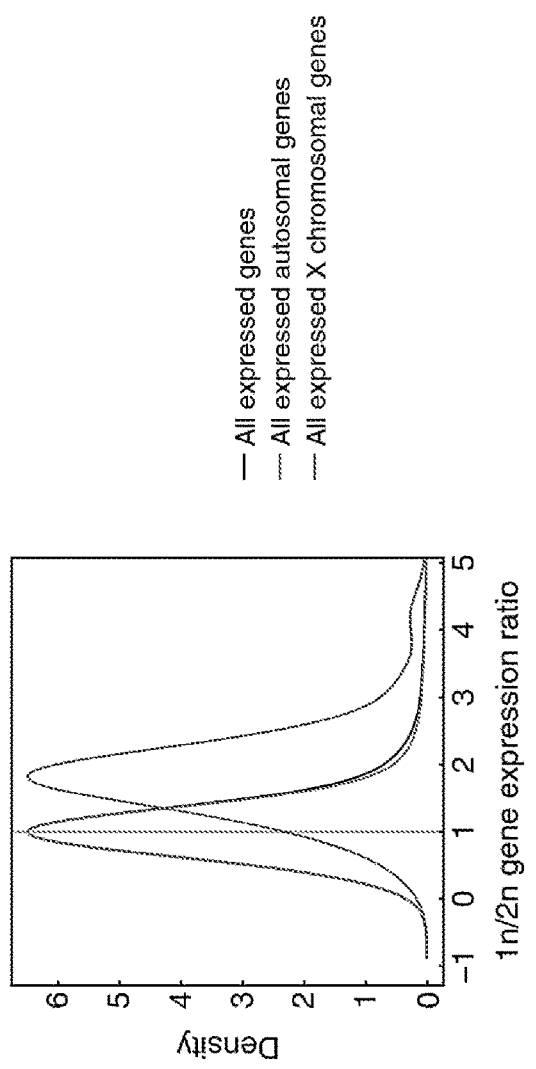
Figure 9D:
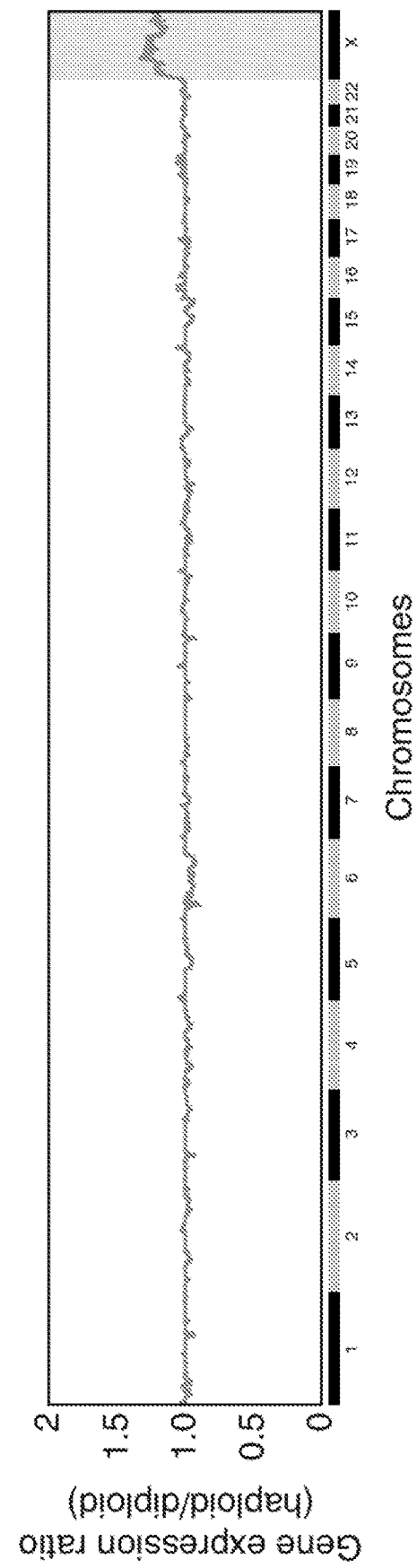
Figure 9E:
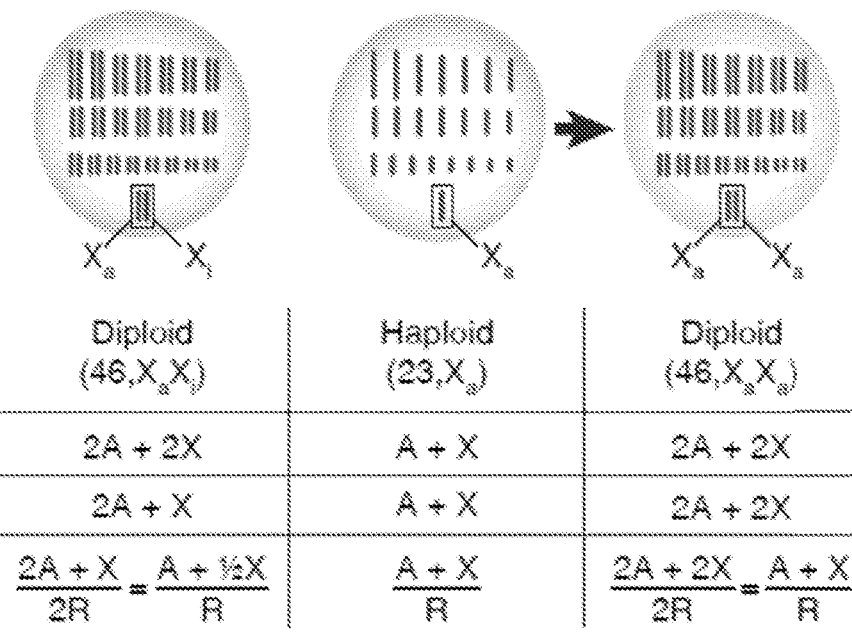
Figure 9F:
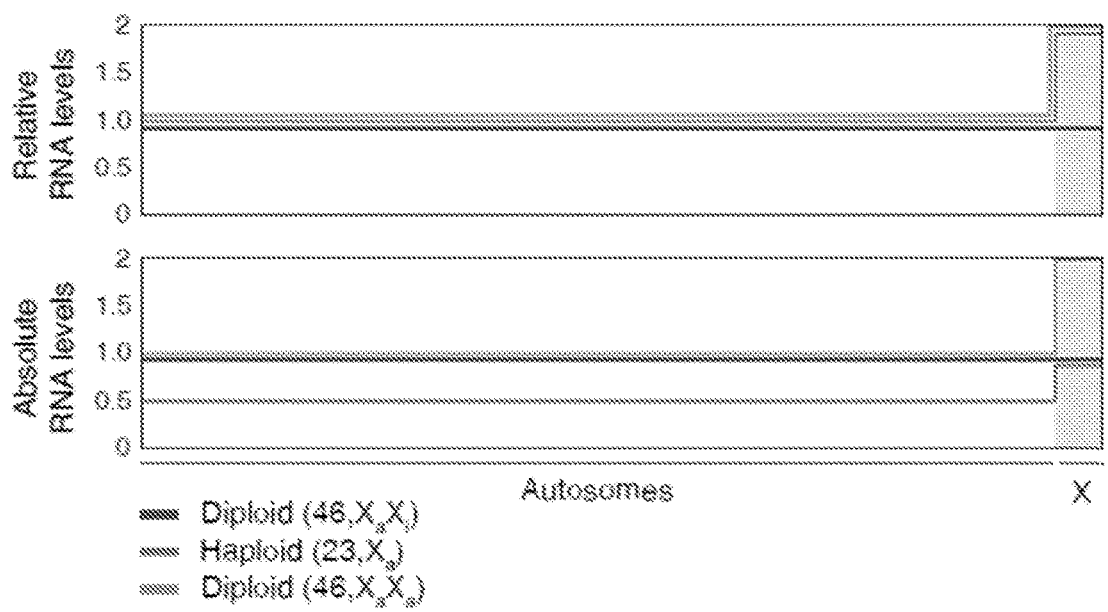
Figure 9G:
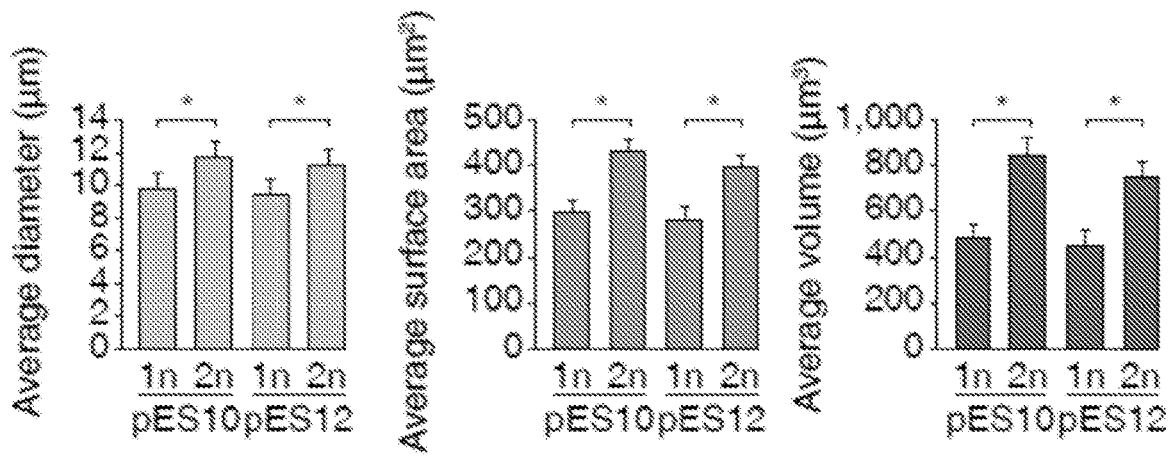
Figure 9H:
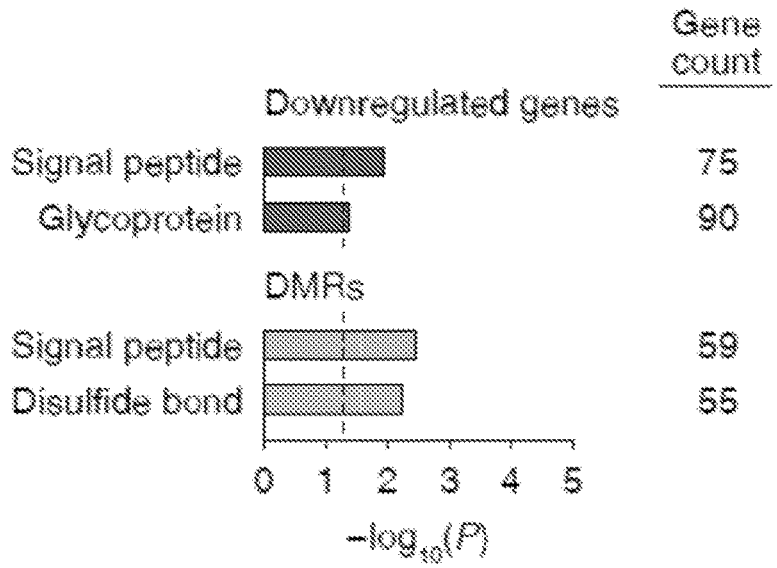
Figure 9I:
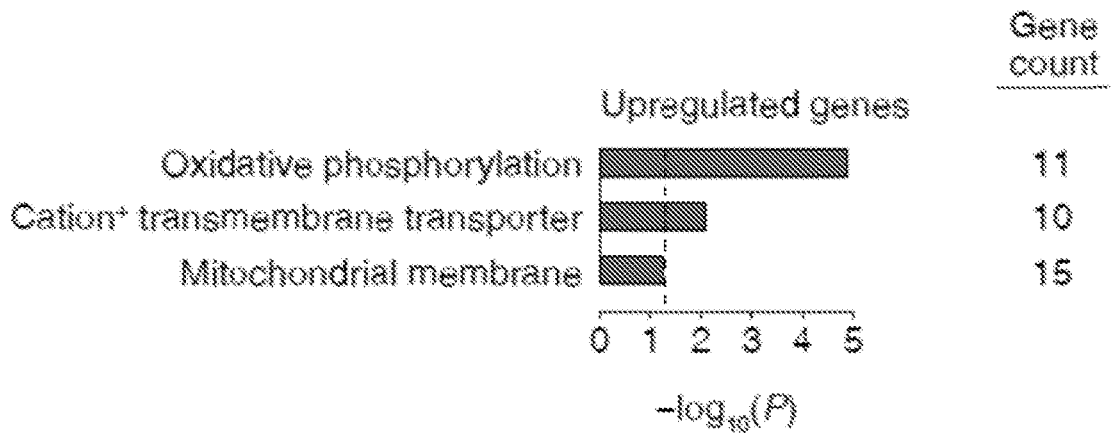

FIG. 9a-9i show comparative analyses of isogenic haploid and diploid human ES cells. FIG. 9a shows sorting purity of haploid (1n) and diploid (2n) ES cells in G1. FIG. 9b shows log-scaled volcano plots of relative differential gene expression between haploid and diploid human ES cells, divided into panels by all genes (top), autosomal genes (middle) and X chromosomal genes (bottom). Q: false discovery rate (FDR). Significantly downregulated and upregulated genes (>2-fold change, Q<0.05) in haploid cells are marked in red and blue, respectively, and their totals are indicated to the right. Note that XIST is the most downregulated transcript in haploid cells. FIG. 9c shows smoothed distributions of the 1n/2n gene expression ratios for all expressed genes, all expressed autosomal genes and all expressed X chromosomal genes (expression threshold, mean RPKM>0.1). FIG. 9d shows a genome-wide moving median plot of the gene expression ratio between haploid and diploid pE10 cells in G1 by expression microarray analysis (window size=100 genes). FIG. 9e and FIG. 9f show a model for genome-wide autosomal gene level reduction in haploid human ES cell as inferred by differential XCI status. FIG. 9e shows that DNA content, RNA expression levels relative to total RNA, and presumed equality of absolute X chromosomal gene dosage in haploid (Xa) and diploid (XaXi) human ES cells enable the estimation of total RNA levels per haploid cell. Xa and Xi denote active (blue) and inactive (red) X chromosomes, respectively. A: autosomes; X: X chromosome; R: total RNA. FIG. 9f shows schematic genome-wide representation of relative and absolute RNA levels in the cells shown in FIG. 9e. FIG. 9g shows average diameter and calculated surface area and volume of G1-sorted haploid and diploid ES cells. Error bars represent s.d. (n=4-8). *P<0.01 (two-tailed unpaired Student's t test). FIG. 9h and FIG. 9i show functional annotation enrichment analysis for relatively downregulated genes and differentially methylated regions (DMRs) (FIG. 9h) as well as relatively upregulated genes (FIG. 9i) in haploid ES cells compared with diploid ES cells.

Figure 10A:
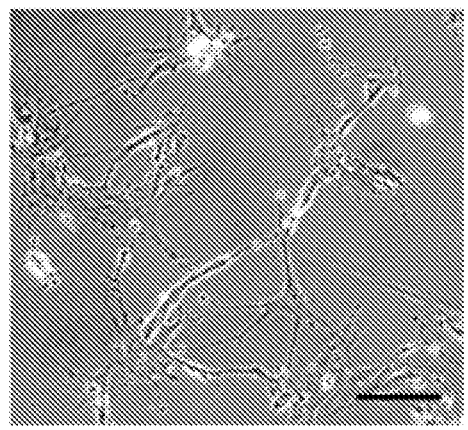
Figure 10B:
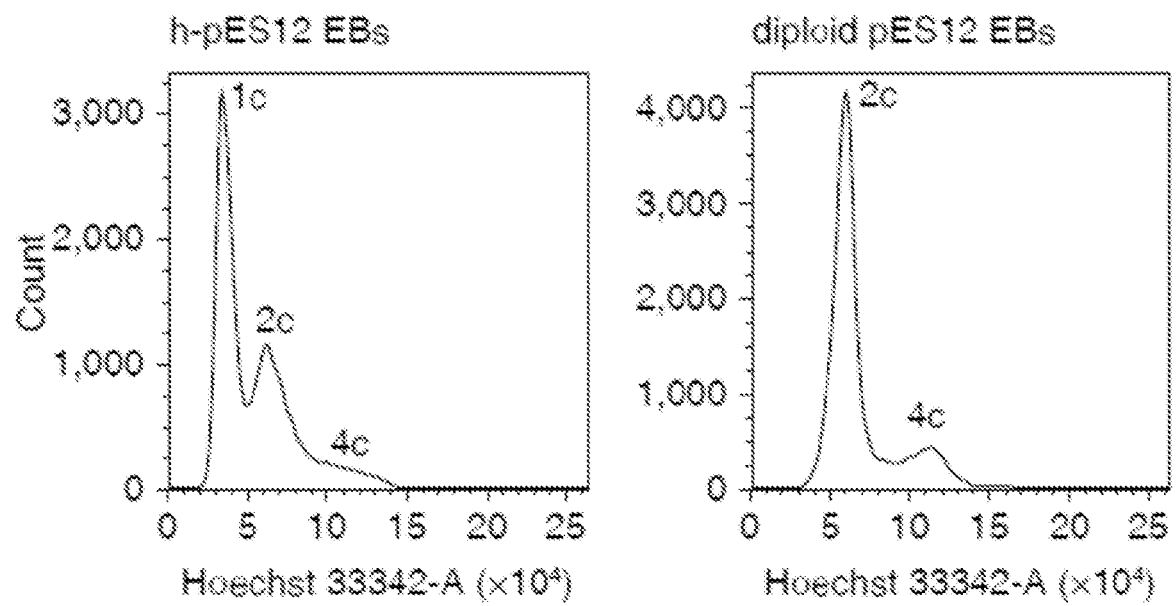
Figure 10C:
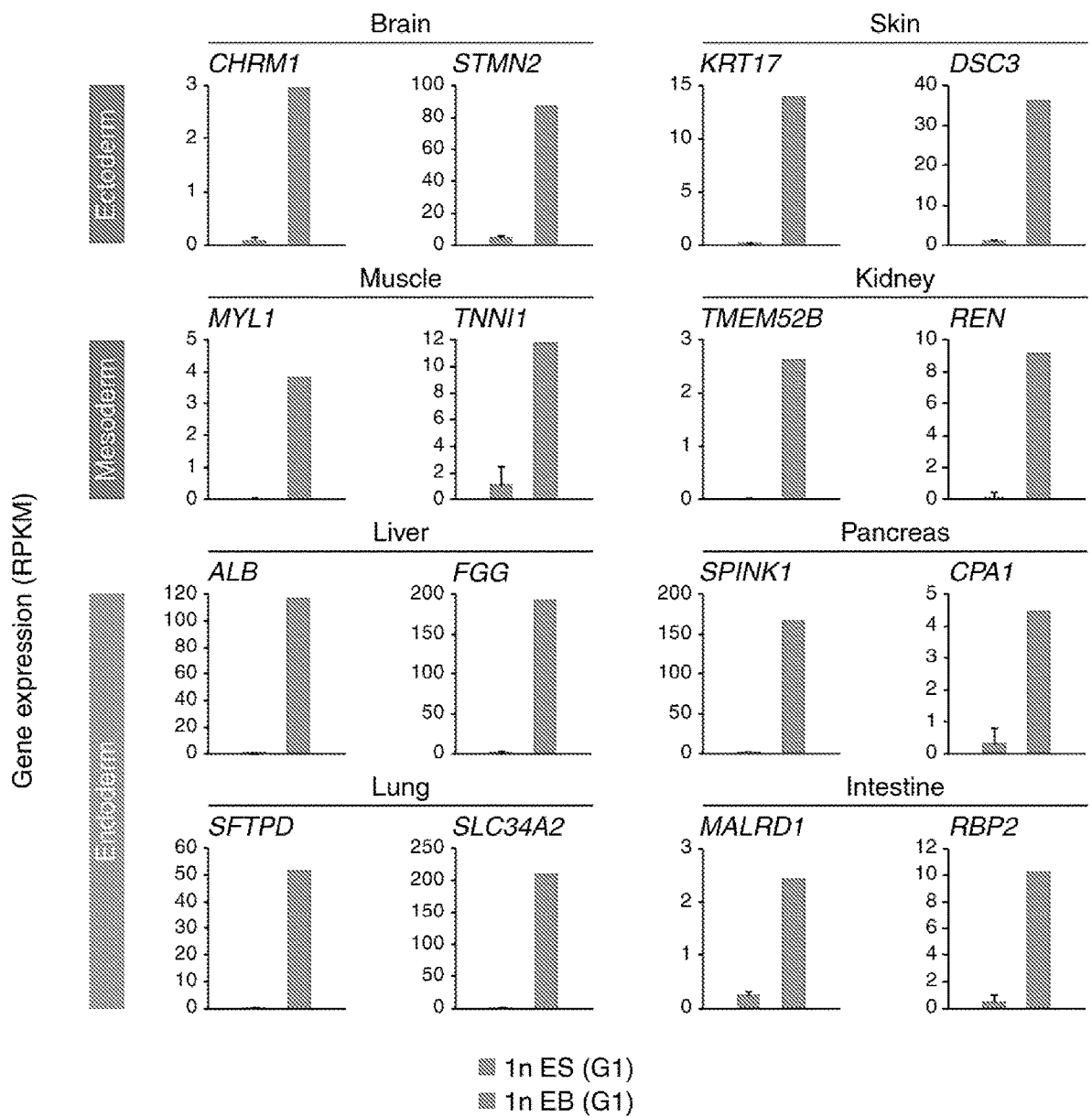

FIG. 10a-10c show EB differentiation of haploid human ES cells. FIG. 10a shows a representative image of plated cells dissociated from h-pES12-derived 21-day EBs, the karyotype of which is presented in FIG. 4b. Scale bar=100 µm. FIG. 10b shows DNA content profiles of dissociated EBs derived from haploid-enriched and diploid pES12 cells. c: chromosomal copies. FIG. 10c shows expression levels (RPKM) of tissue- and pluripotency-specific genes in undifferentiated (ES) and differentiated (EB) G1-sorted haploid (1n) pES10 cells.

Figure 11A:
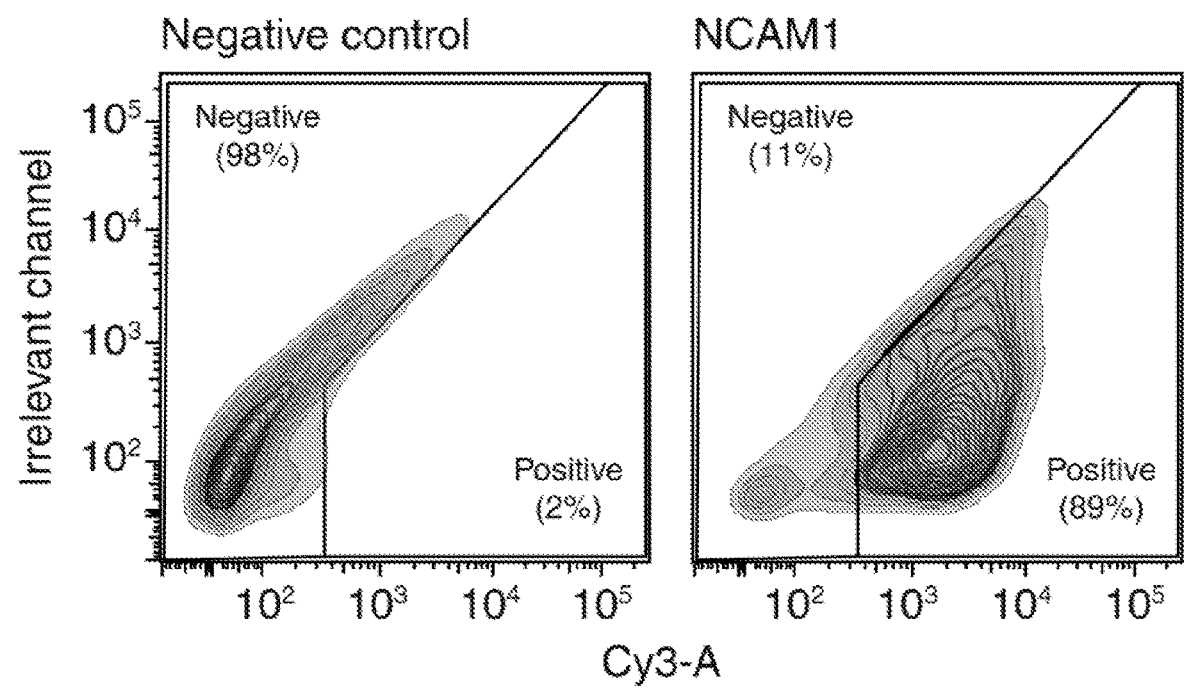
Figure 11B:
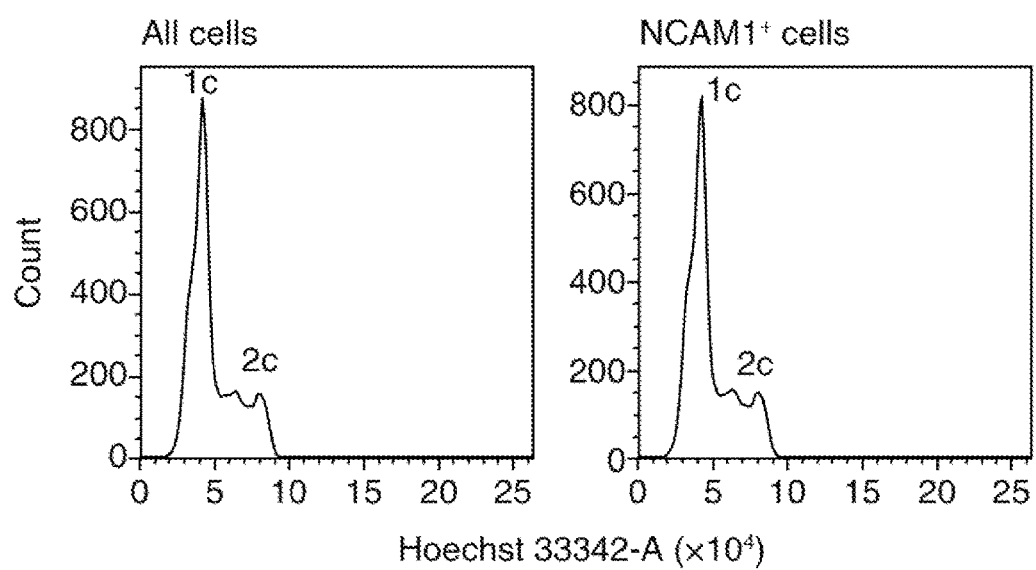
Figures 11C, 11D:
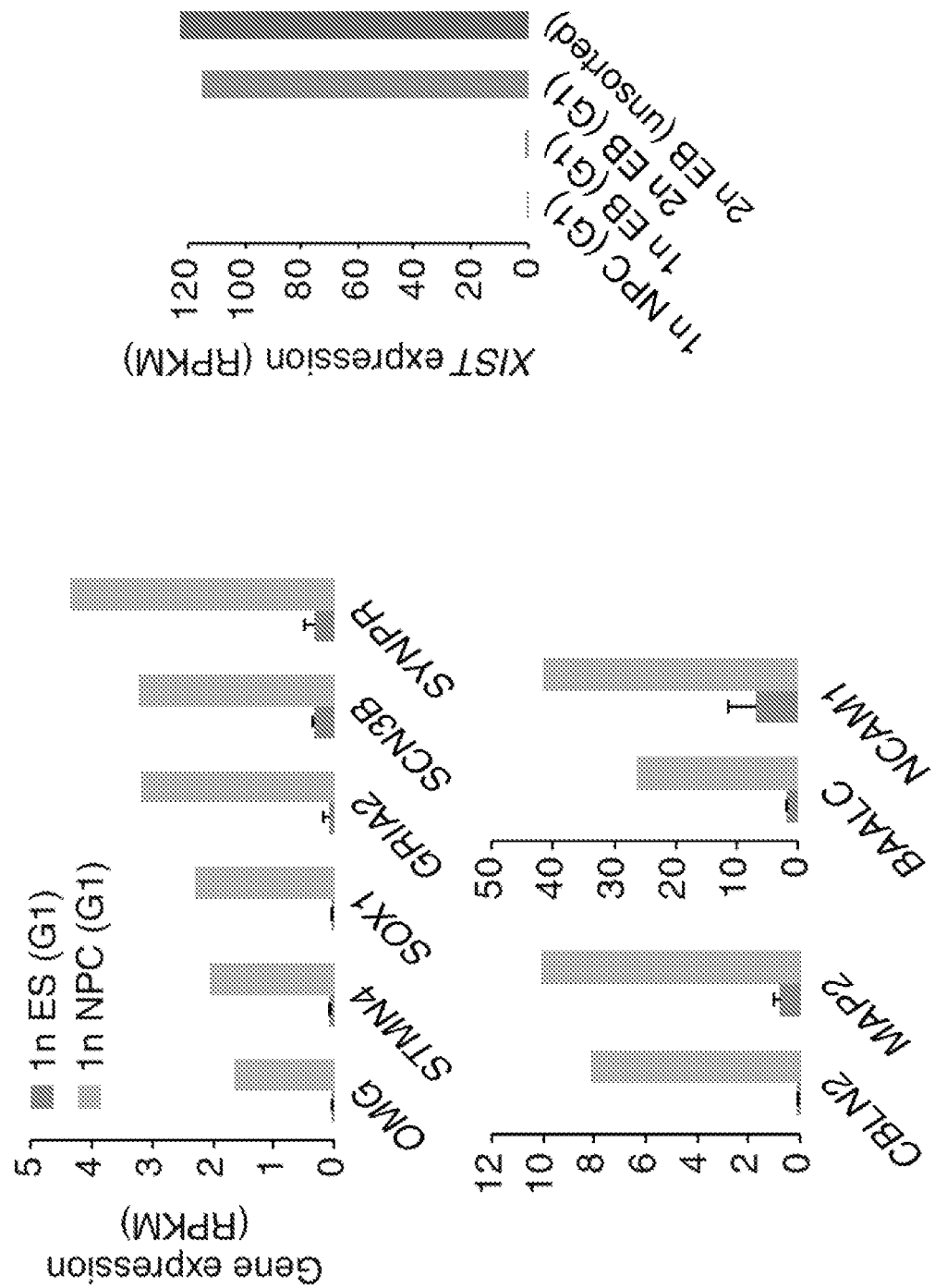
Figure 11E:
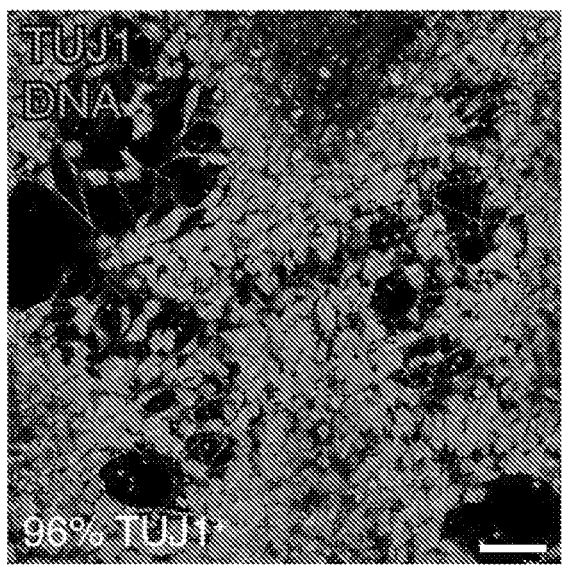
Figure 11F:
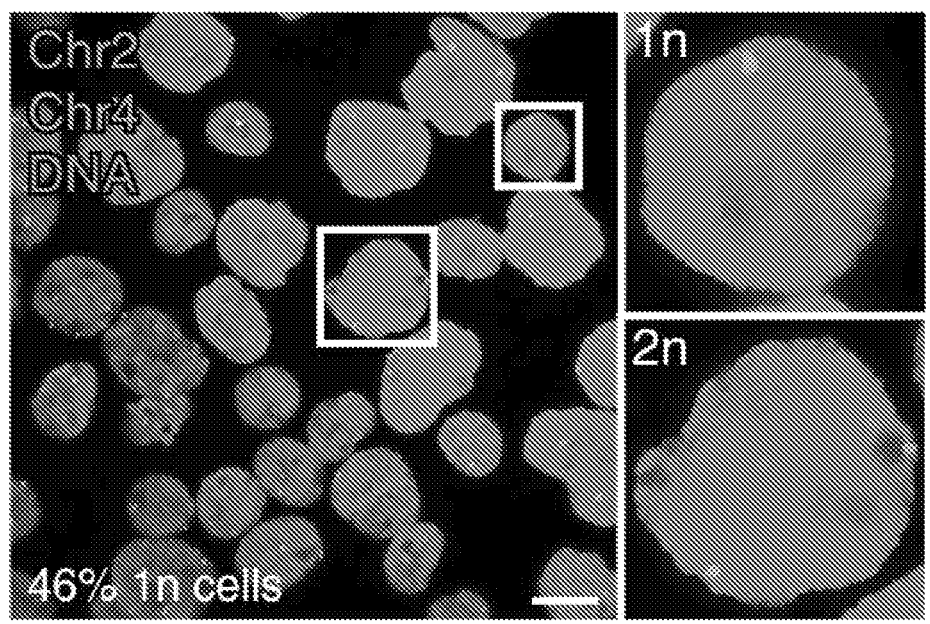
Figure 11G:
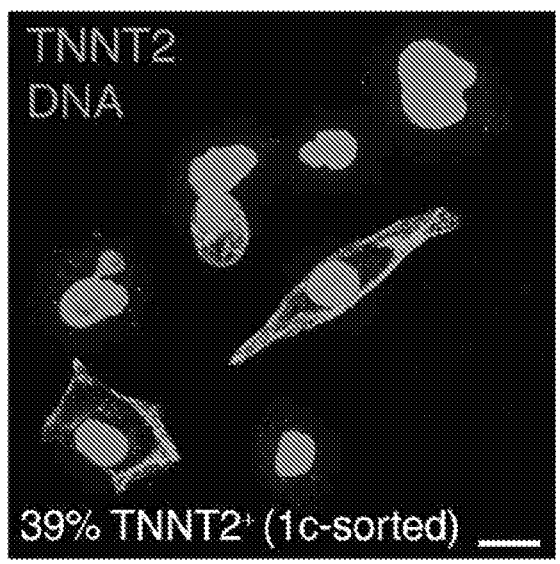
Figure 11H:
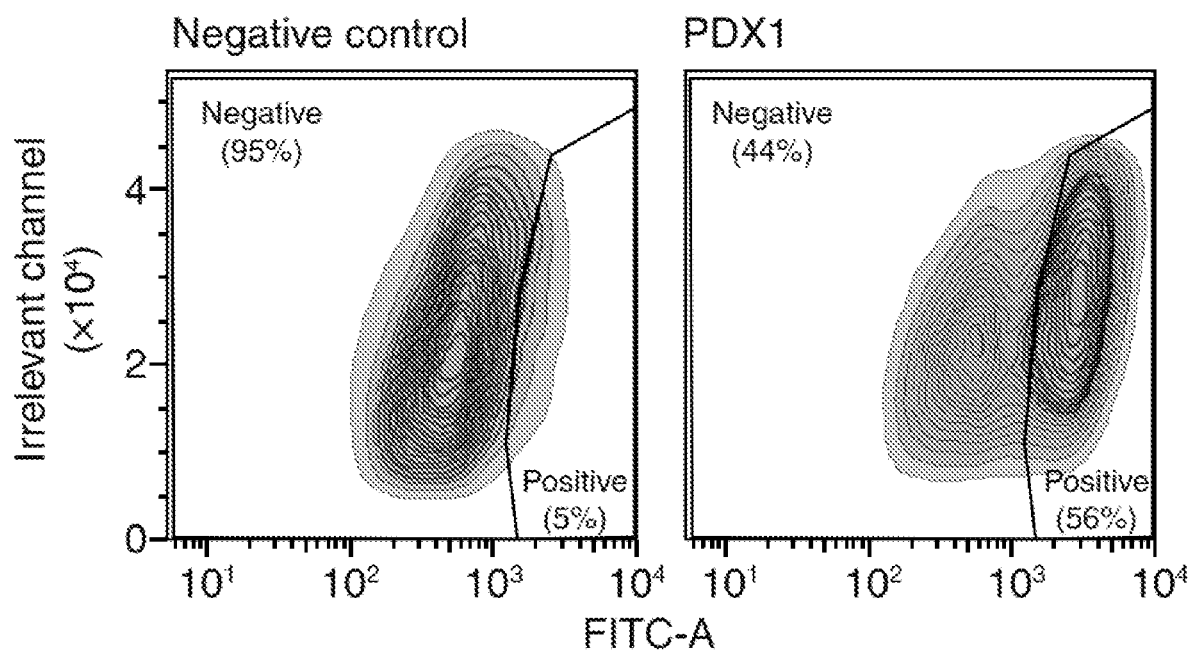
Figure 11I:
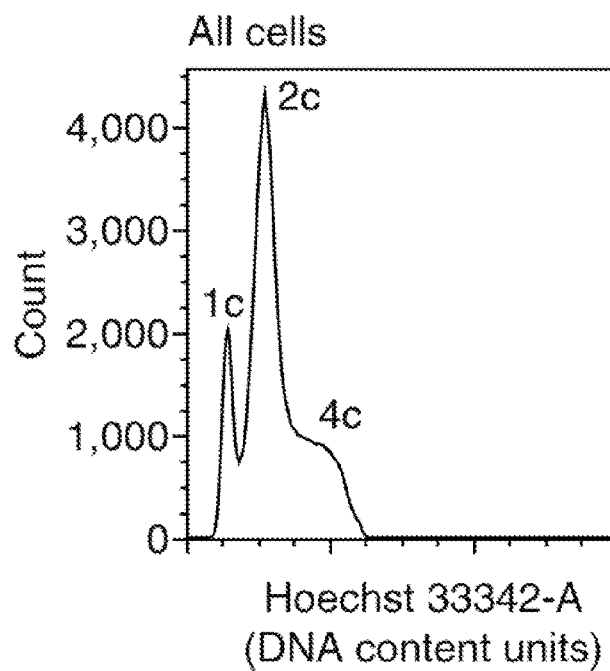

FIG. 11a-11i show directed differentiation of haploid human ES cells. FIG. 11a and FIG. 11b show flow cytometry analysis with co-staining of DNA and NCAM1 in h-pES10 cells following neural differentiation. FIG. 11a shows gating for NCAM1-positive cells (right panel) based on a negative secondary-antibody-stained control sample (left panel). FIG. 11b shows DNA content profile of the entire cell population (related to FIG. 4e). c: chromosomal copies. FIG. 11c shows expression levels (RPKM) of neural-specific genes in G1-sorted haploid (1n) pES10 ES cells and NPCs. FIG. 11d shows XIST expression levels in haploid and diploid (2n) pES10-derived EBs and NPCs. FIG. 11e shows TUJ1 staining in h-pES12-derived neurons. Scale bar=100 µm. FIG. 11f shows DNA FISH on the neurons shown in FIG. 11e. Magnified insets show representative haploid and diploid nuclei with single and double hybridization signals, respectively. Scale bar=10 µm. FIG. 11g shows TNNT2 staining in G1-sorted haploid pES12-derived cardiomyocytes. Scale bar=10 µm. FIG. 11h and FIG. 11i show flow cytometry analysis with co-staining of DNA and PDX1 in h-pES10 cells following pancreatic differentiation. FIG. 11h shows gating for PDX1-positive cells (right panel) based on a negative secondary-antibody-stained control sample (left panel). FIG. 11i shows DNA content profile of the entire cell population (related to FIG. 4m). c: chromosomal copies.

Figure 12A:
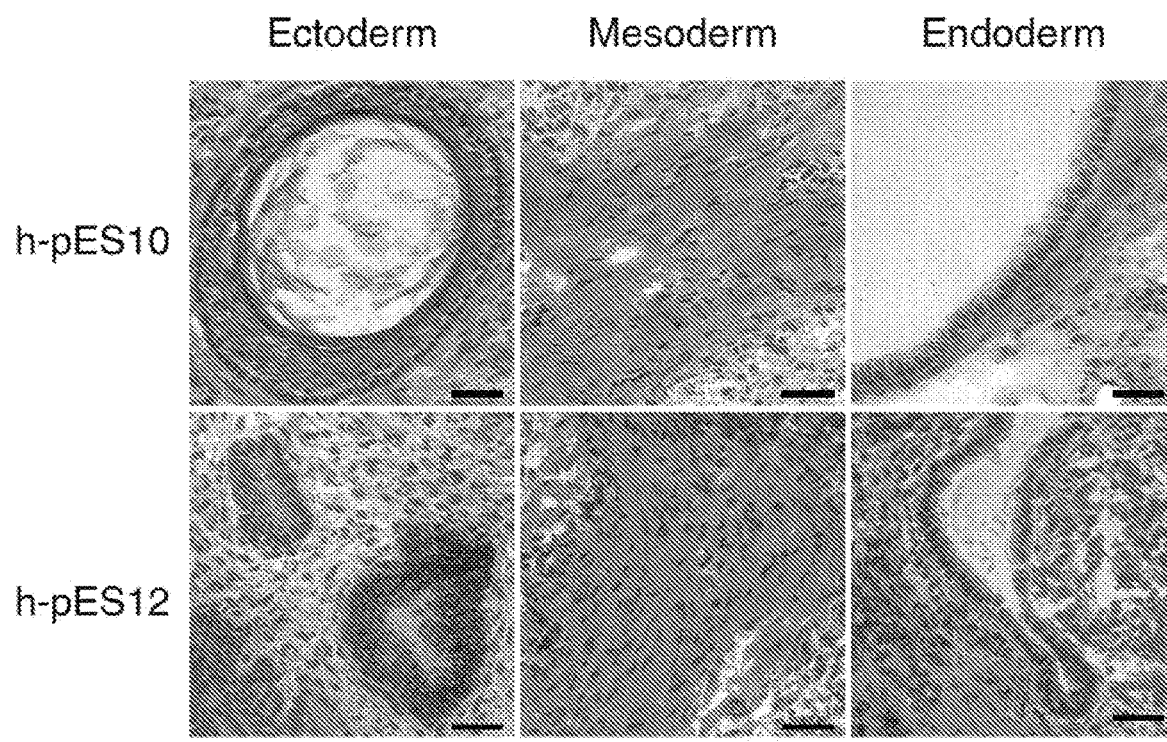
Figure 12B:
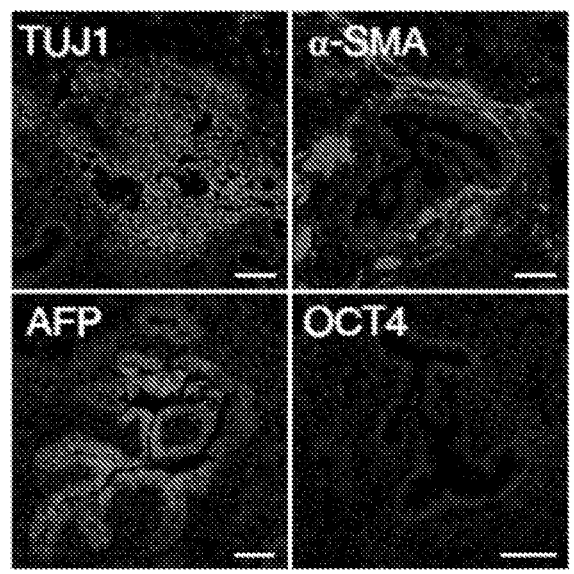

FIG. 12a and FIG. 12b show in vivo differentiation of haploid human ES cells. FIG. 12a shows hematoxylin and eosin histological sections of teratomas derived from h-pES10 and h-pES12. Scale bar=50 µm. FIG. 12b shows TUJ1 (ectoderm), α-SMA (mesoderm), AFP (endoderm) and OCT4 (pluripotency) staining in an h-pES10-derived teratoma. DNA staining is shown in blue. Note the absence of nuclear OCT4 staining. Scale bars=100 µm.

DETAILED DESCRIPTION OF THE INVENTION

Many aspects of the present invention are described in the above Summary of the Invention section of this patent application, as well as in the Drawings/Figures, the Brief Description of the Drawings/Figures, and the Claims sections of this patent application. This Detailed Description section provides certain additional description relating to the present invention and is intended to be read in conjunction with all other sections of this patent application.

The invention provides haploid human parthenogenetic ES cell lines following activation of haploid human oocytes. Earlier studies on mouse oocyte activation have demonstrated that haploidy likely persists at least partially in the inner cell mass (ICM) of the resulting embryo.8,9 Nonetheless, diploids cells progressively dominate over increasing cell cycles, due to spontaneous and irreversible diploidization events (FIG. 1a).9,16,17 Based on a diploidization kinetics model, we estimated that even if diploidization should occur in 1 out of 10 cell cycles, 1% of ES cells may remain haploid at early passages (FIG. 1b). To model diploidization dynamics of ES cells in culture or of early embryonic cells, we considered the following definitions and assumptions:

(1) If $H_n$ is the total number of haploid cells at the $n^{th}$ cell division cycle, and p is the probability of undergoing diploidization at a single cell division cycle, the total number of diploidization events (d) at the $n^{th}$ cell division cycle is:

$$d_n = p \cdot H_{n-1}$$

(2) The total number of diploid cells (D) at the at the nth cell division cycle is:

$$D_n = 2D_{n-1} + d_n$$

(3) The total number of cells (T) at the at the nth cell division cycle is:

$$T_n = 2T_{n-1} - d_n$$

(4) And the haploid fraction (h) at the nth cell division cycle is thus:

$$h_n = \frac{H_n}{T_n} = \frac{T_n - D_n}{T_n} = 1 - \frac{D_n}{T_n} = 1 - \frac{2D_{n-1} + d_n}{2T_{n-1} - d_n} = 1 - \frac{2D_{n-1} + p \cdot H_{n-1}}{2T_{n-1} - p \cdot H_{n-1}}$$

For simplification, we further assumed that:

(1) Diploidization occurs due to failed cell division cycle at a constant probability, resulting in one diploid daughter cell rather than two haploid daughter cells.

(2) Normal cell division cycles produce two daughter cells, and are synchronous on average.

(3) Any selective advantage in favor of either haploid or diploid cells is negligible, and cases of cell death and aneuploidy are not considered.

Simulation of this model throughout 100 cell division cycles generated the data points plotted in FIG. 1b, fitting an exponential decay function.

The frequency of haploid cells, which decreases over time due to a gradual and irreversible acquisition of a diploid genome, required the analysis of over 2,000 metaphases and a total of 14 parthenogenetic ES cell lines at passages 4-10, to allow the establishment of two individual haploid ES cell lines with a 14% success rate. Overall, we have utilized four independent methodologies, namely metaphase spread analysis, flow cytometry, FISH and centromere quantification, to determine ploidy in undifferentiated and differentiated cells.

Haploid and diploid human ES cells shared many similarities, including classical pluripotent stem cells attributes as well as multilineage differentiation potential in vitro and in vivo, and could not be distinguished based on their relative global gene expression profiles. While other studies on non-human haploid ES cells mostly emphasized their resemblance, we aimed to identify putative transcriptional, epigenetic and physical properties that set these two ploidy states apart. XCI, which is readily observed in diploid human ES cells,19 does not occur in haploid ES cells. Notably, the absence of XCI also extends into recently diploidized ES cells, which may later become XaXi in culture. These findings allowed us to infer a reduction in absolute gene expression levels in haploid human ES cells, a conclusion that could not have been drawn in undifferentiated mouse ES cells, where XCI does not occur.26 This suggests that global transcriptional compensation is not a prerequisite for cellular viability as long as an autosomal balance is preserved. In contrast, autosomal imbalance appears intolerable based on the strict absence of human autosomal monosomies.27 Still, the discrepancy between the haploid:diploid ratios of physical parameters such as diameter (~0.8), surface area (~0.7) and volume (~0.6) implies that regulatory robustness involves specific compensatory mechanisms. Interestingly, we observed subtle yet consistent relative upregulation of genes involved in oxidative phosphorylation involving a coordinated crosstalk between nuclear and mitochondrial genomes, which is likely the reflection of a relative increase in mitochondria abundance in haploid cells. This robustness could reflect a more permissive regulatory phase in the early embryo, particularly in light of X chromosome dosage and elevated oxidative phosphorylation activity, which are both consistent with an early preimplantation epiblast identity.28

We show that a haploid human karyotype is not a barrier for ES cell differentiation. In particular, we show that haploid human ES cells give rise to neural progenitor cells while remaining haploid, as has also been observed in the mouse2. However, while mouse studies showed that haploid cells are lost upon further differentiation,2,16 we observed specification of human haploid cells into somatic cell fates of all three embryonic germ layers, despite a dosage imbalance between the X chromosome and autosomes that persisted from the pluripotent state into the differentiated state.

Haploid human ES cells of the invention are identified by metaphase spread analysis or sub-2c (where "c" stands for chromosomal copy number) cell sorting of a population of ES cells derived from artificially activated human oocytes. Haploid human ES cells can also be identified by flow cytometry, preferably FACS, centromere protein immunofluorescence staining, or DNA FISH. Methods for carrying out metaphase spread analysis and sub-2c sorting, centromere protein immunofluorescence, and DNA FISH are known in the art and described herein.

Methods of artificial activation are known in the art and include, but are not limited to, parthenogenetic activation and androgenetic activation. Parthenogenetic techniques involve the activation of the oocyte using an electrical pulse, a calcium ionophore, a kinase inhibitor, a translation inhibitor or a combination of these.41 Androgenetic techniques involve the fertilization of an enucleated oocyte with a sperm, typically by intracytoplasmic sperm injection. The genome of the oocyte is removed before or after fertilization of the oocyte to generate a cell that contains only the sperm genome. The oocyte may be exposed to an activation stimulus as for parthenogenesis.

Flow cytometry, including FACS, can be used in the methods of the invention to identify and/or sort cells based on ploidy, cell surface markers, or other phenotypic characteristic(s). Other cell sorting techniques known in the art, for example, magnetic-activated cells sorting (MACS), can also be used in the methods of the invention.

The haploid human ES cells and cells lines of the invention can be kept "in culture," which refers, by a non-limiting example, to standard human ES cell growth conditions. Namely, culture on a feeder layer of arrested mouse embryonic fibroblasts in gelatin-coated plates in medium containing Knockout Dulbecco's Modified Eagle's Medium (Gibco, Life Technologies) supplemented with 15% Knockout Serum Replacement (KSR; Gibco, Life Technologies), 2 mM L-glutamine, 0.1 mM nonessential amino acids, penicillin and streptomycin (50 units mL-1 and 50 µg mL-1, respectively), 0.1 mM β-mercaptoethanol and 8 ng mL-1 basic fibroblast growth factor. Cells can be maintained in a humidified incubator at 37° C. and 5% CO2 and passaged every 3-5 days using Trypsin Solution A without EDTA. Preferably, haploid human ES cells are maintained in culture for at least three passages, at least four passages, at least five passages, at least seven passages, at least ten passages, at least twenty passages, or at least thirty passages. Preferably, haploid human ES cells are maintained in culture for at least about ten days, at least about twenty days, at least about thirty days, at least about forty-five days, at least about sixty days, at least about three months, at least about four months, or at least about six months.

"Multipotent" haploid human cells of the invention are progenitor or stem cells that have the potential to develop into multiple, but not all, cell types. Neural stem cells, hematopoietic stem cells, and mesenchymal stem cells are non-limiting examples of multipotent cells. The inventors have demonstrated that multipotent haploid human cells can be produced from embryoid bodies differentiated from haploid human ES cells, or by directed differentiation of haploid human ES cells toward a particular lineage.

The term "cell lines" refers to cells that can grow in culture for many passages, and can be enriched for haploid cells by cell sorting. In accordance with one example of the invention, the cell lines are cultured under standard human ES cell growth conditions and occasional enrichment of the haploid fraction by sorting every 3 to 5 passages.

As used herein, the term "enriched population" refers to a percentage of haploid cells in a total cell population that is greater than 1%, preferably greater than 5%, 10%, 15%, 20%, 25%, 30%, 35%, 40%, 45%, 50%, 55%, 60%, 65%, 70%, 75%, 80%, 85%, or 90%. Typically, an enriched population can be obtained after a single cycle of sorting, such as FACS.

The term "substantially pure" refers to a percentage of haploid cells in a total cell population that is above 90%, preferably above 91%, 92%, 93%, 94%, 95%, 96%, 97%, 98%, or 99%. Most preferably, a substantially pure population is a confluent population of haploid cells.

The haploid human cells of the invention can be used, for instance, in developmental, genetic, and cellular biology research to study basic mechanisms such as haploidy vs. diploidy, X chromosome inactivation, parental imprinting and hybridism. Because the haploid human cells can be engineered with desired homozygosity and immunogenicity properties, they are also useful for therapeutic purposes, such as in regenerative medicine. The genomes of haploid parthenogenetic ES cells or of haploid differentiated human cells could potentially be used in human reproduction, to replace the genome of an oocyte.

Importantly, the haploid human cells of the invention are useful in genetic screening, preferably forward genetics. One example is in homozygote loss-of-function screens to identify targets of various diseases, and in drug screens to identify candidate compounds for treating these diseases. A genetic screen can include the use of a mutagen to introduce one or more mutations into haploid human cells. Mutagens suitable for use in the present invention include physical mutagens, such as ionizing radiation (X-rays, gamma rays, ultraviolet rays, etc.); chemical mutagens, such as alkylating agents; and biological agents, such as plasmid, phage, or viral vectors. Examples of biological agents include insertional vectors, for example, gene trap vectors, and technologies for site-directed mutagenesis, such as zinc-finger nucleases (ZFNs), transcription activator-like effector nucleases (TALENs), or the CRISPR/Cas9 system.

As used in this specification and the appended claims, the singular forms "a," "an," and "the" include plural referents, unless the context clearly dictates otherwise. The terms "a" (or "an") as well as the terms "one or more" and "at least one" can be used interchangeably.

Furthermore, "and/or" is to be taken as specific disclosure of each of the two specified features or components with or without the other. Thus, the term "and/or" as used in a phrase such as "A and/or B" is intended to include A and B, A or B, A (alone), and B (alone). Likewise, the term "and/or" as used in a phrase such as "A, B, and/or C" is intended to include A, B, and C; A, B, or C; A or B; A or C; B or C; A and B; A and C; B and C; A (alone); B (alone); and C (alone).

Unless defined otherwise, all technical and scientific terms used herein have the same meaning as commonly understood by one of ordinary skill in the art to which this invention is related. For example, The Dictionary of Cell and Molecular Biology (5th ed. J. M. Lackie ed., 2013), the Oxford Dictionary of Biochemistry and Molecular Biology (2d ed. R. Cammack et al. eds., 2008), and The Concise Dictionary of Biomedicine and Molecular Biology (2d ed. P-S. Juo, 2002) can provide one of skill with general definitions of some terms used herein.

Units, prefixes and symbols are denoted in their Systeme International de Unites (SI) accepted form. Numeric ranges are inclusive of the numbers defining the range. The headings provided herein are not limitations of the various aspects or embodiments of the invention, which can be had by reference to the specification as a whole. Accordingly, the terms defined immediately below are more fully defined by reference to the specification in its entirety.

Wherever embodiments are described with the language "comprising," otherwise analogous embodiments described in terms of "consisting of" and/or "consisting essentially of" are included.

All of the references cited in this disclosure are hereby incorporated by reference in their entireties. In addition, any manufacturers' instructions or catalogues for any products cited or mentioned herein are incorporated by reference. Documents incorporated by reference into this text, or any teachings therein, can be used in the practice of the present invention. Documents incorporated by reference into this text are not admitted to be prior art.

The invention is further described in the following non-limiting Examples.

EXAMPLES

Example 1. Methods

Human Oocyte Manipulation and Parthenogenetic ES Cell Line Derivation.

Human oocyte donation and pES and swaPS cell line derivation procedures were described previously.15,35 Briefly, mature MII oocytes were activated using a calcium ionophore and/or an electrical pulse, followed by 4 hour culture with puromycin. Polar body extrusion and the presence of a single pronucleus indicating haploidy were confirmed, and oocytes were allowed to develop to the blastocyst stage. swaPS cells were derived following activation of an oocyte whose nuclear genome had been swapped with that of another oocyte.15 ES cell lines were derived by laser-ablation of the trophectoderm38 and addition of ROCK inhibitor Y-27632 at 10 μM to the derivation medium.35 Two to three days after plating, remaining trophectoderm cells were laser-ablated, and ICM cells were allowed to grow for 10-14 days until manual picking of the outgrowth was feasible.

Cell Culture.

Unless otherwise stated, human ES cells were cultured on a feeder layer of growth-arrested mouse embryonic fibroblasts in standard human ES cell medium composed of Knockout Dulbecco's Modified Eagle's Medium supplemented with 15% Knockout Serum Replacement (KSR, Thermo Fisher Scientific), 2 mM 1-glutamine, 0.1 mM nonessential amino acids, 50 units mL-1 penicillin, 50 μg mL-1 streptomycin, 0.1 mM β-mercaptoethanol and 8 ng mL-1 basic fibroblast growth factor (bFGF). Cells were free of mycoplasma and maintained in a humidified incubator at 37° C. and 5% CO2. Passaging was carried out either mechanically with gentle trypsinization using Trypsin Solution A without EDTA (Biological Industries), or enzymatically using TrypLE Express (Thermo Fisher Scientific) with addition of 10 μM ROCK inhibitor Y-27632 (Stemgent) for 1 day or up to 2 days after splitting. Haploid ES cells could also be grown in feeder-free conditions on Matrigel-coated plates (Corning) in mTeSR1 (STEMCELL Technologies) or StemFitN.AK03 (Ajinomoto) media. Rapid expansion of the outgrowth allows isolation of haploid ES cells as early as passage 3.

Isolation and Maintenance of Haploid Human ES Cell Lines.

Following identification of haploid cells in human parthenogenetic ES cell lines at passages 6-8 by either metaphase spread analysis or sub-2c cell sorting (Table 1 and Table 2), haploid ES cell lines were established by sorting the 1c cell population, with diploid cells serving as a reference. Haploid ES cell cultures were further maintained by enrichment rounds of 1c cell sorting every 3-4 passages.

TABLE 1

Identification of haploid cells in early-passage human parthenogenetic ES cell lines by metaphase spread analysis

| pES cell line | Oocyte donor | Passage no. at analysis | No. of haploid metaphases | No. of diploid metaphases | Total no. of metaphases | % Haploid metaphases |
|---|---|---|---|---|---|---|
| 1 | 8/31/09 | 4 | 0 | 233 | 233 | 0 |
| 2 | 1043 | 6 | 0 | 278 | 278 | 0 |
| 3 | 1058 | 6 | 0 | 273 | 273 | 0 |
| 4 | 1058 | 6 | 0 | 222 | 222 | 0 |
| 5 | 1058 | 9 | 0 | 50 | 50 | 0 |
| 6 | 1105 | 5 | 0 | 13 | 13 | 0 |
|  |  | 10 | 0 | 140 | 140 | 0 |
| 8 | 1151 | 4 | 0 | 361 | 361 | 0 |
| 9 | 1157 | 6 | 0 | 234 | 234 | 0 |
| 10 | 1160 | 7 | 2 | 150 | 152 | 1.32 |
| 11 | 1160 | 8 | 0 | 194 | 194 | 0 |
|  |  | Total: | 2 | 2148 | 2150 |  |

The derivation of cell lines pES1-6 was reported previously.15,35

TABLE 2

Isolation of haploid cells from early-passage human parthenogenetic ES cell lines by sub-2c cell sorting

| | Oocyte donor | Passage number at 1st sort | Passage number at 2nd sort | Presence of haploid cells at 2nd sort |
|---|---|---|---|---|
| pES cell line | | | | |
| 6 | 1105 | 6 | 10 | Undetected |
| 12 | 1160 | 6 | 10 | Yes |
| swaPS cell line* | | | | |
| 4 | 1126 | 6 | 11 | Undetected |
| 5 | 1155 | 5 | 9 | Undetected |
| 11 | 1175 | 4 | | Sorted population did not survive |

*swaPS cells are parthenogenetic ES cells derived following activation of an oocyte whose nuclear genome had been swapped with that of another oocyte.35

Metaphase Spread Analysis.

For induction of mitotic arrest, growing cells were incubated for 40 min in the presence of 100 ng mL-1 colcemid (Biological Industries), added directly to the culture medium, in a humidified incubator at 37° C. with 5% CO2. The cells were then trypsinized, centrifuged at 1000 RPM at room temperature and gently resuspended in 37° C.-warmed hypotonic solution (2.8 mg mL-1 KCl and 2.5 mg mL-1 sodium citrate) followed by 20-min incubation at 37° C. Cells were fixed by addition of fixative solution (3:1 methanol:acetic acid) and incubation for 5 min at room temperature. Fixation was repeated at least three times following centrifugation and resuspension in fixative solution. Metaphase spreads were prepared on slides and stained using the standard G-banding technique. Karyotype integrity was determined according to the International System for Human Cytogenetic Nomenclature (ISCN) based on the observation of a normal karyotype in at least 80% of analyzed metaphases (minimum of 20 metaphases per analysis).

Live ES Cell Sorting by DNA Content.

Cells were washed with phosphate buffered saline (PBS), dissociated using either TrypLE Select or TrypLE Express (Thermo Fisher Scientific) and stained with 10 mL-1 Hoechst 333422 (Sigma-Aldrich) in human ES cell medium at 37° C. for 30 min. Following centrifugation, cells were resuspended in PBS containing 15% KSR and 10 ROCK inhibitor Y-27632, filtered through a 70-μm cell strainer (Corning) and sorted using the 405 nm laser in either BD FACSAria III or BD Influx (BD Biosciences). For continued growth, sorted cells were plated with fresh medium containing 10 μM ROCK inhibitor Y-27632 for 24 hours. For comparative analyses, G1-phase cells were sorted from isogenic haploid-enriched and unsorted diploid cultures. Cells that had undergone diploidization relatively recently in culture (within 3 passages after haploid cell enrichment) were isolated by sorting the G2/M-phase peak in haploid-enriched cultures and compared with G2/M-phase diploid cells from unsorted diploid cultures. Note that haploid-enriched cultures also consist of a mixed population of G2/M-phase haploids and G1-phase diploids. Sorting purity was confirmed by rerunning a fraction of sorted samples through the instrument.

Flow Cytometry.

All DNA content profiles were generated based on flow cytometry with Hoechst 33342 staining. Haploid cell proportion was estimated based on the percentage of 1c cells and the relative contribution of G1 cells with regards to other phases of the cell cycle. Estimation of diploidization rate was based on the proportion of haploid cells between consecutive enrichment rounds as well as experimental analysis of h-pES10 diploidization kinetics throughout 7 passages (30 days) by analyzing the DNA content of 2-3 replicates at each passage using flow cytometry with propidium iodide in methanol-fixed and RNase-treated cells. Diploidization rate was estimated by fitting the data to an exponential decay curve. For simultaneous flow cytometry analysis of DNA content and cell surface molecules, cells were washed, dissociated and incubated on ice for 30 min in the presence of 10 μg mL$^{-1}$ Hoechst 33342 (Sigma-Aldrich) and either a conjugated antibody or a secondary antibody diluted 1:200 following a 60 min incubation with a primary antibody. For simultaneous flow cytometry analysis of DNA content and intracellular PDX1, dissociated cells were treated as described for immunofluorescence procedures, with Hoechst 33342 for DNA staining. Primary antibodies are detailed in Table 3. In all flow cytometry procedures, samples were filtered through a 70-μm cell strainer (Corning Life Sciences) and analyzed in either BD FACSAria III or BD Influx (BD Biosciences).

TABLE 3

Primary antibodies used in the Examples

| Antibody | Host species | Type | Isotype | Dilution | Vendor | Catalog no. | Assay |
|---|---|---|---|---|---|---|---|
| Anti-centromere | Human | Polyclonal | NA | 1:50 | Antibodies Incorporated | 15-235-0001 | IF |
| Anti-pH3 | Rabbit | Polyclonal | NA | 1:1,000 | EMD Millipore | 06-570 | IF |
| Anti-human NANOG | Goat | Polyclonal | IgG | 1:100 | R&D Systems | AF1997 | IF |
| Anti-human OCT4 | Goat | Polyclonal | IgG | 1:100 | Santa Cruz Biotechnology | sc-8628 | IF |
| Anti-human SOX2 | Rabbit | Polyclonal | IgG | 1:100 | Stemgent | 09-0024 | IF |
| Anti-human/mouse SSEA4 | Mouse | Monoclonal | IgG | 1:500 | R&D Systems | MAB1435 | IF |
| Alexa Fluor ® 488-conjugated anti-human TRA-1-60 | Mouse | NA | IgM | 1:100 | BD Biosciences | 560173 | IF |
| PE-conjugated anti-human TRA-1-60 | Mouse | Monoclonal | IgM | 1:40 | BD Biosciences | 560884 | FC |
| Anti-human CLDN6 | Mouse | Monoclonal | IgG | 1:40 | R&D Systems | MAB3656 | FC |
| Anti-H3K27me3 | Rabbit | Polyclonal | IgG | 1:400 | EMD Millipore | 07-449 | IF |
| Anti-human NCAM-1/CD56 | Goat | Polyclonal | IgG | 1:150 | R&D Systems | AF2408 | FC |
| Anti-human FOXA2 | Rabbit | Polyclonal | NA | 1:200 | Cell Signaling Technology | 3143 | IF |
| Anti-human TUJ1 | Rabbit | NA | NA | 1:300 | Sigma-Aldrich | T2200 | IF |
| Anti-human TNNT2 | Rabbit | Polyclonal | IgG | 1:100 | Abcam | ab45932 | IF |
| Anti-human NKX6.1 | Mouse | Monoclonal | IgG | 1:300 | DSHB | F55A10 | IF |
| Anti-human PDX1 | Goat | Polyclonal | IgG | 1:200 | R&D Systems | AF2419 | IF, FC |
| Anti-human NKX6.1 | Mouse | Monoclonal | IgG | 1:300 | DSHB | F55A10 | IF |
| Anti-human α-SMA | Mouse | Monoclonal | IgG | 1:500 | Dako | M0851 | IF |
| Anti-human AFP | Rabbit | Polyclonal | NA | 1:500 | Dako | A0008 | IF |

NA: not available.
IF: immunofluorescence staining.
FC: flow cytometry.

DNA Fluorescence In Situ Hybridization.

DNA FISH was performed as described elsewhere39 using probes for human chromosomes 2 and 4 and DNA staining with 4',6-diamidino-2-phenylindole (DAPI). Haploidy and diploidy were respectively determined per nucleus based on single or double hybridization signals. ES cells subject to FISH were grown on Matrigel-coated MATEK glass plates for several passages prior to analysis.

Alkaline phosphatase and immunofluorescence staining.

Alkaline phosphatase staining was performed using the Leukocyte Alkaline Phosphatase Kit (Sigma-Aldrich). For immunofluorescence staining, samples were washed with PBS, fixed with 4% paraformaldehyde for 10 min, and permeabilized and blocked in blocking solution (0.1% Triton X-100 and 5% donkey serum in PBS). Cells were incubated with primary antibodies (Table 3) and secondary antibodies diluted 1:500 in blocking solution, and DAPI was used for DNA staining. Cells were washed twice with PBS subsequently to fixation and each incubation step. Images were taken using a Zeiss LSM 510 Meta Confocal Microscope. Centromere quantification was carried out by manually counting centromere foci across individual planes along the Z axis. EdU staining was performed using the Click-iT EdU Alexa Fluor 488 Imaging Kit (Thermo Fisher Scientific). ES cells subject to centromere staining in FIG. 1g and FIG. 5d were grown on Matrigel-coated MATEK glass plates for several passages prior to analysis.

6-TG Resistance Screen

To generate a gene trap mutant library, 9 replicates of 4-5×106 haploid pES10 cells (within one passage after 1c-cell enrichment) were co-transfected with 20 µg 5'-PTK-3' gene trap vector52 and 20 µg pCyL43 piggyBac transposase plasmid53 using Bio-Rad Gene Pulser (suspended in 800 µL Opti-MEM, 4-mm cuvettes, 320 V, 250 µF), and replated on a 100×20 mm dish with DR3 MEFs and ROCK inhibitor Y-27632. Selection for insertions into expressed loci was carried out using 0.3 µg mL$^{-1}$ puromycin starting 48 hours post transfection, followed by pooling into a single library, represented by approximately 16,000 resistant colonies. Transfection with 5'-PTK-3' only was used as a negative control. To screen for 6-TG-resistant mutants, the mutant library was grown in the presence of 6 µM 6-TG (Sigma-Aldrich) on DR4 MEFs for 18 days, during which 6 resistant colonies were independently isolated and characterized. Genomic DNA was extracted (NucleoSpin Tissue Kit, MACHEREY-NAGEL) and insertion sites were detected using splinkerette PCR as described previously,54 followed by PCR product purification and Sanger sequencing (ABI PRISM 3730×1 DNA Analyzer (Applied Biosystems)). Sequences were mapped to the human genome (GRCh38/hg38) using UCSC BLAT search tool.

Isolation of Total DNA and RNA.

Total DNA was isolated using the NucleoSpin Tissue Kit (MACHEREY-NAGEL). Total RNA was isolated using Qiagen RNeasy Kits according to the manufacturer's protocols. To determine total RNA levels per cell, haploid and diploid cells were isolated from the same cultures by sorting the 1c (haploid G1) and 4c (diploid G2/M) populations, respectively. Following growth for 2 passages, cells were harvested and counted, and RNA was isolated from triplicates of 400,000 cells from each cell line and ploidy state (pES10 and pES12, haploid and diploid; 12 samples in total). RNA amounts were quantified using NanoDrop.

Genome Integrity Analysis.

Copy number variation (CNV) analysis was carried out on DNA samples of G1-sorted haploid and diploid pES10 and pES12 cells (Table 4) using Infinium Omni2.5Exome-8 BeadChip single nucleotide polymorphism (SNP) arrays (Illumina) following the manufacturer's protocols. Raw data were processed using Genome Studio Genotyping Module (Illumina) to obtain log R ratios values for analysis using R statistical programming language.

TABLE 4

Samples analyzed by SNP arrays and DNA methylation arrays

| Sample no. | Sample name | Cell line | Passage | Description | Assay* |
|---|---|---|---|---|---|
| 1 | pES10 h-G1 rep1 | h-pES10 | 15 | Haploid ES cells in G1 (1c), 3$^{rd}$ sort, biological replicate 1 | M, S |
| 2 | pES10 h-G1 rep2 | h-pES10 | 19 | Haploid ES cells in G1 (1c), 4$^{th}$ sort, biological replicate 2 | M |
| 3 | pES10 d-G1 rep1 | d-pES10 | 17 | Diploid ES cells in G1 (2c), technical replicate 1 | M, S |
| 4 | pES10 d-G1 rep2 | d-pES10 | 17 | Diploid ES cells in G1 (2c), technical replicate 2 | M |
| 5 | h-pES10 d-G2/M | h-pES10 | 15 | Diploid ES cells in G2/M from a mixed haploid-diploid culture (4c), 3$^{rd}$ sort | M |
| 6 | pES12 h-G1 rep1 | h-pES12 | 18 | Haploid ES cells in G1 (1c), 4$^{th}$ sort, biological replicate 1 | M, S |
| 7 | pES12 h-G1 rep2 | h-pES12 | 22 | Haploid ES cells in G1 (1c), 5$^{th}$ sort, biological replicate 2 | M |
| 8 | pES12 d-G1 rep1 | d-pES12 | 18 | Diploid ES cells in G1 (2c), biological replicate 1 | M, S |
| 9 | pES12 d-G1 rep2 | d-pES12 | 18 | Diploid ES cells in G1 (2c), biological replicate 2 | M |
| 10 | NYSCF2 | NYSCF2 | 20 | Diploid IVF ES cell line | M |
| 11 | HuES53 | HuES53 | <20 | Diploid IVF ES cell line | M |
| 12 | HuES64 | HuES64 | <20 | Diploid IVF ES cell line | M |

*M: DNA methylation analysis. S: SNP array analysis.

RNA Sequencing.

Total RNA samples (200 ng-1 µg, RNA integrity number (RIN)>9) were enriched for mRNAs by pull-down of poly (A)$^+$ RNA. RNA-Seq libraries were prepared using the TruSeq RNA Library Prep Kit v2 (Illumina) according to the manufacturer's protocol and sequenced using Illumina NextSeq 500 to generate 85 bp single-end reads.

Table 5 provides a detailed list of samples analyzed by RNA-Seq.

TABLE 5

Samples analyzed by RNA-Seq

| Sample no. | Sample name | Cell line | Passage | Description |
|---|---|---|---|---|
| 1 | pES10 h-G1 rep1 | h-pES10 | 15 | Haploid ES cells in G1 (1c), 3$^{rd}$ sort, biological replicate 1 |
| 2 | pES10 h-G1 rep2 | h-pES10 | 19 | Haploid ES cells in G1 (1c), 4$^{th}$ sort, biological replicate 2 |
| 3 | pES10 d-G1 rep1 | d-pES10 | 13 | Diploid ES cells in G1 (2c), biological replicate 1 |
| 4 | pES10 d-G1 rep2 | d-pES10 | 17 | Diploid ES cells in G1 (2c), biological replicate 2 |
| 5 | h-pES10 d-G2/M | h-pES10 | 15 | Diploid ES cells in G2/M from a mixed haploid-diploid culture (4c), 3$^{rd}$ sort |
| 6 | d-pES10 d-G2/M | d-pES10 | 13 | Diploid ES cells in G2/M from a diploid culture (4c) |
| 7 | pES12 h-G1 rep1 | h-pES12 | 18 | Haploid ES cells in G1 (1c), 4$^{th}$ sort, biological replicate 1 |
| 8 | pES12 h-G1 rep2 | h-pES12 | 22 | Haploid ES cells in G1 (1c), 5$^{th}$ sort, biological replicate 2 |
| 9 | pES12 d-G1 rep1 | d-pES12 | 18 | Diploid ES cells in G1 (2c), biological replicate 1 |
| 10 | pES12 d-G1 rep2 | d-pES12 | 18 | Diploid ES cells in G1 (2c), biological replicate 2 |
| 11 | pES10 NPC h-G1 | h-pES10 | 21 | Haploid NCAM1$^+$ NPCs in G1 (1c) derived from ES cells after 4$^{th}$ sort + 10 days culture + 10 days differentiation |
| 12 | pES10 EB h-G1 | h-pES10 | 25 | Haploid EB cells in G1 (1c) derived from ES cells after the 5$^{th}$ sort + 13 days culture + 21 days differentiation |
| 13 | pES10 EB d-G1 | d-pES10 | 12 | Diploid EB cells in G1 (2c) derived from ES cells after 21 days differentiation |
| 14 | pES10 EB d-unsorted | d-pES10 | 12 | Unsorted diploid EBs derived from ES cells after 21 days differentiation |
| 15 | pES12 EB d-unsorted | d-pES12 | 19 | Unsorted diploid EBs derived from ES cells after 21 days differentiation |
| 16 | HuES53 | HuES53 | <20 | Diploid IVF ES cell line |
| 17 | HuES64 | HuES64 | <20 | Diploid IVF ES cell line |

Transcriptome Analysis.

RNA-Seq reads were aligned to the human reference genome (GRCh37/hg19) using TopHat (version 2.0.8b) allowing 5 mismatches. Reads per kilobase per million fragments mapped (RPKM) values were quantified using Cuffquant and normalized using Cuffnorm in Cufflinks (version 2.1.1) to generate relative gene expression levels. Hierarchical clustering analyses were performed on RPKM values using Pearson correlation and average linkage. Analysis of differential gene expression relative to total RNA in haploid and diploid human ES cells (n=4 in each group) was carried out by two complementary strategies, as follows: first, we used Cuffdiff with default parameters, considering differences of >2-fold with FDR<0.05 as significant; second, to identify possibly subtle yet consistent transcriptional differences, we tested for genes whose minimal expression levels across all replicates of a certain group were higher than their maximal expression level across all replicates of the other group. Statistical significance was then determined by two-tailed unpaired Student's t test. Functional annotation enrichment analysis was done by DAVID (using the Benjamini method to determine statistical significance). Imprinting analyses included 75 human imprinted genes (see the Geneimprint website), listed in Table 6. RNA-Seq data from control ES cell line NYSCF1 were published elsewhere[37] (GEO accession number GSE61657). Genome-wide gene expression moving median plots were generated using the R package zoo (version 1.7-12) after removal of genes that were not expressed in the averaged reference diploid sample by flooring to 1 and setting an expression threshold of above 1. RNA-Seq data from different tissues were retrieved from the Genotype-Tissue Expression (GTEx) Portal.[40] Color-coded scales in FIG. 4d correspond to gene expression levels relative to the mean across tissues (left scale) and across each set of ES cell duplicate and EB sample (right scale). Expression microarray analysis was performed as previously[41] by using Affymetrix Human Gene 1.0 ST arrays.

TABLE 6

Imprinted genes used for hierarchical clustering analysis

| Gene | ID | Locus |
|---|---|---|
| TP73 | ENSG00000078900 | chr1: 3547330-3663900 |
| RNU5D-1 | ENSG00000200169 | chr1: 45196726-45196842 |
| DIRAS3 | ENSG00000162595 | chr1: 68167148-68698803 |
| LRRTM1 | ENSG00000162951 | chr2: 79384131-80875905 |
| GPR1 | ENSG00000183671 | chr2: 207040039-207082771 |
| ZDBF2 | ENSG00000204186 | chr2: 207139386-207179148 |
| NAP1L5 | ENSG00000177432 | chr4: 89442135-89629693 |
| FAM50B | ENSG00000145945 | chr6: 3832166-3855971 |
| LIN28B | ENSG00000187772 | chr6: 105404922-105531207 |
| AIM1 | ENSG00000112297 | chr6: 106959729-107018326 |
| PLAGL1 | ENSG00000118495 | chr6: 144261436-144385735 |
| SLC22A2 | ENSG00000112499 | chr6: 160592092-160698670 |
| SLC22A3 | ENSG00000146477 | chr6: 160769299-160932156 |
| DDC | ENSG00000132437 | chr7: 50526133-50633154 |
| GRB10 | ENSG00000106070 | chr7: 50657759-50861159 |
| MAGI2 | ENSG00000187391 | chr7: 77646392-79100524 |
| TFPI2 | ENSG00000105825 | chr7: 93220884-93540577 |
| SGCE | ENSG00000127990 | chr7: 94214541-94285521 |
| PEG10 | ENSG00000242265 | chr7: 94285636-94299007 |
| PPP1R9A | ENSG00000158528 | chr7: 94536513-94925727 |
| DLX5 | ENSG00000105880 | chr7: 96649703-96654409 |
| CPA4 | ENSG00000128510 | chr7: 129932973-129964020 |
| MEST | ENSG00000106484 | chr7: 130125882-130148500 |
| KLF14 | ENSG00000174595 | chr7: 130417400-130418888 |
| DLGAP2 | ENSG00000198010 | chr8: 1449531-1656642 |
| ZFAT | ENSG00000066827 | chr8: 135490030-135725292 |
| ZFAT-AS1 | ENSG00000248492 | chr8: 135490030-135725292 |
| KCNK9 | ENSG00000169427 | chr8: 140613080-140715299 |
| GLIS3 | ENSG00000107249 | chr9: 3824126-4348392 |
| INPP5F | ENSG00000198825 | chr10: 121485608-121588652 |
| H19 | ENSG00000130600 | chr11: 2016405-2022700 |
| IGF2 | ENSG00000167244 | chr11: 2150341-2182571 |
| IGF2-AS | ENSG00000099869 | chr11: 2150341-2182571 |
| INS | ENSG00000254647 | chr11: 2150341-2182571 |

TABLE 6-continued

Imprinted genes used for hierarchical clustering analysis

| Gene | ID | Locus |
|---|---|---|
| KCNQ1 | ENSG00000053918 | chr11: 2465913-2882798 |
| KCNQ1OT1 | ENSG00000269821 | chr11: 2465913-2882798 |
| KCNQ1DN | ENSG00000237941 | chr11: 2891262-2893335 |
| CDKN1C | ENSG00000129757 | chr11: 2904442-2907111 |
| SLC22A18 | ENSG00000110628 | chr11: 2909009-2946476 |
| PHLDA2 | ENSG00000181649 | chr11: 2949502-2950685 |
| OSBPL5 | ENSG00000021762 | chr11: 3108345-3187969 |
| WT1 | ENSG00000184937 | chr11: 32409320-32480315 |
| ANO1 | ENSG00000131620 | chr11: 69924407-70035634 |
| ZC3H12C | ENSG00000149289 | chr11: 109964086-110042566 |
| NTM | ENSG00000182667 | chr11: 131240372-132206716 |
| RBP5 | ENSG00000139194 | chr12: 7276279-7281538 |
| RB1 | ENSG00000139687 | chr13: 48877886-49056122 |
| DLK1 | ENSG00000185559 | chr14: 101192041-101201539 |
| MEG3 | ENSG00000214548 | chr14: 101245746-101327368 |
| RTL1 | ENSG00000254656 | chr14: 101346991-101351184 |
| MKRN3 | ENSG00000179455 | chr15: 23810453-23873064 |
| MAGEL2 | ENSG00000254585 | chr15: 23888690-23891175 |
| NDN | ENSG00000182636 | chr15: 23930564-23932450 |
| NPAP1 | ENSG00000185823 | chr15: 24920540-24928593 |
| SNRPN | ENSG00000128739 | chr15: 25068793-25492435 |
| SNURF | ENSG00000273173 | chr15: 25068793-25492435 |
| UBE3A | ENSG00000114062 | chr15: 25497371-25684128 |
| ATP10A | ENSG0000206190 | chr15: 25922419-26110317 |
| NAA60 | ENSG00000262621 | chr16: 3415098-3627401 |
| ZNF597 | ENSG00000167981 | chr16: 3415098-3627401 |
| TCEB3C | ENSG00000183791 | chr18: 44388352-44627658 |
| DNMT1 | ENSG00000130816 | chr19: 10244020-10341962 |
| MIR371A | ENSG00000199031 | chr19: 54290850-54291423 |
| NLRP2 | ENSG00000022556 | chr19: 55434876-55512510 |
| PEG3 | ENSG00000198300 | chr19: 57202053-57352097 |
| ZIM2 | ENSG00000269699 | chr19: 57202053-57352097 |
| MIMT1 | ENSG00000268654 | chr19: 57352269-57359924 |
| BLCAP | ENSG00000166619 | chr20: 36120873-36156333 |
| NNAT | ENSG00000053438 | chr20: 36120873-36156333 |
| MIR296 | ENSG00000268649 | chr20: 57392186-57392780 |
| MIR298 | ENSG00000216031 | chr20: 57393280-57393368 |
| GNAS | ENSG00000087460 | chr20: 57393973-57486247 |
| GNAS-AS1 | ENSG00000235590 | chr20: 57393973-57486247 |
| DGCR6 | ENSG00000183628 | chr22: 18893540-18924066 |
| DGCR6L | ENSG00000128185 | chr22: 20301798-20307603 |

DNA Methylation Analysis.

DNA methylation analysis was performed on genomic DNA from the samples detailed in Table 4 using Infinium HumanMethylation450 BeachChips (Illumina) following the Infinium HD Methylation Protocol as described previously.[37] DNA methylation data from control ES cell line NYSCF1 were published before (GEO accession number GSE61657).[37] Data were processed and normalized by using subset-quantile within array normalization (SWAN) and adjusted for batch effects using the R package ChAMP (version 1.4.0). DNA methylation levels at CpG sites associated with pluripotency-specific genes and iDMRs were analyzed as described before.[37] For analysis of DNA methylation levels on the X chromosome, probes with average β values of less than 0.4 were filtered out. DMR analysis was facilitated by the lasso function in ChAMP using default settings. DMRs were then assigned to genes by proximity and analyzed for functional annotation enrichment using DAVID (using the Benjamini method to determine statistical significance).

Cell Size Analysis.

Following sorting of haploid and diploid cell populations in G1, the diameter (2r) of viable single cells was measured by Countess Automated Cell Counter (Invitrogen) and their surface area and volume were calculated as $4\pi r^2$ and $4\pi r^3$, respectively. Analysis included 7, 4, 8 and 4 technical replicates for 1n pES10, 1n pES12, 2n pES10 and 2n pES12, respectively.

Mitochondrial DNA Abundance Analysis.

Relative mtDNA abundance was analyzed by quantitative PCR (qPCR) by using primers for the mitochondrial gene ND2 (forward primer: 5'-TGTTGGT-TATACCCTTCCCGTACTA-3' (SEQ ID NO: 1); reverse primer: 5'-CCTGCAAAGATGGTAGAGTAGATGA-3' (SEQ ID NO: 2)) and normalization to nuclear DNA by using primers for the nuclear gene BECN1 (forward primer: 5'-CCCTCATCACAGGGCTCTCTCCA-3' (SEQ ID NO: 3); reverse primer: 5'-GGGACTGTAGGCTGGGAAC-TATGC-3' (SEQ ID NO: 4)), as described elsewhere.[42] Analysis was performed using Applied Biosystems 7300 Real-Time PCR System with PerfeCTa SYBR Green Fast-Mix (Quanta Biosciences). Analysis included all G1-sorted samples detailed in Table 4 (n=4 for each group, with two biological replicates for each cell line).

All high-throughput data have been deposited at the Gene Expression Omnibus (GEO) under accession number GSE71458.

Embryoid Body Differentiation.

EB differentiation was carried out by detaching ES cell colonies with Trypsin Solution A without EDTA (Biological Industries), followed by resuspension and further culture of cell aggregates in human ES cell medium without bFGF on low attachment plates. Differentiation of haploid ES cells was initiated within 2 passages after 1c-cell enrichment. After 21 days, EB RNA was extracted from unsorted and/or sorted EB cells in G1 following dissociation and staining with 10 μg mL-1 Hoechst 33342 (Sigma-Aldrich) at 37° C. for 30 min. Metaphase spread analysis was performed on dissociated EB cells plated on 0.2% gelatin and expanded in human ES cell medium without bFGF.

Differentiation into Neural Progenitor Cells.

NCAM1-positive ES cell-derived NPCs were obtained using a 10-days protocol for efficient neural differentiation[43] with slight modification.[44] Differentiation was initiated within 2 passages after 1c-cell enrichment. RNA was extracted from sorted haploid NCAM1-positive cells in G1 by co-staining with Hoechst 33342 and an anti-human NCAM-1/CD56 primary antibody and a Cy3-conjugated secondary antibody (Jackson Immunoresearch Laboratories) diluted 1:200.

Neuronal Differentiation.

Differentiation into neurons was carried out by following a published protocol[45] based on synergistic inhibition of SMAD signaling[46] with modification, as follows: differentiation was initiated within 2 passages after 1c-cell enrichment with fully confluent ES cells cultured on Matrigel-coated plates in mTeSR1 by replacing the medium with human ES cell medium without bFGF, containing 10 μM SB431542 (Selleckchem) and 2.5 μM LDN-193189 (Stemgent) for 4 days. Subsequently, cells were kept in N2 medium[45] supplemented with 10 μM SB431542 and 2.5 μM LDN-193189 for additional 4 days, followed by 2 days in N2 medium supplemented with B-27 (Thermo Fisher Scientific) and 10 μM DAPT (Stemgent). The cells were then dissociated and replated on 0.01% poly-1-ornithine-(Sigma-Aldrich) and laminin-coated (4 μg/ml, Thermo Fisher Scientific) plates in the presence of 10 μM ROCK inhibitor Y-27632 (Selleckchem), and further cultured in the same medium without Y-27632 for the next 4 days. Neuronal cultures were maintained in N2 medium supplemented with B-27 and 20 ng-1 BDNF (R&D) until analysis by immunostaining and FISH on day 20.

Cardiomyocyte Differentiation.

80-90% confluent ES cells grown on Matrigel-coated plates (Corning) in mTeSR1 (STEMCELL Technologies)

were subject to an 11-days regimen47 based on consecutive GSK3 and WNT inhibition with CHIR99021 and IWP-2 (Selleckchem), respectively. Differentiation was initiated within 2 passages after 1c-cell enrichment. On day 11 of differentiation, 1c-cells were sorted and plated for immunostaining.

Differentiation Toward the Pancreatic Lineage.

The protocol utilized here was developed based on several recent publications.48-50 ES cells grown in feeder-free conditions were differentiated into definitive endoderm by using STEMdiff Definitive Endoderm Kit (Stemcell Technologies) for 3-4 days. Subsequent specification was achieved by a step-wise protocol involving treatment with recombinant human KGF/FGF7 (R&D Systems), LDN-193189 (Stemgent), KAAD-cyclopamine (Stemgent) and retinoic acid (Stemgent). On days 8-11, EGF (R&D System) was used to induce pancreatic progenitor cells (PPCs). Differentiation was initiated within 2 passages after 1c-cell enrichment.

Teratoma Formation Assay.

All experimental procedures in animals were approved by the ethics committee of the Hebrew University. ES cells were trypsinized and approximately 2×106 cells were resuspended in 100 µL human ES cell medium and 100 µL Matrigel (BD Biosciences), followed by subcutaneous injection into NOD-SCID Il2rg−/− immunodeficient mice (Jackson Laboratory). Eight to twelve weeks after injection, tumors were dissected and subjected to further analysis. Histological slides were prepared from tumor slices cryopreserved in O.C.T. compound (Sakura Finetek) using Leica CM1850 cryostat (Leica Biosystems, 10-µm sections), followed by immunostaining, hematoxylin and eosin staining or FISH analysis. Flow cytometry with Hoechst 33342 staining was performed on dissociated cells from freshly dissected tumors.

Example 2. Determination of Ploidy at Single-Cell Level by Quantification of Centromere Foci We devised a methodology for determining ploidy at single-cell resolution based on centromere protein immunofluorescence staining. As each chromosome normally has one centromere, we reasoned that being able to detect and enumerate centromeres would provide a means to visualize ploidy in individual cells, while also allowing to define cellular identity by co-staining for specific markers.

We first tested this method on cell lines of known ploidies, including haploid-enriched and diploid pES10 cells, triploid soPS2 cells35 and tetraploid Hybrid1 cells,36 demonstrating a correlation between ploidy and the counted number of centromeres (FIG. 6a). Centromere counts were within with the expected range of chromosome number. 76% of the haploid-enriched cells showed 15-25 centromere foci, whereas the remaining cells showed 30-48 foci, similar to the range documented in diploid cells (34-51). Importantly, this percentage of haploid cells was consistent with that estimated by DNA FISH (73%, FIG. 6b) and DNA content flow cytometry (73%, FIG. 6c), indicating that centromere foci quantification is a reliable method for identifying haploid ES cells.

The accuracy of counting centromeres decreased with increasing ploidy, due to centromere clustering, which would lead to an underestimation of the actual number of individual centromeres, as well as difficulties in counting large numbers of centromeres in single cells. Observing higher numbers of foci than expected could be explained by visual artifacts or aneuploidy in rare cells. To address whether cell cycle progression altered centromere foci numbers or affected their quantification, we co-stained haploid ES cells for centromere protein and either phospho-histone 3 (pH3, Ser10) or 5-ethynyl-2'-deoxyuridine (EdU) (marking cells entering mitosis and undergoing DNA replication, respectively), to quantify the number of centromeres at different stages of the cell cycle (FIG. 6d-6f). Evidently, centromere foci numbers did not increase during DNA replication, confirming that haploid cells can be accurately detected throughout interphase by centromere staining.

Example 3. Derivation of Haploid Human ES Cells

We generated and analyzed a collection of 14 early-passage (passage≤9) human pES cell lines for the persistence of haploid cells. All cell lines originated from activated oocytes displaying second polar body extrusion and a single pronucleus. We initially utilized chromosome counting by metaphase spreading and G-banding as a method for unambiguous and quantitative discovery of rare haploid nuclei. Among ten individual pES cell lines, a low proportion of haploid metaphases was found exclusively in a single cell line, pES10 (1.3%, Table 1). We also used viable FACS with Hoechst 33342 staining, aiming to isolate cells with a DNA content corresponding to less than two chromosomal copies (2c) from four additional lines, leading to the successful enrichment of haploid cells from a second cell line, pES12 (Table 2).

Two individual haploid-enriched ES cell lines were established from both pES10 and pES12 (hereafter referred to as h-pES10 and h-pES12) within five to six rounds of 1c-cell FACS enrichment and expansion (FIG. 1c (pES10), FIG. 5a (pES12)). These cell lines were grown in standard culture conditions for over 30 passages while including cells with a normal haploid karyotype (FIG. 1d, FIG. 5b). However, since diploidization occurred at a rate of 3-9% of the cells per day (FIG. 1e), cell sorting at every three to four passages was required for maintenance and analysis of haploid cells. Further, visualization of ploidy in adherent conditions was enabled by DNA fluorescence in situ hybridization (FISH) (FIG. 1f, FIG. 5c) and quantification of centromere protein foci (FIG. 1g, FIG. 5d; FIG. 6). In addition to their intact karyotype, haploid ES cells did not harbor significant copy number variations (CNVs) relative to their unsorted diploid counterparts (FIG. 5e). Importantly, we did not observe common duplications of specific regions in the two cell lines that would result in pseudo-diploidy. Therefore, genome integrity was preserved throughout haploid-cell isolation and maintenance. As expected, single nucleotide polymorphism (SNP) array analysis demonstrated complete homozygosity of diploid pES10 and pES12 cells across all chromosomes.

Both h-pES10 and h-pES12 exhibited classical human pluripotent stem cell features, including typical colony morphology and alkaline phosphatase activity (FIG. 2a, FIG. 2b). Single haploid ES cells expressed various hallmark pluripotency markers (NANOG, OCT4, SOX2, SSEA4 and TRA1-60), as confirmed in essentially pure haploid cultures by centromere foci quantification (>95% haploids) (FIG. 2c, FIG. 7). Notably, selective flow cytometry enabled to validate the expression of two human ES-cell-specific cell surface markers (TRA-1-60 and CLDN618) in single haploid cells (FIG. 2d). Moreover, sorted haploid and diploid ES cells showed highly similar transcriptional and epigenetic signatures of pluripotency genes (FIG. 2e, FIG. 2f). Since the haploid ES cells were derived as parthenotes, they featured distinct transcriptional and epigenetic profiles of maternal imprinting, owing to the absence of paternally-inherited alleles and paternal epigenetic profiles (FIG. 8).

Haploid cells are valuable for loss-of-function genetic screening because phenotypically-selectable mutants can be identified upon disruption of a single allele. To demonstrate the applicability of this principle in haploid human ES cells, we generated a genome-wide mutant library using a piggyBac transposon gene trap system that targets transcriptionally active loci (FIG. 2*g*, FIG. 8*e*), and screened for resistance to the purine analog 6-thioguanine (6-TG). Out of six isolated and analyzed 6-TG-resistant colonies, three harbored a gene trap insertion localizing to the nucleoside diphosphate linked moiety X-type motif 5 (NUDT5) autosomal gene (FIG. 2*h*). NUDT5 disruption was recently confirmed to confer 6-TG resistance in human cells,51 by acting upstream to the production of 5-phospho-d-ribose-1-pyrophosphate (PRPP), which serves as a phosphoribosyl donor in the hypoxanthine phosphoribosyltransferase 1 (HPRT1)-mediated conversion of 6-TG to thioguanosine monophosphate (TGMP) (FIG. 2*i*). Detection of a loss-of-function phenotype due to an autosomal mutation validates that genetic screening is feasible in haploid human ES cells.

Example 4. Molecular and Cellular Comparisons of Haploid and Diploid ES Cells

The ability of human ES cells to exist both as haploids and diploids led us to investigate whether these two ploidy states may differ in certain aspects of gene regulation and cell biology. To analyze haploid and diploid ES cells in the same phase of the cell cycle, we used FACS to isolate G1-phase haploid cells (1c) and compared them with isogenic G1-phase diploid cells (2c) from unsorted diploid cultures (FIG. 3*a*, FIG. 9*a*). We first aimed to uncover putative ploidy-associated differences by comparing the transcriptomes of haploid and diploid ES cells using RNA sequencing (RNA-Seq), considering that observed changes in expression levels would be relative to the total gene expression of each ploidy state, rather than representing absolute differences. On the genome-scale, undifferentiated haploid and diploid ES cells clustered closely with one another and separately from differentiated embryoid bodies (EBs), indicating resemblance that extends beyond the effects of genetic background (FIG. 3*b*). Nonetheless, a total of 565 differentially expressed genes were identified (>2-fold change, false discovery rate (FDR)<0.05), corresponding to 275 relatively upregulated genes and 290 relatively downregulated genes in haploids compared with diploids (FIG. 9*b*).

Notably, X chromosomal genes were significantly overrepresented among the relatively upregulated gene set (40%, P<0.001, Ψ2 goodness of fit test) (FIG. 3*c*), and the expression levels of X chromosomal genes alone clearly distinguished between haploid and diploid ES cells; the latter clustering even more closely with their differentiated derivatives than their undifferentiated haploid counterparts (FIG. 3*d*). These data are in line with an expected differential status of X chromosome inactivation (XCI) in haploid and diploid human ES cells: while the single X chromosome in haploids is transcriptionally active (Xa), one of the two X chromosomes in diploids often undergoes XCI (XaXi)19 as in female somatic cells. Indeed, haploid human ES cells exhibited a relative increase in X chromosomal gene expression compared with diploids by both RNA-Seq and expression microarray analysis, and lacked expression of the XCI-driving transcript XIST (FIG. 3*e*, FIG. 3*f*, FIG. 9*b*-9*d*), as observed in diploid XaXa human ES cells20. XCI is an epigenetic phenomenon, regulated by repressive histone modifications and DNA methylation. H3K27me3 foci were consistently observed in unsorted diploid ES cells, but not in their haploid-enriched counterparts (FIG. 3*g*). Moreover, methylome analysis showed that the X chromosome DNA methylation signature of haploid ES cells resembles that of diploid male ES cells (XaY), whose single-copy X chromosome is largely hypomethylated, as opposed to the composite pattern of a hypomethylated Xa and a hypermethylated Xi in diploid female cells (FIG. 3*h*). Interestingly, recently diploidized ES cells remained XaXa soon after diploidization (within 3 passages after haploid cell enrichment) by all the above-mentioned assays (FIG. 3*a*, FIG. 3*e*-3*h*).

Normalization to total gene expression, which is inherent to conventional relative gene expression analyses,21 resulted in seemingly similar expression levels of autosomal genes but higher levels of X-linked genes in haploid compared with diploid ES cells (FIG. 3*e*, FIG. 9*c*). However, assuming that the absolute expression of X-linked genes in haploid Xa and diploid XaXi cells are equivalent, these data suggest a genome-wide autosomal gene level reduction in haploid cells (FIG. 9*e*, FIG. 9*f*). In support of this notion, we found that total RNA amounts isolated from haploid ES cells were significantly lower than those obtained from the same numbers of diploid cells (FIG. 3*i*). An overall decrease in total gene expression implied that the physical dimensions of these cells may also be altered. Indeed, the average diameter ratio between sorted haploid and diploid ES cells in G1 was around 0.8 (9.6 and 11.5 μm, respectively), corresponding to haploid:diploid ratios of around 0.7 in surface area and around 0.6 in volume (FIG. 3*i*, FIG. 9*g*).

We subsequently focused on consistent differential regulation within autosomes. Based on transcriptional and DNA methylation analyses, we found significant enrichment of genes encoding proteins with signal peptides to be relatively downregulated in haploid ES cells (FIG. 9*h*). Remarkably, we also detected subtle yet significant relative upregulation of 11 genes involved in oxidative phosphorylation in haploid cells, including representatives encoding subunits of four out of the five complexes comprising this pathway (FIG. 3*j*, FIG. 9*i*). Furthermore, all 13 mitochondrial genes involved in oxidative phosphorylation were consistently upregulated in haploid cells as well (FIG. 3*j*), indicating coordinated regulation between these nuclear and mitochondrial genes. This coincides with a 32% increase in the mitochondrial DNA (mtDNA) to nuclear DNA ratio between haploids and diploids (FIG. 3*i*), suggesting that mitochondrial abundance relative to the nuclear DNA content is relatively higher in haploid cells.

Example 5. Differentiation of Human Haploid ES Cells

We next sought to assess the differentiation potential of haploid human ES cells of parthenogenetic origin. Although mammalian parthenogenetic development is restricted due to the non-equivalence of parental genomes,22,23 diploid human parthenogenetic pluripotent stem cells are functionally pluripotent as evident by their ability to give rise to all embryonic lineages.13,24,25 To address whether human parthenogenetic ES cells are capable of multilineage differentiation as haploids, we performed several differentiation assays, followed by ploidy and differentiation status characterizations of the resulting cells. 21-day-old EBs generated by spontaneous differentiation of haploid-enriched and diploid ES cells could not be distinguished by appearance (FIG. 4*a*), and the morphology of dissociated haploid-cellderived EB cells was consistent with differentiation (FIG. 10a). Notably, metaphase spread analysis revealed a haploid karyotype (FIG. 4b; 4/4 metaphases), and a largely haploid DNA profile (~70% haploids) was confirmed by flow cytometry in both h-pES10- and h-pES12-derived EB cells (FIG. 4c, FIG. 10b). We then compared the gene expression profiles of G1-sorted haploid ES and EB cells, focusing on 18 genes that showed clear specificity across eight tissues and pluripotent stem cells. For example, our gene set included CHRM1 (cholinergic receptor), KRT17 (keratine), MYL1 (myosin), REN (renin), ALB (albumin), CPA1 (carboxypeptidase), SFTPD (surfactant) and MALRD1 (MAM and LDL receptor), which are expressed in the brain, skin, muscle, kidney, liver, pancreas, lung and intestine, respectively (FIG. 4d). Whereas the expression of these lineage-specific genes was negligible in undifferentiated ES cells, all were expressed in haploid and diploid EB cells (FIG. 4d, FIG. 6c). In addition, haploid and diploid EB cells showed insignificant expression of pluripotency-specific genes, consistent with efficient differentiation and acquisition of somatic cell fates of all three embryonic germ layers.

To extend this analysis to more specific and potentially more mature cell types, we subjected haploid ES cells to directed differentiation assays. Haploid ES cells undergoing directed differentiation towards a neural fate for ten days remained haploid while efficiently giving rise to neural cell adhesion molecule 1 (NCAM1)-positive neural progenitor cells (NPCs, ~90% efficiency) (FIG. 4e, FIG. 11a, FIG. 11b). Sorted haploid NPCs expressed multiple neural-lineage-specific genes but not pluripotency-specific genes (FIG. 4f, FIG. 11c), indicating a robust exit from the pluripotent state while taking on a neural fate. XCI is imperative in diploid differentiated female cells, resulting in dosage compensation and a ratio of 1:2 between the X chromosome and autosomes. Since haploid ES cells are incapable of inactivating their single-copy X chromosome, an X:autosomes dosage imbalance of 1:1 should persist into the differentiated state. Indeed, both haploid NPCs and haploid EB cells showed an Xa signature contrary to the XaXi signature of diploid EB cells, as indicated by whole-genome expression analysis and XIST levels (FIG. 4g, FIG. 11d).

Neuronal differentiation was not restricted to the progenitor stage as the cells also differentiated with high efficiency (>90%) into mature TUJ1 (also known as β-tubulin III)-positive neurons by 20 days with notable persistence of haploid cells, as shown by both co-staining with centromeres (FIG. 4h; 47% haploids, n=104) and FISH analysis (FIG. 11e, FIG. 11f; 46% haploids, n=200). Similarly, haploid cells differentiated into cardiac troponin T type 2 (TNNT2)-expressing cardiomyocytes (FIG. 4i; 32% haploids, n=97) during an 11-day protocol resulting in spontaneously beating clusters and 39% (n=31) of haploid cells sorted from the whole culture (25% 1c cells) were confirmed as TNNT2-positive (FIG. 4j, FIG. 11g). Next, we differentiated haploid-enriched cultures (~70% haploids) to the pancreatic lineage, analyzing two stages of differentiation by centromere foci analysis, namely, specification to definitive endoderm and further into pancreatic cells. We observed robust differentiation (>90%) of both haploids and diploids into forkhead box A2 (FOXA2)-positive definitive endoderm cells (FIG. 4k; 56% haploids, n=112), and into pancreatic and duodenal homeobox 1 (PDX1)-positive pancreatic cells (FIG. 4l; 13% haploid, n=103), some of which were also positive for NK6 homeobox 1 (NKX6.1). In addition to centromere analysis, the persistence of haploid PDX1-positive cells was also confirmed by flow cytometry (FIG. 4m; 10% PDX1-positive 1c cells; FIG. 11h, FIG. 11i).

Finally, both haploid-enriched human ES cell lines gave rise to teratomas comprising cell types of ectodermal, mesodermal and endodermal origins as shown by histological and immunostaining analyses with TUJ1, α-smooth muscle actin (α-SMA) and α-fetoprotein (AFP) (FIG. 4n, FIG. 12a, FIG. 12b), meeting the most stringent criterion for human pluripotency in vivo. Importantly, no residual undifferentiated OCT4-positive cells could be detected (FIG. 4n, FIG. 12b). Upon dissection, DNA content analysis revealed that a considerable population of h-pES10-derived teratoma cells remained haploid (FIG. 4o). Combined analysis of serial sections from an independent, h-pES12-derived teratoma, by histology and FISH confirmed the existence of in vivo differentiated haploid human cells able to contribute to an organized tissue structure while responding to developmental signals (FIG. 4p). It is worth noting that haploid cells were identified in all analyzed teratomas (n=4), although with variable proportions, which may be influenced by the initial amount of haploid cells and/or the time length of differentiation.

REFERENCES

1. Leeb, M. & Wutz, A. Derivation of haploid embryonic stem cells from mouse embryos. *Nature* 479, 131-4 (2011).
2. Elling, U. et al. Forward and reverse genetics through derivation of haploid mouse embryonic stem cells. *Cell Stem Cell* 9, 563-74 (2011).
3. Yang, H. et al. Generation of genetically modified mice by oocyte injection of androgenetic haploid embryonic stem cells. *Cell* 149, 605-17 (2012).
4. Li, W. et al. Androgenetic haploid embryonic stem cells produce live transgenic mice. *Nature* 490, 407-11 (2012).
5. Li, W. et al. Genetic modification and screening in rat using haploid embryonic stem cells. *Cell Stem Cell* 14, 404-14 (2014).
6. Yang, H. et al. Generation of haploid embryonic stem cells from *Macaca fascicularis* monkey parthenotes. *Cell Res.* 23, 1187-200 (2013).
7. Wutz, A. Haploid mouse embryonic stem cells: rapid genetic screening and germline transmission. *Annu. Rev. Cell Dev. Biol.* 30, 705-22 (2014).
8. Tarkowski, A. K., Witkowska, A. & Nowicka, J. Experimental partheonogenesis in the mouse. *Nature* 226, 162-5 (1970).
9. Kaufman, M. H., Robertson, E. J., Handyside, A. H. & Evans, M. J. Establishment of pluripotential cell lines from haploid mouse embryos. *J. Embryol. Exp. Morphol.* 73, 249-61 (1983).
10. Egli, D. et al. Impracticality of egg donor recruitment in the absence of compensation. *Cell Stem Cell* 9, 293-4 (2011).
11. Leeb, M. & Wutz, A. Haploid genomes illustrate epigenetic constraints and gene dosage effects in mammals. *Epigenetics Chromatin* 6, 41 (2013).
12. Tesar, P. J. et al. New cell lines from mouse epiblast share defining features with human embryonic stem cells. *Nature* 448, 196-9 (2007).
13. Revazova, E. S. et al. Patient-specific stem cell lines derived from human parthenogenetic blastocysts. *Cloning Stem Cells* 9, 432-49 (2007).
14. Kim, K. et al. Recombination signatures distinguish embryonic stem cells derived by parthenogenesis and somatic cell nuclear transfer. *Cell Stem Cell* 1, 346-52 (2007).

15. Paull, D. et al. Nuclear genome transfer in human oocytes eliminates mitochondrial DNA variants. *Nature* 493, 632-7 (2013).
16. Leeb, M. et al. Germline potential of parthenogenetic haploid mouse embryonic stem cells. *Development* 139, 3301-5 (2012).
17. Takahashi, S. et al. Induction of the G2/M transition stabilizes haploid embryonic stem cells. *Development* 141, 3842-7 (2014).
18. Ben-David, U., Nudel, N. & Benvenisty, N. Immunologic and chemical targeting of the tight-junction protein Claudin-6 eliminates tumorigenic human pluripotent stem cells. *Nat. Commun.* 4, 1992 (2013).
19. Silva, S. S., Rowntree, R. K., Mekhoubad, S. & Lee, J. T. X-chromosome inactivation and epigenetic fluidity in human embryonic stem cells. *Proc. Natl. Acad. Sci. U.S.A.* 105, 4820-5 (2008).
20. Bruck, T., Yanuka, O. & Benvenisty, N. Human pluripotent stem cells with distinct X inactivation status show molecular and cellular differences controlled by the X-Linked ELK-1 gene. *Cell Rep.* 4, 262-70 (2013).
21. Lovén, J. et al. Revisiting global gene expression analysis. *Cell* 151, 476-82 (2012).
22. McGrath, J. & Solter, D. Completion of mouse embryogenesis requires both the maternal and paternal genomes. *Cell* 37, 179-83 (1984).
23. Barton, S. C., Surani, M. A. & Norris, M. L. Role of paternal and maternal genomes in mouse development. *Nature* 311, 374-6 (1984).
24. Mai, Q. et al. Derivation of human embryonic stem cell lines from parthenogenetic blastocysts. *Cell Res.* 17, 1008-19 (2007).
25. Stelzer, Y., Yanuka, O. & Benvenisty, N. Global analysis of parental imprinting in human parthenogenetic induced pluripotent stem cells. *Nat. Struct. Mol. Biol.* 18, 735-41 (2011).
26. Minkovsky, A., Patel, S. & Plath, K. Concise review: Pluripotency and the transcriptional inactivation of the female Mammalian X chromosome. *Stem Cells* 30, 48-54 (2012).
27. Biancotti, J. C. et al. The in vitro survival of human monosomies and trisomies as embryonic stem cells. *Stem Cell Res.* 9, 218-24 (2012).
28. Zhou, W. et al. HIF1α induced switch from bivalent to exclusively glycolytic metabolism during ESC-to-EpiSC/hESC transition. *EMBO J.* 31, 2103-16 (2012).
29. Shuai, L. et al. Durable pluripotency and haploidy in epiblast stem cells derived from haploid embryonic stem cells in vitro. *J. Mol. Cell Biol.* 1-29 (2015). doi:10.1093/jmcb/mjv044
30. Carette, J. E. et al. Haploid genetic screens in human cells identify host factors used by pathogens. *Science* 326, 1231-5 (2009).
31. Carette, J. E. et al. Ebola virus entry requires the cholesterol transporter Niemann-Pick C1. *Nature* 477, 340-3 (2011).
32. Wang, T., Wei, J. J., Sabatini, D. M. & Lander, E. S. Genetic screens in human cells using the CRISPR-Cas9 system. *Science* 343, 80-4 (2014).
33. Shalem, O. et al. Genome-scale CRISPR-Cas9 knockout screening in human cells. *Science* 343, 84-7 (2014).
34. Otto, S. P. & Jarne, P. Evolution. Haploids-hapless or happening? *Science* 292, 2441-3 (2001).
35. Noggle, S. et al. Human oocytes reprogram somatic cells to a pluripotent state. *Nature* 478, 70-5 (2011).
36. Cowan, C. A., Atienza, J., Melton, D. A. & Eggan, K. Nuclear reprogramming of somatic cells after fusion with human embryonic stem cells. *Science* 309, 1369-73 (2005).
37. Johannesson, B. et al. Comparable Frequencies of Coding Mutations and Loss of Imprinting in Human Pluripotent Cells Derived by Nuclear Transfer and Defined Factors. *Cell Stem Cell* 15, 634-642 (2014).
38. Chen, A. E. et al. Optimal timing of inner cell mass isolation increases the efficiency of human embryonic stem cell derivation and allows generation of sibling cell lines. *Cell Stem Cell* 4, 103-6 (2009).
39. Rao, P. H., Nandula, S. V & Murty, V. V. Molecular cytogenetic applications in analysis of the cancer genome. *Methods Mol. Biol.* 383, 165-85 (2007).
40. The Genotype-Tissue Expression (GTEx) project. *Nat. Genet.* 45, 580-5 (2013).
41. Yamada, M. et al. Human oocytes reprogram adult somatic nuclei of a type 1 diabetic to diploid pluripotent stem cells. *Nature* 510, 533-6 (2014).
42. Wanet, A. et al. Mitochondrial remodeling in hepatic differentiation and dedifferentiation. *Int. J. Biochem. Cell Biol.* 54, 174-85 (2014).
43. Kim, D.-S. et al. Robust enhancement of neural differentiation from human ES and iPS cells regardless of their innate difference in differentiation propensity. *Stem Cell Rev.* 6, 270-81 (2010).
44. Stelzer, Y., Sagi, I. & Benvenisty, N. Involvement of parental imprinting in the antisense regulation of oncomiR-372-373. *Nat. Commun.* 4, 2724 (2013).
45. Wang, L. et al. Differentiation of hypothalamic-like neurons from human pluripotent stem cells. *J. Clin. Invest.* 125, 796-808 (2015).
46. Chambers, S. M. et al. Highly efficient neural conversion of human ES and iPS cells by dual inhibition of SMAD signaling. *Nat. Biotechnol.* 27, 275-80 (2009).
47. Lian, X. et al. Directed cardiomyocyte differentiation from human pluripotent stem cells by modulating Wnt/β-catenin signaling under fully defined conditions. *Nat. Protoc.* 8, 162-75 (2013).
48. Hua, H. et al. iPSC-derived β cells model diabetes due to glucokinase deficiency. *J. Clin. Invest.* 123, 3146-53 (2013).
49. Pagliuca, F. W. et al. Generation of functional human pancreatic β cells in vitro. *Cell* 159, 428-39 (2014).
50. Rezania, A. et al. Reversal of diabetes with insulin-producing cells derived in vitro from human pluripotent stem cells. *Nat. Biotechnol.* 32, 1121-33 (2014).
51. Doench, J. G. et al. Optimized sgRNA design to maximize activity and minimize off-target effects of CRISPR-Cas9. *Nat. Biotechnol.* (2016). doi:10.1038/nbt.3437.
52. Cadiñanos, J. & Bradley, A. Generation of an inducible and optimized piggyBac transposon system. *Nucleic Acids Res.* 35, e87 (2007).
53. Wang, W. et al. Chromosomal transposition of PiggyBac in mouse embryonic stem cells. *Proc. Natl. Acad. Sci. U.S.A.* 105, 9290-5 (2008).
54. Chen, L. et al. Transposon activation mutagenesis as a screening tool for identifying resistance to cancer therapeutics. *BMC Cancer* 13, 93 (2013).

The foregoing description of the specific embodiments will so fully reveal the general nature of the invention such that others can, without undue experimentation, apply knowledge that is within the ordinary skill of those in the art to readily modify and/or adapt such specific embodiments for various applications without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance. The present invention is further described by the following claims.

The invention claimed is:

1. An enriched population of haploid human embryonic stem (ES) cells, wherein said population is capable of differentiating into a terminally differentiated haploid cell selected from a haploid mature neuron, and a haploid cardiomyocyte.

2. The enriched population of claim 1, comprising at least 5% haploid human ES cells.

3. The enriched population of claim 1, comprising at least 95% haploid human ES cells.

4. The enriched population of claim 1, wherein the enriched population is in human embryonic stem cell media.

5. The enriched population of claim 1, wherein said enriched population is derived from an artificially activated human oocyte.

6. The enriched population of claim 1, wherein said haploid human ES cells maintain pluripotentency in culture of at least 3 passages.

7. The enriched population of claim 1, wherein said haploid human ES cells maintain a haploid karyotype in culture of at least 3 passages.

8. The enriched population of claim 1, comprising at least 1 million haploid human ES cells.

9. A human ES cell line comprising the enriched population of claim 1.

* * * * *

UNITED STATES PATENT AND TRADEMARK OFFICE
CERTIFICATE OF CORRECTION

| | | |
|---|---|---|
| PATENT NO. | : 10,961,503 B2 | Page 1 of 1 |
| APPLICATION NO. | : 15/747103 | |
| DATED | : March 30, 2021 | |
| INVENTOR(S) | : Egli et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 66 days.

Signed and Sealed this
Thirty-first Day of January, 2023

Katherine Kelly Vidal
*Director of the United States Patent and Trademark Office*

```
                          SEQUENCE LISTING

<160> NUMBER OF SEQ ID NOS: 4

<210> SEQ ID NO 1
<211> LENGTH: 25
<212> TYPE: DNA
<213> ORGANISM: Homo sapiens
<220> FEATURE:
<221> NAME/KEY: misc_feature
<223> OTHER INFORMATION: Mitochondrial gene ND2
<220> FEATURE:
<221> NAME/KEY: misc_feature
<223> OTHER INFORMATION: Forward primer

<400> SEQUENCE: 1
tgttggttat acccttcccg tacta                                           25

<210> SEQ ID NO 2
<211> LENGTH: 25
<212> TYPE: DNA
<213> ORGANISM: Homo sapiens
<220> FEATURE:
<221> NAME/KEY: misc_feature
<223> OTHER INFORMATION: Mitochondrial gene ND2
<220> FEATURE:
<221> NAME/KEY: misc_feature
<223> OTHER INFORMATION: Reverse Primer

<400> SEQUENCE: 2
cctgcaaaga tggtagagta gatga                                           25

<210> SEQ ID NO 3
<211> LENGTH: 23
<212> TYPE: DNA
<213> ORGANISM: Homo sapiens
<220> FEATURE:
<221> NAME/KEY: misc_feature
<223> OTHER INFORMATION: Nuclear gene BECN1
<220> FEATURE:
<221> NAME/KEY: misc_feature
<223> OTHER INFORMATION: Forward Primer

<400> SEQUENCE: 3
ccctcatcac agggctctct cca                                             23

<210> SEQ ID NO 4
<211> LENGTH: 24
<212> TYPE: DNA
<213> ORGANISM: Homo sapiens
<220> FEATURE:
<221> NAME/KEY: misc_feature
<223> OTHER INFORMATION: Nuclear gene BECN1
<220> FEATURE:
<221> NAME/KEY: misc_feature
<223> OTHER INFORMATION: Reverse Primer

<400> SEQUENCE: 4
gggactgtag gctgggaact atgc                                            24
```